US010048275B2

(12) United States Patent
Kralj et al.

(10) Patent No.: US 10,048,275 B2
(45) Date of Patent: Aug. 14, 2018

(54) CARDIOTOXICITY SCREENING METHODS

(71) Applicant: Q-STATE BIOSCIENCES, INC., Cambridge, MA (US)

(72) Inventors: Joel Kralj, Somerville, MA (US); Graham Dempsey, Cambridge, MA (US); Christopher Werley, Cambridge, MA (US); Adam Cohen, Cambridge, MA (US)

(73) Assignee: Q-STATE BIOSCIENCES, INC., Cambridge, MA (US)

( * ) Notice: Subject to any disclaimer, the term of this patent is extended or adjusted under 35 U.S.C. 154(b) by 0 days.

(21) Appl. No.: 15/067,610

(22) Filed: Mar. 11, 2016

(65) Prior Publication Data

US 2016/0266144 A1 Sep. 15, 2016

Related U.S. Application Data

(60) Provisional application No. 62/132,850, filed on Mar. 13, 2015.

(51) Int. Cl.
| | |
|---|---|
| G01N 33/68 | (2006.01) |
| C12N 5/077 | (2010.01) |
| G01N 21/64 | (2006.01) |
| G01N 33/50 | (2006.01) |
| G01N 33/84 | (2006.01) |

(52) U.S. Cl.
CPC ....... *G01N 33/6872* (2013.01); *C12N 5/0657* (2013.01); *G01N 21/6428* (2013.01); *G01N 33/5014* (2013.01); *G01N 33/5041* (2013.01); *G01N 33/84* (2013.01); *G01N 21/6458* (2013.01); *G01N 2800/326* (2013.01)

(58) Field of Classification Search
CPC .......... G01N 33/5014; G01N 33/5041; G01N 33/84; G01N 33/6872; G01N 21/6428; G01N 2800/326; G01N 21/6458; C12N 5/0657
See application file for complete search history.

(56) References Cited

U.S. PATENT DOCUMENTS

| | | |
|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,591,444 A | 1/1997 | Boss, Jr. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,243,197 B1 | 6/2001 | Schalz |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,534,261 B1 | 3/2003 | Cox, III et al. |
| 6,607,882 B1 | 8/2003 | Cox, III et al. |
| 6,885,492 B2 | 4/2005 | DeSimone et al. |
| 6,898,004 B2 | 5/2005 | Shimizu et al. |
| 6,903,185 B2 | 6/2005 | Kim et al. |
| 6,972,892 B2 | 12/2005 | DeSimone et al. |
| 7,153,949 B2 | 12/2006 | Kim et al. |
| 7,459,333 B2 | 12/2008 | Richards et al. |
| 7,560,709 B2 | 7/2009 | Kimura et al. |
| 7,964,853 B2 | 6/2011 | Araya |
| 8,202,699 B2 | 6/2012 | Hegemann et al. |
| 8,403,160 B2 | 3/2013 | Hentzel |
| 8,532,398 B2 | 9/2013 | Filkins et al. |
| 8,562,658 B2 | 10/2013 | Shoham et al. |
| 8,580,937 B2 | 11/2013 | Spudich et al. |
| 8,603,790 B2 | 12/2013 | Deisseroth et al. |
| 8,603,809 B2 | 12/2013 | Kruse |
| 8,617,876 B2 | 12/2013 | Farrar et al. |
| 8,629,256 B2 | 1/2014 | Looger et al. |
| 8,647,870 B2 | 2/2014 | Hegemann et al. |
| 8,716,447 B2 | 5/2014 | Deisseroth et al. |
| 2005/0064474 A1 | 3/2005 | Urnov et al. |
| 2006/0188987 A1 | 8/2006 | Guschin et al. |

(Continued)

FOREIGN PATENT DOCUMENTS

| | | |
|---|---|---|
| EP | 2028268 A1 | 2/2009 |
| WO | 2007/053526 A1 | 5/2007 |

(Continued)

OTHER PUBLICATIONS

Bruegmann T. et al., "Optogenetic Control of Heart Muscle In Vitro and In Vivo", Nature Methods, Nov. 2010, vol. 7, No. 11, pp. 897-900 (Total 7 pages including Online methods). (Year: 2010).*
Arrenberg Q. et al., "Optogenetic Control of Cardiac Function", Science, Nov. 2010, vol. 330 (6006), pp. 971-974. (Year: 2010).*
Abdelfattah et al, 2014, Development of a red genetically encoded voltage indicator and its use with channelrhodopsin in all-optical electrophysiology, Biophys J 106(2)Supp 1:629a-630a.
Alami, 2014, Microtubule-dependent transport of TDP-43 mRNA granules in neurons is impaired by ALS-causing mutations, Neuron 81(3):536-543.
Almeida, 2012, Induced pluripotent stem cell models of progranulin-deficient frontotemporal dementia uncover specific reversible neuronal defects, Cell Rep 2(4):789-798.
Almeida, 2013, Modeling key pathological features of frontotemporal dementia with C9ORF72 repeat expansion in iPSC-derived human neurons, Acta Neuropathol 126(3):385-399.

(Continued)

*Primary Examiner* — Satyendra K Singh
(74) *Attorney, Agent, or Firm* — Brown Rudnick LLP; Thomas C. Meyers

(57) ABSTRACT

Screening compounds by exposing a plurality of cardiomyocytes to a compound, wherein the cardiomyocytes express an optogenetic reporter of membrane potential and an optogenetic reporter of calcium level; receiving light from the optogenetic reporter of membrane potential; creating an AP waveform using the received light; and analyzing the AP waveform to determine the presence or absence of a risk for arrhythmia associated with the compound.

7 Claims, 40 Drawing Sheets

(56) References Cited

U.S. PATENT DOCUMENTS

| | | |
|---|---|---|
| 2008/0131962 A1 | 6/2008 | Miller |
| 2011/0023144 A1 | 1/2011 | Weinstein et al. |
| 2012/0214236 A1 | 8/2012 | Bhatia et al. |
| 2012/0264623 A2 | 10/2012 | Fortunel et al. |
| 2013/0224756 A1 | 8/2013 | Cohen et al. |
| 2014/0135382 A1 | 5/2014 | Spudich et al. |
| 2014/0295413 A1 | 10/2014 | Cohen et al. |

FOREIGN PATENT DOCUMENTS

| | | |
|---|---|---|
| WO | 2009/047288 A1 | 4/2009 |
| WO | 2009/049181 A1 | 4/2009 |
| WO | 2010/027446 A2 | 3/2010 |
| WO | 2010/028089 A2 | 3/2010 |
| WO | 2012/027358 A1 | 3/2012 |
| WO | 2012/112737 A2 | 8/2012 |
| WO | 2013/078347 A2 | 5/2013 |

OTHER PUBLICATIONS

Ambasudhan, 2011, Direct reprogramming of adult human fibroblasts to functional neurons under defined conditions, Cell Stem Cell 9:113-118.

Amoroso, 2013, Accelerated high-yield generation of limb-innervating motor neurons from human stem cells, J Neurosci 33(2):574-86.

An, 2012, Genetic correction of Huntington's disease phenotypes in induced pluripotent stem cells, Cell Stem Cell 11 (2):253-263.

Ananiev, 2011, Isogenic pairs of wild type and mutant induced pluripotent stem cell (iPSC) lines from Rett syndrome patients as in vitro disease model, PLoS One 6(9):e25255.

Andrade, 2012, Evidence for premature aging due to oxidative stress in iPSCs from Cockayne syndrome, Hum Mol Genet 21:3825-3834.

Ataka, 2002, A genetically targetable fluorescent probe of channel gating with rapid kinetics, Biophys J 82:509-516.

Atasoy, 2009, A Flex switch targets channelrhodopsin-2 to multiple cell types for imaging and long-range circuit mapping, J Neurosci 28(28):7025-7030.

Badger, 2014, Parkinson's disese in a dish—using stem cells as a molecular tool, Neuropharmacol 76:88-96.

Beerli, 2002, Engineering polydactyl zinc-finger transcription factors, Nat. Biotechnol, 20:135-141.

Beja et al., 2001, Proteorhodopsin phototrophy in the ocean, Nature 411:786-789

Belfort, 1997, Homing endonucleases: keeping the house in order, Nucleic Acids Res 25(17):3379-3388.

Bilican et al, 2012, Mutant induced pluripotent stem cell lines recapitulate aspects of TDP-43 proteinopathies and reveal cell-specific vulnerability, PNAS 109(15):5803-5808.

Blokhuis, 2013, Protein aggregation in amyotrophic lateral sclerosis, Acta Neuropathol 125:777-794.

Boulting, 2011, A functionally characterized test set of human induced pluripotent stem cells, Nat Biotech 29(3):279-286.

Bozdagi, 2010, Haploinsufficiency of the autism-associated Shank3 gene leads to deficits in synaptic function, social interaction, and social communication, Mol Autism 1 (1): 15.

Brennand, 2011, Modelling schizophrenia using human induced pluripotent stem cells, Nature 473(7346):221-225.

Cardin, 2010, Targeted optogenetic stimulation and recording of neurons in vivo using cell-type-specific expression of Channelrhodopsin-2, Nat Protoc 5(2):247-54.

Carlson, 2013, Circular permutated red fluorescent proteins and calcium ion indicators based on mCherry, Protein Eng Des Sel 26(12):763-772.

Chanda, 2005, A hybrid approach to measuring electrical activity in genetically specified neurons, Nat Neuroscience 3:1619-1626.

Chang, 2013, Genome editing with RNA-guided Cas9 nuclease in zebrafish embryos, Cell Res 23:465-472.

Chaudhary, 2014, Measurement of optical action potentials and calcium transients in hIPSC-derived cardiomyocytes using the novel Optopatch fluorescent platform, poster presented in Oct. 2014.

Chen, 2013, Ultra-sensitive fluorescent proteins for imaging neuronal activity, Nature 499(7458):295-300.

Chiang, 2011, Integration-free induced pluripotent stem cells derived from schizophrenia patients with a DISC1 mutation, Molecular Psych 16:358-360.

Chung, 2013, Identification and rescue of a-synuclein toxicity in Parkinson patient-derived neurons, Science 342 (6161):983-7.

Cohen, 2013, All-optical electrophysiology with microbial rhodopsins, Event Page for lecture on Feb. 4, 2013, retrieved from the internet on Oct. 29, 2015, at: <<http://www.fitzpatrick.duke.edu/events/all-optical-electrophysiology-microbial-rhodopsins-0>>.

Cooper, 2012, Pharmacological rescue of mitochondrial deficits in iPSC-derived neural cells from patients with familial Parkinson's disease, Sci Transl Med 4(141):141ra90.

Corti, 2012, Genetic correction of human induced pluripotent stem cells from patients with spinal muscular atrophy, Sci Transl Med 4 (165):165ra162.

Dana, 2016, Sensitive red protein calcium indicators for imaging neural activity, bioRxiv, first published online Feb. 29, 2016, and available at biorxiv.org/content/biorxiv/early/2016/02/29/041780.full.pdf.

Davis, 2012, Cardiomyocytes derived from pluripotent stem cells recapitulate electrophyisiological characteristics of an overlap syndrome of cardiac sodium channel disease, Circulation 125(25):3079-3091.

Davis-Dusenbery, 2014, How to make spinal motor neurons, Development 141(3):491-501.

Denton, 2014, Loss of spastin function results in disease-specific axonal defects in human pluripotent stem cell-based models of hereditary spastic paraplegia, Stem Cells 32(2):414-23.

Diester, 2011, An optogenetic toolbox designed for primates, Nat Neurosci 14(3):387-97

Dimos, 2008, Induced pluripotent stem cells generated from patients with ALS can be differentiated into motor neurons, Science 321(5893):1218-21.

Donnelly, 2013, RNA toxicity from the ALS/FTD C9orf72 expansion is mitigated by antisense intervention, Neuron 80(2):415-28.

Dottori, 2011, Neural development in human embryonic stem cells—applications of lentiviral vectors, J Cell Bio 112(8):1955-62.

Du, 2012, Role of mismatch repair enzymes in GAA.TTC triplet-repeat expansion in Friedreich ataxia induced pluripotent stem cells, J Biol Chem 287(35):29861-29872.

Ebert, 2009, Induced pluripotent stem cells from a spinal muscular atrophy patient, Nature 457(7227):277-80.

Egawa, 2012, Drug screening for ALS using patient-specific induced pluripotent stem cells, Sci Transl Med 4(145):145ra104.

Flytzanis, 2014, Archaerohodopsin variants with enhanced voltage-sensitive fluorescence in mammalian and Caenorhabditis elegans neurons, Nat Comm 5:4894.

Fong, 2013, Genetic correction of tauopathy phenotypes in neurons derived from human induced pluripotent stem cells, Stem Cell Reports 1(3):1-9.

Foust, 2010, Action potentials initiate in the axon initial segment and propagate through axon collaterals reliably in cerebellar Purkinje neurons, J. Neurosci 30:6891-6902.

Gong, 2013, Enhanced Archaerhodopsin fluorescent protein voltage indicators, PLoSOne 8(6):e66959.

Gong, 2014, Imaging neural spiking in brain tissue using FRET-opsin protein voltage sensors, Nat Comm 5:3674.

Gordon, 2013, Amyotrophic later sclerosis: an update for 2013 clinical features, pathophysiology, management, and therapeutic trials, Aging and Disease 4(5):295-310.

Govorunova, 2013, Characterization of a highly efficient blue-shifted channelrhodopsin from the marine alga *Platymonas subcordiformis*, J Biol Chem 288(41):29911-29922.

Graf, 2011, Historical origins of transdifferentiation and reprogramming, Cell Stem Cell 9:504-516.

(56) References Cited

OTHER PUBLICATIONS

Han, 2011, Constructing and deconstructing stem cell models of neurological disease, Neuron 70(4):626-44.
HD iPSC Consortium, 2012, Induced pluripotent stem cells from patients with Huntington's disease show CAG-repeat-expansion-associated phenotypes. Cell Stem Cell 11(2):264-278.
Hick, 2013, Neurons and cardiomyocytes derived from induced pluripotent stem cells as a model for mitochondrial defects in Friedreich's ataxia, Dis Model Mech 6(3):608-21.
Higurashi, 2013, A human Dravet syndrome model from patient induced pluripotent stem cells, Mol Brain 6(1):19.
Hochbaum, 2012, Optopatch-all-optical electrophysiology Abstract, Neuroscience Poster # 229.02 Abstract.
Hochbaum, 2014, All-optical electrophysiology in mammalian neurons using engineered microbial rhodopsins, Nat Meth 11:825-833.
Hochbaum, 2014, Bringing bioelectricity to light: all-optical electrophysiology using microbial rhodopsins, Thesis, Harvard University (193 pages).
Hou, 2014, Simultaneous mapping of membrane voltage and calcium in zebrafish heart in vivo reveals chamber-specific developmental transitions in ionic currents, Front Phys 5:344.
Hwang, 2013, Efficient genome editing in zebrafish using a CRISPR-Cas system, Nat Biotechnol 31:227-229.
Inoue, 2015, Rational design of a high-affinity, fast, red calcium indicator R-CaMP2, Nat Meth 12(1):64-70.
International Search Report and Written Opinion dated Jan. 11, 2016, for International application No. PCT/US15/36181, with International filing date June 17, 2015 (14 pages).
International Search Report and Written Opinion dated Jul. 20, 2015, for International application No. PCT/US2015/026881, with International filing date Apr. 21, 2015 (12 pages).
International Search Report and Written Opinion dated Jul. 20, 2015, for International application No. PCT/US2015/026889 with International filing date Apr. 21, 2015 (13 pages).
International Search Report and Written Opinion dated Jul. 3, 2015, for International Patent Application No. PCT/US2015/026863 with International Filing Date Apr. 21, 2015 (10 pages).
International Search Report and Written Opinion dated Sep. 28, 2015, for International Patent Application No. PCT/US2015/026858 with International Filing Date Apr. 21, 2015 (20 pages).
Isalan, 2001, A rapid generally applicable method to engineer zinc fingers illustrated by targeting the HIV-1 promoter, Nat. Biotechnol 19:656-660.
Israel, 2012, Probing sporadic and familial Alzheimer's disease using induced pluripotent stem cells, Nature 482 (7384):216-20.
Jackson, 2001, Analysis of lung tumor initiation and progression using conditional expression of oncogenic K-ras, Genes & Dev 15:3243-3248.
Joung, 2013, TALENs: a widely applicable technology for targeted genome editing, Nat Rev Mol Cell Bio 14:49-55.
Kim,, 2010, Zebrafish model of tuberous sclerosis complex reveals cell-autonomous and non-cell-autonomous functions of mutant tuberin, Dis Model Mech., 4(2):255-67.
Kiskinis, 2014, Pathways disrupted in human ALS motor neurons identified through genetic correction of mutant SOD1, Cell Stem Cell (epub).
Klapoetke, 2014, Independent optical excitation of distinct neural populations, Nat Meth 11:338-346.
Koch, 2011, Excitation-induced ataxin-3 aggregation in neurons from patients with Machado-Joseph disease, Nature 480(7378):543-546.
Kondo, 2013, Modeling Alzheimer's disease with iPSCs reveals stress phenotypes associated with intracellular Abeta and differential drug responsiveness, Cell Stem Cell 12(4):487-496.
Kormann, 2011, Expression of therapeutic proteins after delivery of chemically modified mRNA in mice, Nat Biotech 29(2):154-7.
Kralj, 2011, Optical recording of action potentials in mammalian neurons using microbial rhodopsins, Nat Meth 9(1):90-95.
Krey, 2013, Timothy syndrome is associated with activity-dependent dendritic retraction in rodent and human neurons, Nat Neurosci 16(2):201-9.
Ku, 2010, Friedreich's ataxia induced pluripotent stem cells model intergenerational GAA•TTC triplet repeat instability, Cell Stem Cell 7(5):631-7.
Kuo, 2003, Differentiation of monkey embryonic stem cells into neural lineages, Biology of Reproduction 68:1727-1735.
Lee 2009, Modelling pathogenesis and treatment of familial dysautonomia using patient-specific iPSCs, Nature 461:402-406.
Lin, 2009, Characterization of engineered channelrhodopsin variants with improved properties and kinetics, Biophys J 96:1803-1814.
Liu, 2012, Signaling defects in iPSC-derived fragile X premutation neurons, Hum Mol Genet 21:3795-3805.
Liu, 2014, The more the better: modelling Dravet syndrom with induced pluripotent stem cell-derived neurons, Epil curr 14(1):33-34.
Lombardo, 2007, Gene editing in human stem cells using zinc finger nucleases and integrase-defective lentiviral vector delivery, Nat Biotechnol 25(11):1298-306.
Mahammad, 2013, Giant axonal neuropathy-associated gigaxonin mutations impair intermediate filament protein degredation, J Clin Invest 123(5):1964-75.
Makkerh, 1996, Comparative mutagenesis of nuclear localization signals reveals the importance of neutral and acidic amino acids, Current Biology 6:1025-1027.
Marchetto, 2010, A model for neural development and treatment of Rett syndrome using human induced pluripotent stem cells, Cell 143(4):527-39.
Maruyama, 2011, Detection of cells from calcium imaging data by non-negative matrix factorization, 21 Ann Conf. J Neur Net Soc.
Mattis, 2011, Principles for applying optogenetic tools derived from direct comparative analysis of microbial opsins, Nat. Meth. 9:159-172.
Mazzulli, 2011, Gaucher disease glucocerebrosidase and a-synuclein form a bidirectional pathogenic loop in synucleinopathies, Cell 146(1):37-52.
Meikle, 2007, A mouse model of tuberous sclerosis: neuronal loss of Tsc1 causes dysplastic and ectopic neurons, reduced myelination, seizure activity, and limited survival, J Neurosci. 27(21):5546-58.
Meikle, 2008, Response of a neuronal model of tuberous sclerosis to mammalian target of rapamycin (mTOR) inhibitors: effects on mTORC1 and Akt signaling lead to improved survival and function, J Neurosci., 28(21):5422-32.
Melkonian, 1986, A light and electron microscopic study of *Scherffelia dubia*, a new member of the scaly green flagellates (Prasinophyceae). Nord. J. Bot. 6:235-256.
Moehle, 2007, Targeted gene addition into a specified location in the human genome using designed zinc finger nucleases PNAS 104:3055-3060.
Molokanova, 2008, Bright future of optical assays for ion channel drug discovery, Drug Discov Today 13:14-22.
Mordwinkin, 2013, A review of human pluripotent stem cell-derived cardiomyocytes for high-throughput drug discover, cardiotoxicity screening and publication standards, J Cardiovasc Trans Res 6(1):22-30.
Mukamel, 2009, Automated analysis of cellular signals from large-scale calcium imaging data, Neuron 63(6):747-760.
Muratore, 2014, The familial Alzheimer's disease APPV717I mutation alters APP processing and tau expression in iPSC-derived neurons, Human Molecular Genetics, in press.
Musaro, 2010, State of the art and the dark side of amyotrophic lateral sclerosis, WJBC 1(5):62-68.
Nagel, 2005, Light activation of channelrhodopsin-2 in excitable cells of Caenorhabditis elegans triggers rapid behavioral responses, Curr. Biol. 15, 2279-2284.
Nakai, 2001, A high signal-to-noise Ca(2+) probe composed of a single fluorescent protein, Nat Biotech 19:137-141.
Neutze, 2002, Bacteriorhodopsin: a high-resolution structural view of vectorial proton transport, Biochimica et Biophysica Acta 1565:144-167.

(56) References Cited

OTHER PUBLICATIONS

Nihei, 2013, Enhanced aggregation of androgen receptor in induced pluripotent stem cell-derived neurons from spinal and bulbar muscular atrophy, J Biol Chem 288(12):8043-52.
Normand, 2013, Temporal and mosaic Tsc1 deletion in the developing thalamus disrupts thalamocortical circuitry, neural function, and behavior, Neuron, 5;78(5):895-909.
Pang, 2011, Induction of human neuronal cells by defined transcription factors, Nature 476:220-223.
Pasinelli, 2006, Molecular biology of amyotrophic lateral sclerosis: insights from genetics, Nat Rev Neurosci 7:710-723.
Peça, 2011, Shank3 mutant mice display autistic-like behaviours and striatal dysfunction, Nature 472 (7344): 437-42.
Piao, 2015, Combinatorial mutagenesis of the voltage-sensing domain enables the optical resolution of action potentials firing at 60 Hz by a genetically encoded fluorescent sensor of membrane potential, J Neurosci 35(1):372-385.
Popovic, 2011, The spatio-temporal characteristics of action potential initiation in layer 5 pyramidal neurons: a voltage imaging study, J. Physiol. 589:4167-4187.
Przybylo, 2010, Fluorescence techniques for determination of the membrane potentials in high throughput screening, J Fluoresc 20(6):1139-1157.
Reinhardt, 2013, Genetic correction of a LRRK2 mutation in human iPSCs links parkinsonian neurodegeneration to ERK-dependent changes in gene expression, Cell Stem Cell 12(3):354-367.
Rothermel, 2013, Transgene expression in target-defined neuron populations mediated by retrograde infection ith adeno-associated viral vectors, J Neurosci 33(38):195-206.
Rotunno, 2013, An emerging role for misfolded wild-type SOD1 in sporadic ALS pathogenesis, Front Cell Neurosci 7:a253.
Saccon, 2013, Is SOD1 loss of function involved in amyotrophic lateral sclerosis?, Brain 136:2342-2358.
Sager, 2014, Rechanneling the cardiac proarrythmia safety paradigm: a meeting from the cardiac safety research consortium, Am Heart J 167(3):292-300.
Sanders, 2013, LRRK2 mutations cause mitochondrial DNA damage in iPSC-derived neural cells from Parkinson's disease patients: reversal by gene correction. Neurobiol Dis 62:381-6.
Santiago, 2008, Targeted gene knockout in mammalian cells by using engineered zinc-finger nucleases, PNAS 105:5809-5814.
Sapunar, 2012, Dorsal root ganglion—a potential new therapeutic target for neuropathic pain, J Pain Res 1:31-38.
Sareen, 2012, Inhibition of apoptosis blocks human motor neuron cell death in a stem cell model of spinal muscular atrophy. PLoS One 7(6):e39113.
Sauer, 1988, Site-specific DNA recombination in mammalian cells by the Cre recombinase of bacteriophage P1, PNAS 85:5166-70.
Saunders, 2012, Novel recombinant adeno-associated viruses for Cre activated and inactivated transgene expression in neurons, Front Neural Circuits 6:47.
Seibler, 2011, Mitochondrial Parkin recruitment is impaired in neurons derived from mutant PINK1 induced pluripotent stem cells, J Neurosci 31(16):5970-6.
Shi, 2012, A human stem cell model of early Alzheimer's disease pathology in Down syndrome, Sci Transl Med 4 (124):124ra129.
Siegel, 1997, A genetically encoded optical probe of membrane voltage. Neuron 19:735-741.
Son, 2011, Conversion of mouse and human fibroblasts into functional spinal motor neurons, Cell Stem Cell 9:205-218.

Song, 2012, Neural differentiation of patient specific iPS cells as a novel approach to study the pathophysiology of multiple sclerosis, Stem Cell Res 8(2):259-73.
St-Pierre, 2014, High-fidelity optical reporting of neuronal electrical activity with an ultrafast fluorescent voltage sensor, Nat Neurosci 17(6):884.
Subramaniam, 1992, Aspartic acid 85 in bacteriorhodopsin functions both as proton acceptor and negative counterion to the Schiff base, J Biol Chem 267(36):25730-25733.
Sánchez-Danés, 2012, Disease-specific phenotypes in dopamine neurons from human iPS-based models of genetic and sporadic Parkinson's disease, EMBO Mol Med, 4: 380-395.
Takahashi, 2006, Induction of pluripotent stem cells from mouse embryonic and adult fibroblast cultures by defined factors Cell 126:663-676.
Takahashi, 2007, Induction of pluripotent stem cells from adult human fibroblasts by defined factors, Cell 131:861-872.
Trounson, 2012, Human disease modeling with induced pluripotent stem cells, Curr Op Gen Dev 22(5):509-516.
Urnov, 2005, Highly efficient endogenous human gene correction using designed zinc-finger nucleases, Nature 435 (7042):646-51
Vazin et al., 2014, Efficient derivation of cortical glutamatergic neurons from human pluripotent stem cells: a model system to study neurotoxicity in Alzheimer's disease, Neurobiol Dis 62:62-72.
Vierbuchen, 2010, Direct conversion of fibroblasts to functional neurons by defined factors, Nature4 63:1035-1041.
Wah, 1998, Structure of FokI has implications for DNA cleavage, PNAS 95:10564-10569.
Wainger, 2014, Intrinsic membrane hyperexcitability of amyotrophic lateral sclerosis patient-derived motor neurons, Cell Reports 7(1):1-11.
Wang, 2011, Synaptic dysfunction and abnormal behaviors in mice lacking major isoforms of Shank3, Hum. Mol. Genet. 20 (15): 3093-108.
Wardill, 2013, A neuron-based screening platform for optimizing genetically-encoded calcium indicators, PLoS One 8(10):e77728.
Wernig, 2002, Tau EGFP embryonic stem cells: an efficient tool for neuronal lineage selection and transplantation. J Neuroscience Res 69:918-24.
Wlodarski,, 2008, Tuberin-heterozygous cell line TSC2ang1 as a model for tuberous sclerosis-associated skin lesions, Int J Mol Med. 21(2):245-50.
Wu, 2013, Improved orange and red $Ca2+$ indicators and photophysical considerations for optogenetic applications, ACS Chem Neurosci 4(6):963-972.
Xiao, 2013, Chromosomal deletions and inversions mediated by TALENS and CRISPR/Cas in zebrafish, Nucl Acids Res 1-11.
Yang, 2013, A small molecule screen in stem-cell-derived motor neurons identifies a kinase inhibitor as a candidate therapeutic for ALS, Cell Stem Cell 12(6):713-726.
Yizhar, 2011, Optogenetics in neural systems, Neuron 71(1):9-34.
Yoo, 2011, MicroRNA mediated conversion of human fibroblasts to neurons, Nature 476:228-231.
Zangi, 2013, Modified mRNA directs the fate of heart progenitor cells and induces vascular regeneration after myordial infarction, Nat Biotech 31:898-907.
Zhang, 2013, Rapid single-step induction of functional neurons from human pluripotent stem cells, Neuron 78(5):785-798.
Zhao, 2011, An expanded palette of genetically encoded $Ca2+$ indicators, Science 333(6051):1888-1891.
Zoghbi, 2012, Synaptic Dysfunction in Neurodevelopmental Disorders Associated with Autism and Intellectual Disabilities, Cold Spring Harb Perspect Biol. 4(3), J Neurol Sci. 217(1):47-54.

\* cited by examiner

| Drug ID | Vial code | conc. 1 (µM) | conc. 2 (µM) | conc. 3 (µM) | conc. 4 (µM) | |
|---|---|---|---|---|---|---|
| Ranolazine dihydrochloride | 251 | 1 | 3 | 10 | 30 | Late Nav1.5 block |
| Quinidine | 252 | 0.3 | 1 | 3 | 10 | Na+ channel block |
| Nifedipine | 253 | 0.01 | 0.03 | 0.1 | 0.3 | Ca++ channel block |
| Moxifloxacin hydrochloride | 254 | 3 | 10 | 30 | 100 | hERG channel block |
| Mexiletine hydrochloride | 255 | 1 | 3 | 10 | 30 | Na channel block |
| JNJ 313 | 256 | 0.01 | 0.03 | 0.1 | 0.3 | Iks channel block |
| Flecainide acetate | 257 | 0.1 | 0.3 | 1 | 3 | Late Nav1.5 block |
| E-4031 dihydrochloride | 258 | 0.003 | 0.01 | 0.03 | 0.1 | hERG channel block |

FIG. 17

CARDIOTOXICITY SCREENING METHODS

CROSS-REFERENCE TO RELATED APPLICATION

This application claims the benefit of, and priority to, U.S. Provisional Application No. 62/132,850, filed Mar. 13, 2015, the contents of which are incorporated by reference.

FIELD OF THE INVENTION

The invention generally relates to screening compounds for cardiac effects.

BACKGROUND

Heart disease and other forms of cardiovascular disease are leading causes of death in the industrialized world. While a great amount of money is spent each year on cardiovascular drugs, there are still great gains to be made by developing new drugs that treat cardiovascular diseases. Drug discovery and development requires that potential drugs must be examined for adverse cardiovascular effects, a process that is expensive and difficult. It is estimated that more than 40% of compounds that enter phase III clinical trials are dropped, often for toxicity. Off-target cardiac toxicity, or cardiotoxicity, is a significant problem in bringing a new drug to market.

Existing approaches to studying cardiotoxicity are lacking. Some approaches focus on studying a compound's tendency to block the ion channel encoded by the human ether-a-go-go related gene (hERG) as a proxy for cardiotoxicity, but this oversimplification likely keeps many promising drugs from being discovered. Other approaches test for prolongation of the QTc interval in non-human animals, but animal studies are expensive and slow. Other approaches use the technique of patch-clamp electrophysiology on primary or human stem cell-derived myocytes to probe effects of compounds on the action potential waveform, but patch clamp measurements require a skilled operator and are very laborious. Patch clamp measurements also fail to probe the calcium handling dynamics of the myocyte. A think tank sponsored by the Food and Drug Administration has proposed a Comprehensive in vitro Proarrhythmia Assay (CiPA) to potentially evaluate drug effects on multiple ion channels. The CiPA initiative seeks to probe cardiotoxicity in human stem cell-derived cardiomyocytes, but an accurate, and rapid assay is needed to quantify voltage and calcium handling, under defined pacing conditions.

SUMMARY

The invention provides methods of optically obtaining an action potential (AP) and calcium transient (CT) waveform from a stem-cell derived cardiomyocyte to characterize an arrhythmia in the cardiomyocyte. The cardiomyocyte is caused to express a rhodopsin-type transmembrane protein that generates an optical signal in response to changes in membrane potential, thereby functioning as an optical reporter. In response to a stimulus—which itself may be optical through the use of a microbial channelrhodopsin or similar protein—an action potential propagates through the cardiomyocyte causing a change in the fluorescence of the reporter. Light from the reporter is detected and analyzed to construct the AP waveform. An arrhythmia in the constructed AP waveform can be detected or characterized, e.g., by comparison to a known standard or other analytical techniques. Using such a system, a compound's effect on cardiomyocytes can be studied. The cardiomyocyte is exposed to the compound and any resulting perturbation to the AP waveform, or arrhythmia, associated with exposure to the compound is observed. Since the optical reporter can include a voltage reporter, an ion reporter (e.g., for $[Ca^{2+}]$), others, or combinations thereof, the assay detects the effect of the compound across multiple ion channels of the cardiomyocyte as revealed through all features of the AP waveform and not necessarily only QT prolongation. By these means, the invention provides methods of cardiotoxicity screening that probe the phenomenological effects of compounds in great detail and do not require ungainly voltage clamping or patch clamping techniques, allowing for higher throughput than prior art methods. Since methods of the invention examine many aspects of a compound's effects on cardiomyocytes, the method provide a more detailed and accurate evaluation of the compound than prior art methods. Thus methods of the invention may be employed in drug discovery and development to help identify drugs with life-saving potential that should proceed further in clinical trials.

In certain aspects, the invention provides a method for measuring cardiomyocyte membrane potential by maintaining in vitro a cardiomyocyte that expresses a genetically encoded optical reporter of change in membrane potential, receiving an optical signal from the reporter, creating an AP waveform using the optical signal, and analyzing the AP waveform to determine the presence or absence of an arrhythmia. The cardiomyocyte may also express an optically actuated ion channel, a protein that reports a change in an intracellular calcium level, or both. The method may include exposing the cardiomyocyte to a compound and detecting a change in the AP waveform and a change in the intracellular calcium level upon exposure of the cardiomyocyte to the compound. The optical reporter of change in membrane potential may include a microbial rhodopsin, and specifically may include a QuasAr reporter derived from Archaerhodopsin 3. The optically actuated ion channel may include a channelrhodopsin, and may specifically include the CheRiff protein derived from *Scherffelia dubia*. The protein that reports changes in intracellular calcium levels may include a GCaMP variant or an RCaMP variant. The method may include assigning a non-binary cardiotoxicity score to the compound based at least in part on the detected change.

A key challenge in combining multiple optical modalities (e.g. optical stimulation, voltage imaging, $Ca^{2+}$ imaging) is to avoid optical crosstalk between the modalities. The pulses of light used to deliver optical stimulation should not induce fluorescence of the reporters; the light used to image the reporters should not actuate to light-gated ion channel; and the fluorescence of each reporter should be readily distinguished from the fluorescence of the others. In some aspects of the invention, this separation of modalities is achieved by selecting an actuator and reporters with little spectral overlap. In one embodiment, the actuator is activated by violet light, the $Ca^{2+}$ reporter is excited by yellow light and emits orange light, and the voltage reporter is excited by red light and emits near infrared light.

In other aspects of the invention the separation of modalities is achieved by spatially segregating one or more components into different cells or different regions of the dish. In one embodiment, the actuator is activated by blue light, and cells expressing the actuator are localized to one sub-region of the dish. Other cells express a blue light-excited $Ca^{2+}$ indicator and a red light-excited voltage indicator. These reporter cells are grown in an adjacent region of the dish, in contact with the actuator-expressing cells. Flashes of blue light targeted to the actuator-expressing cells initiate APs. These APs trigger APs in the reporter-expressing cells via in-plane conduction.

The invention may further comprise genetic constructs for ensuring mutually exclusive gene expression of the light-gated ion channel and the fluorescent reporter protein or proteins. Mutually exclusive gene expression ensures that ionic currents through the light-gated ion channel do not lead to perturbations in the ion concentration in cells whose voltage and $Ca^{2+}$ levels are being measured.

In some embodiments, the cardiomyocyte is stimulated by a second cardiomyocyte that expresses a light-gated ion channel. The second cardiomyocyte may also express the optical reporter of change in membrane potential. The cardiomyocyte and the second cardiomyocyte may either or both be hiPSC-derived cardiomyocytes.

In some embodiments the cardiomyocyte may be optically stimulated in a predetermined temporal pattern to test its robustness to arrhythmia. The pattern may comprise beating at a set of constant rates of (e.g. 1 Hz, 2 Hz, 3 Hz). Alternatively, the pattern may comprise a sudden step in beat-rate (e.g. from 1 Hz to 2 Hz, or from 2 Hz to 1 Hz). Alternatively, the pattern may comprise introduction of brief optical stimuli at predetermined times during an AP waveform, to test the robustness of the AP to ectopic beats. Alternatively, the pattern may comprise a ramp of gradually increasing stimulus rate, to determine the maximum frequency at which the cardiomyocytes can beat. In certain embodiments, obtaining the optical signal and optically pacing the cardiomyocytes are performed using an optical microscopy system, which system may use a digital micromirror device to control the spatial pattern of the illumination.

The method may include exposing the cardiomyocyte to a compound, and detecting an effect of the compound on the AP waveform. The cardiomyocyte may be exposed to the compound at different concentrations. A cardiotoxicity score may be assigned to the compound based at least in part on the detected change. In certain embodiments, the cardiomyocyte also expresses a protein that reports a change in an intracellular calcium level, and the method includes determining a change in the intracellular calcium level associated with the exposure of the cardiomyocyte to the compound. Methods of the invention can include measuring an AP prolongation corresponding to the clinically recorded QT interval, as well as at least one other change in the AP waveform associated with the exposure of the cardiomyocyte to the compound. For example, one or more of early after depolarization, alternans, cessation of beating, change in spontaneous beat rate, conduction velocity, action potential width at 30% maximum depolarization, action potential width at 70% maximum depolarization, action potential width at 90% maximum depolarization, voltage drift during diastolic interval, and maximal upstroke velocity could be measured. Further, $Ca^{2+}$ amplitude and presence of $Ca^{2+}$ sparks could be measured. Preferably, a non-binary cardiotoxicity score is assigned to the compound based at least in part on the change in the intracellular calcium transient, and the change in the AP waveform.

Aspects of the invention provide a cell with a eukaryotic genome that expresses a voltage-indicating microbial rhodopsin and a light-gated ion channel such as an algal channel rhodopsin as described herein. The cell may be a cardiomyocyte, neuron, or other electrically-active cell. The microbial rhodopsin may provide an optical reporter of membrane electrical potential such as QuasAr1 or QuasAr2. Preferably the cell also expresses a protein that reports a change in an intracellular calcium level such as a genetically-encoded calcium indicator (GECI). Exemplary GECIs include GCaMP variants. The GCaMP sensors generally included a GFP, a calcium-binding calmodulin protein (CaM), and a CaM-binding peptide. The protein that reports a change in an intracellular calcium level may be, for example, jRCaMP1a, jRGECO1a, or RCaMP2. In some embodiments, the light-gated ion channel comprises a blue-shifted actuator with an excitation maximum at a wavelength <450 nm and the protein that reports the change in the intracellular calcium level comprises a red-shifted calcium indicator with an excitation maximum between 520 nm and 570 nm inclusive. The light-gated ion channel can include a blue-shifted actuator such as TsChR or PsChR.

In preferred embodiments, the microbial rhodopsin, the light-gated ion channel, or both are expressed from a gene that is integrated into the genome. The microbial rhodopsin may be a QuasAr protein with the light-gated ion channel a channelrhodopsin, and the cell may also include a genetically-encoded calcium indicator such as GCaMP6f, jRCaMP1a, jRGECO1a, or RCaMP2. In some embodiments, the light-gated ion channel includes a violet-excited optogenetic actuator and cell further includes a red-shifted genetically-encoded calcium indicator (e.g., the violet-excited optogenetic actuator is a channelrhodopsin and the red-shifted genetically-encoded calcium indicator is jRCaMP1a, jRGECO1a, or RCaMP2.

In some aspects, the invention provides a cell culture. The cell culture includes a first plurality of animal cells that express an optogenetic actuator and a second plurality of animal cells electrically contiguous with the first plurality of animal cells. The second plurality of animal cells expresses a genetically-encoded optical reporter of activity. The optogenetic actuator may include a channelrhodopsin, the genetically-encoded optical reporter of activity may include a microbial optical reporter of membrane electrical potential, or both. At least some of the first or second plurality of animal cells may express a genetically encoded Ca++ indicator. The genetically encoded Ca++ indicator may be, for example, a GCaMP variant such as GCaMP6f, jRCaMP1a, jRGECO1a, or RCaMP2.

In some embodiments, the first plurality of animal cells are spatially segregated from yet in electrical contact with the second plurality of animal cells. The genetically-encoded optical reporter activity may be a microbial optical reporter of membrane electrical potential and at least some of the second plurality of animal cells may express a genetically encoded Ca++ indicator.

In a fourth aspect, the invention provides a method for screening compounds. The method includes: exposing a plurality of cardiomyocytes to a compound, wherein the cardiomyocytes express an optogenetic reporter of membrane potential and an optogenetic reporter of calcium level (also, optionally, an optogenetic actuator of electrical activity); receiving light from the optogenetic reporter of membrane potential; creating an AP waveform using the received light; and analyzing the AP waveform to determine the presence or absence of a risk for arrhythmia associated with the compound. In the fourth aspect, the optogenetic actuator of electrical activity may be a light-gated ion channel such as, for example, an algal channel rhodopsin (preferably CheRiff, TsChR, or PsChR). In the fourth aspect, the optogenetic reporter of membrane potential may be a microbial rhodopsin such as an Arch variant (e.g., Arch D95N, preferably QuasAr2 or QuasAr1). In the fourth aspect, the optogenetic reporter of calcium level is preferably a genetically encoded calcium indicator (GECI) such as jRGECO1a, jRCaMP1a, or jRCaMP1b. Preferably, the optogenetic reporter of membrane potential and the optogenetic reporter of calcium level are co-expressed on a fusion protein (e.g., microbial rhodopsin+GECI). In preferred embodiments of the fourth aspect, the method includes assigning a non-binary cardiotoxicity score to the compound based at least in part on the presence or absence of a risk for arrhythmia. Preferably, the method includes optically pacing the cardiomyocyte via the light-gated ion channel (e.g., with the detecting the light and the optically pacing performed using an optical microscopy system).

BRIEF DESCRIPTION OF THE DRAWINGS

FIG. 5 shows simultaneous voltage and calcium recording of paced cardiomyocytes transfected with CheRiff, QuasAr2, and the red-shifted calcium sensor jRGECO1a.

FIG. 17 shows the compounds used and the concentration ranges tested for each.

FIG. 17 lists compounds for testing with cardiomyocytes.

DETAILED DESCRIPTION

The invention provides optogenetic systems and methods to stimulate depolarization through paced cultures and to visualize simultaneously the AP and CT of cardiomyocytes (CMs) derived from human induced pluripotent stem cells (hiPSC) or human embryonic stem cells (hESC). Stimulation and pacing of CMs are achieved through the use of a channelrhodopsin such as the variant called CheRiff. CheRiff is a highly sensitive, light-gated ion channel that elicits APs upon illumination with blue light. Expression of CheRiff in a subset of cardiomyocytes may be used to pace an entire syncytium through gap junction-mediated electrical conduction. Detection of AP and CT waveforms is accomplished through the use of a protein fusion of QuasAr2 with GCaMP6f called CaViar for 'Ca$^{2+}$ and voltage indicator'. The use of CaViar allowed robust measurement of the membrane potential changes and Ca$^{2+}$ handling of the cardiomyocytes. The described systems and methods may be used as a platform for cardiotoxicity screening. Compounds may be tested at the endogenous beat rate and multiple paced rates to identify rate-dependent effects that might be masked in an unpaced preparation. Testing under conditions of chronic drug exposure may demonstrate the ability of long-term measurements to be made following addition of the compound. The described methods provide the ability to evaluate the cardiotoxic effects, including AP morphology, kinetics and CTs, of clinically relevant compounds in an optically paced cardiomyocyte preparation using fluorescent proteins. As described herein, the Optopatch technology reports the electrophysiological and Ca$^{2+}$ response of hiPSC-derived cardiomyocytes to pharmacological perturbations, with high accuracy, high throughput, and high information content. Optopatch generally refers to systems that include an optical reporter and an optical actuator such as an Arch-based voltage reporter like one of the QuasArs and a light-gated ion channel for use as an optical actuator such as CheRiff. The described systems should prove useful in reaching one of the major end goals of the CiPA initiative, namely a new in vitro assay with hiPSC-derived CMs for the accurate reporting of cardiotoxic effects of drug compounds.

Figure 1:
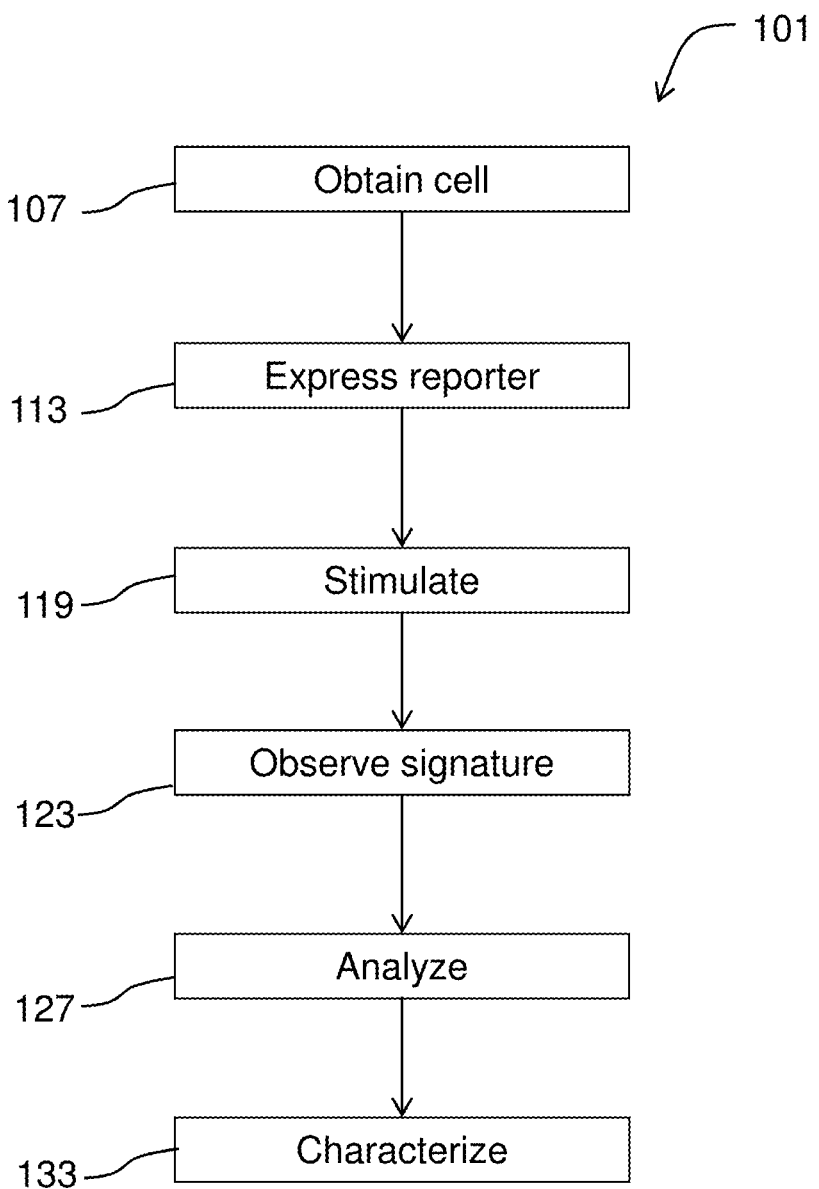
FIG. 1 diagrams a method to characterize a cardiomyocyte.

FIG. 1 diagrams a method 101 to characterize 133 a cardiomyocyte. Methods are described herein to obtain 107 an electrically excitable cell such as preferably an hiPSC-derived or hESC-derived cardiomyocyte. An optical actuator of, and an optical reporter of, electrical activity are incorporated into one or more cells in an electrically coupled syncytial culture. Preferably, the cell will express 113 (e.g., by translation) the reporter. Upon exposure to appropriate light, by the action of the optogenetic actuator, an action potential propagates through the cardiomyocyte.

For a typical action potential, membrane potential starts out at −90 mV at time zero. Illuminating the actuator at time=1 ms raises the membrane potential above the threshold. The membrane potential rises to about +25 mV at 2 ms and then drops to about −90 mV at 200 ms. Using method described herein, an optical signal from the optical reporter in response to a stimulation of the cell is obtained. The optical signal is used to create a measurement of the action potential. To characterize the cell, one may observe 123 and analyze or evaluate 127 the action potential and any effects such as perturbations associated with a test compound. By evaluating perturbations to the action potential, one may characterize 133 cardiotoxicity of one or more test compounds. Key aspects that can be read or calculated from an action potential include the action potential duration at 50% of repolarization (AP50), the action potential duration at 90% of repolarization (AP90), the action potential rise time, and spontaneous beat rate. One insight important to the invention is that the action potential is a product of a number of different inputs including several different ionic currents and that more insight into cardiotoxicity can be gleaned by evaluating more than one of these inputs in an assay simultaneously (e.g., such as membrane potential and an ionic concentration).

1. Obtaining Cell(s)

Cells for use with the invention preferably include cardiac cells although other cell types may have applications in methods of the invention. Suitable cells may include mammalian cells, including mouse, rat, and human cells or other animal cells. The cells may also include immortalized cell lines such as HEK, HeLa, CHO, 3T3, PC12, which may be particularly useful in applications of the methods for drug screens. The cells are preferably cardiomyocytes. Cells are obtained by any suitable means. For example, terminally differentiated hiPSC-derived cardiomyocytes may be purchased. One may purchase the cardiomyocytes sold under the trademark ICELL by Cellular Dynamics Inc. (Madison, Wis.) or Cor.4U by Axiogenesis. Differentiated cells such as cardiomyocytes may be dissociated and plated onto glass coverslips coated with poly-d-lysine and laminin. Cardiomyocytes may be fed with a suitable medium such as a maintenance medium. After plating (e.g., about five days after plating), hiPSC-derived cardiomyocytes may be transduced with vectors described below.

In alternative embodiments, cells may be obtained from a donor or patient. Methods of the invention can include obtaining one or more cells such as fibroblasts, e.g., by dermal biopsy These dermal fibroblasts may be transdifferentiated directly into cardiomyocytes or reprogrammed into iPSCs, and then differentiated into cardiomyocytes. In some embodiments, the cells are cardiomyocytes. In one embodiment, the cells are cardiomyocytes that have been differentiated from stem cells.

2. Optogenetic Systems

In a preferred embodiment, methods of cardiotoxicity screening include incorporating into a cell an optical actuator of electrical activity and an optical reporter of electrical activity—i.e., both into one cell or each of a plurality of cells. In some embodiments, a cell will receive one of the actuator and reporter. In certain embodiments, a cell will receive both via transfection with a single vector that includes genes coding for each of the reporter and actuator. As used herein the term "optical reporter" refers to a structure or system employed to yield an optical signal indicative of cellular electrical activity such as a voltage drop across a membrane or an action potential or to a structure or system employed to yield an optical signal indicative of the concentration of an analyte of interest in a specified cellular compartment such as $Ca^{2+}$ ion concentration in the cytoplasm. As used herein, the term "membrane potential" refers to a calculated difference in voltage between the interior and exterior of a cell. In one embodiment membrane potential, $\Delta V$, is determined by the equation $\Delta V=V(interior)-V(exterior)$. By convention, $V(exterior)$ is regarded as 0 V, so then $\Delta V=V(interior)$.

2a. Optogenetic Reporters

Cardiomyocytes may express an optical reporter of electrical activity. Expressing an optical reporter of electrical activity can include transformation with an optogenetic reporter. For example, the cell may be transformed with a vector comprising an optogenetic reporter and the cell may also be caused to express an optogenetic actuator by transformation. In certain embodiments, the differentiated cardiomyocytes are cultured (e.g., for about 5 days) and then infected with lentivirus bearing a genetically encoded optical reporter of electrical activity and optionally a light-gated ion channel.

Any suitable optical reporter of cellular activity may be used. Exemplary reporters include fluorescent reporters of transmembrane voltage differences, pHluorin-based reporters of synaptic vesicle fusion, and genetically encoded calcium indicators. In a preferred embodiment, a genetically encoded voltage indicator is used in combination with a spectrally distinct genetically encoded $Ca^{2+}$ indicator, preferably both encoded in a single vector to provide a fusion protein once transcribed and translated.

i. Voltage Reporters

An optical voltage reporter may be provided by a microbial rhodopsin or a modified microbial rhodopsin. A typical microbial rhodopsin is a light-driven proton pump structured as an integral membrane protein belonging to the family of archaeal rhodopsins. Archaeal rhodopsins are characterized by seven transmembrane helices with a retinal chromophore buried therein, the retinal chromophore being covalently bound to conserved lysine residue in one of the helices via a Schiff base. See Neutze et al., 2002, Bacteriorhodopsin: a high-resolution structural view of vectorial proton transport, Biochimica et Biophysica Acta 1565:144-167; Beja et al., 2001, Proteorhodopsin phototrophy in the ocean, Nature 411:786-789. The invention includes the insight that microbial rhodopsins or microbial rhodopsins modified to have reduced ion pumping activity—compared to the natural microbial rhodopsin protein from which they are derived—can be used as an optically detectable sensor to sense voltage across membranous structures, such as in cells and subcellular organelles when they are present in the lipid bilayer membrane. That is, the microbial rhodopsin proteins and the modified microbial rhodopsin proteins can be used as optical reporters to measure changes in membrane potential of a cell, including prokaryotic and eukaryotic cells. The optical reporters described herein are not constrained by the need for electrodes and permit electrophysiological studies to be performed in e.g., subcellular compartments (e.g., mitochondria) or in small cells (e.g., bacteria). The optical reporters described herein can be used in methods for drug screening, in research settings, and in in vivo imaging systems.

The retinal chromophore imbues microbial rhodopsins with unusual optical properties. The linear and nonlinear responses of the retinal are highly sensitive to interactions with the protein host: small changes in the electrostatic environment can lead to large changes in absorption spectrum. These electro-optical couplings provide the basis for voltage sensitivity in microbial rhodopsins.

Some of the microbial rhodopsins are derived from a microbial rhodopsin protein by modification of the protein to reduce or inhibit light-induced ion pumping of the rhodopsin protein. Such modifications permit the modified microbial rhodopsin proteins to sense voltage without altering the membrane potential of the cell with its native ion pumping activity. Other mutations impart other advantageous properties to microbial rhodopsin voltage sensors, including increased fluorescence brightness, improved photostability, tuning of the sensitivity and dynamic range of the voltage response, increased response speed, and tuning of the absorption and emission spectra.

Provided herein are illustrative exemplary optical voltage reporters and directions for making and using such sensors. Other sensors that work in a similar manner as optical reporters can be prepared and used based on the description and the examples provided herein.

Exemplary microbial rhodopsins include: green-absorbing proteorhodopsin (GPR, Gen Bank #AF349983), a light-driven proton pump found in marine bacteria; blue absorbing proteorhodopsin (BPR, GenBank # AF349981), a light-driven proton pump found in marine bacteria; Archaerhodopsin 3 (Arch3, GenBank # P96787); Algal bacteriorhodopsin (Ace, GenBank # AAY82897); Archaerhodopsin 1 (Arch 1, GenBank # P69051); Archaerhodopsin 2 (Arch 2, GenBank # P29563); and Archaerhodopsin 4 (Arch 4, GenBank # AAG42454). Some of the foregoing are pointed to by Genbank number. However, a rhodopsin may vary from a sequence in GenBank. Based on the description of the motif described herein, a skilled artisan will easily be able to make mutations to achieve the described or desired functions, e.g. reduction in the pumping activity of the microbial rhodopsin in question.

The invention includes the use of optical voltage reporters based on rhodopsins with introduced mutations. For example, mutations that eliminate pumping in microbial rhodopsins in the present invention generally comprise mutations to the Schiff base counterion; a carboxylic amino acid (Asp or Glu) conserved on the third transmembrane helix (helix C) of the rhodopsin proteins. Mutations to the carboxylic residue directly affect the proton conduction pathway, eliminating proton pumping (e.g., Asp to Asn, Gln, or His mutation, or Glu to Asn, Gln, or His mutation). Mutating the proton acceptor aspartic acid adjacent the Schiff base to asparagine suppresses proton pumping. Thus, in some embodiments, the mutations are selected from the group consisting of: D97N (green-absorbing proteorhodopsin), D95N (Archaerhodopsin 3), D99N (blue-absorbing proteorhodopsin), D75N (sensory rhodopsin II), and D85N (bacteriorhodopsin). Mutations of the aspartic acid to Gln or to His also serve to eliminate the photocurrent, for instance D95Q or D95H (Archaerhodopsin 3). For reference, some Archaerhodopsin sequences are shown in U.S. Pub. 2013/0224756, incorporated by reference for all purposes. In some embodiments, residues that can be mutated to inhibit pumping include (using bacteriorhodopsin numbering) D96, Y199, and R82, and their homologues in other microbial rhodopsins. In another embodiment, residue D95 can be mutated in Archaerhodopsin to inhibit proton pumping (e.g., D95N, D95H, or D95Q). Residues near the binding pocket can be mutated singly or in combination to tune the spectra to a desired absorption and emission wavelength. In bacteriorhodopsin these residues include, but are not limited to, L92, W86, W182, D212, I119, and M145. Homologous residues may be mutated in other microbial rhodopsins. Thus, in some embodiments, the mutation to modify the microbial rhodopsin protein is performed at a residue selected from the group consisting of L92, W86, W182, D212, I119, M145. Mutations can shift the dynamic range of voltage sensitivity into a desired band by shifting the distribution of charge in the vicinity of the Schiff base, and thereby changing the voltage needed to add or remove a proton from this group. Voltage-shifting mutations in green-absorbing proteorhodopsin include, but are not limited to, E108Q, E142Q, L217D, either singly or in combination using green-absorbing proteorhodopsin locations as an example, or a homologous residue in another rhodopsin. In one embodiment, a D95N mutation is introduced into Archaerhodopsin 3 to adjust the pKa of the Schiff base towards a neutral pH. Additionally or alternatively, mutations can enhance brightness, photostability, or both. Residues which, when mutated, may restrict conformational changes of the retinal within the binding pocket to increase fluorescence include (using bacteriorhodopsin numbering) Y199, Y57, P49, V213, and V48.

Optical voltage reporters that may be suitable for use with the invention include those that use the endogenous fluorescence of the microbial rhodopsin protein Archaerhodopsin 3 (Arch) from *Halorubum sodomense*. Arch resolves action potentials with high signal-to-noise ratio (SNR) and low photo-toxicity.

Figure 2:
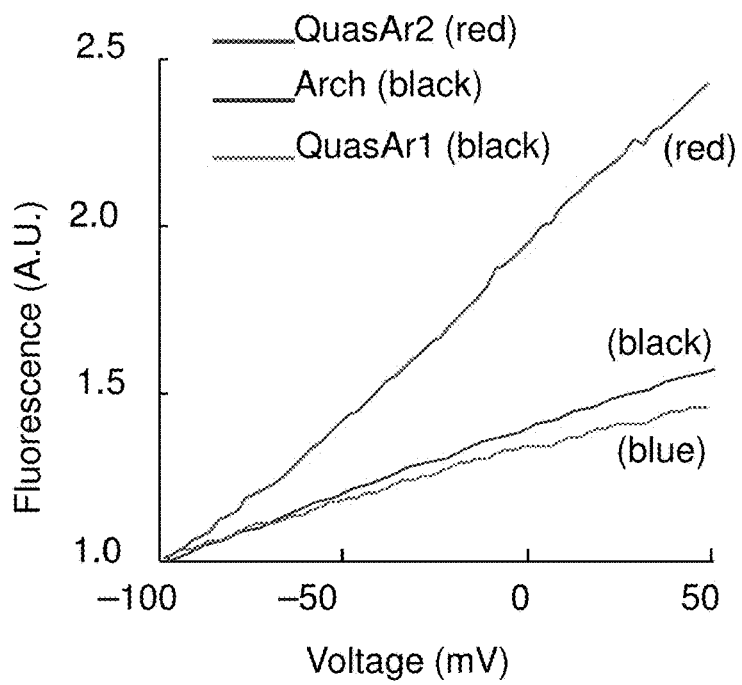
FIG. 2 shows the dependence of fluorescence on membrane voltage.

FIG. 2 shows the dependence of fluorescence on membrane voltage of Archaerhodopsin-based voltage indicators.

Figure 3:
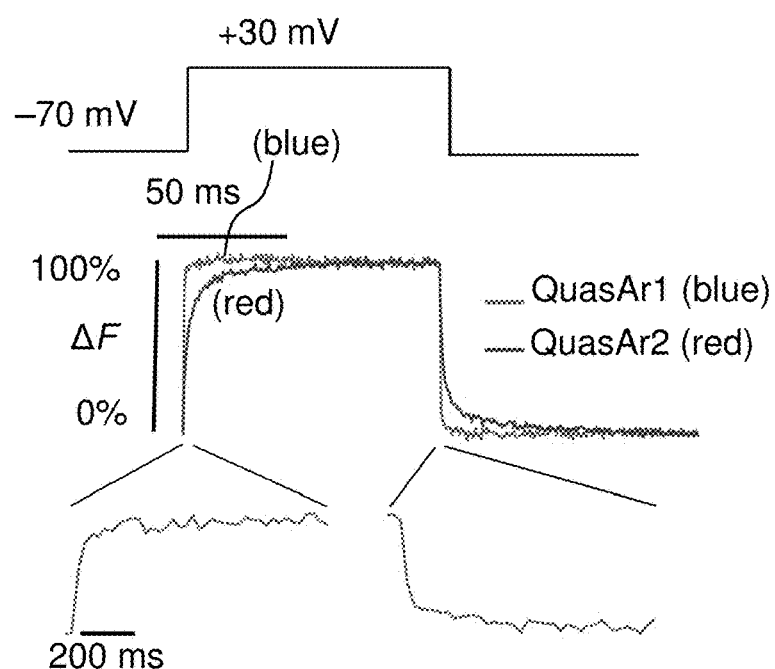
FIG. 3 shows the response of fluorescence to a step in membrane voltage.

FIG. 3 shows the response of fluorescence to a step in membrane voltage of Archaerhodopsin-based voltage indicators.

QuasAr2 refers to a specific variant of Arch. As discussed, archaerhodopsin 3 (Arch) functions as a fast and sensitive voltage indicator. Improved versions of Arch include the QuasArs ('quality superior to Arch'), described in Hochbaum et al., 2014. QuasAr1 differs from wild-type Arch by the mutations P60S, T80S, D95H, D106H and F161V. QuasAr2 differed from QuasAr1 by the mutation H95Q.

QuasAr1 and QuasAr2 report cardiomyocyte (CM) action potentials (APs).

Figure 4:
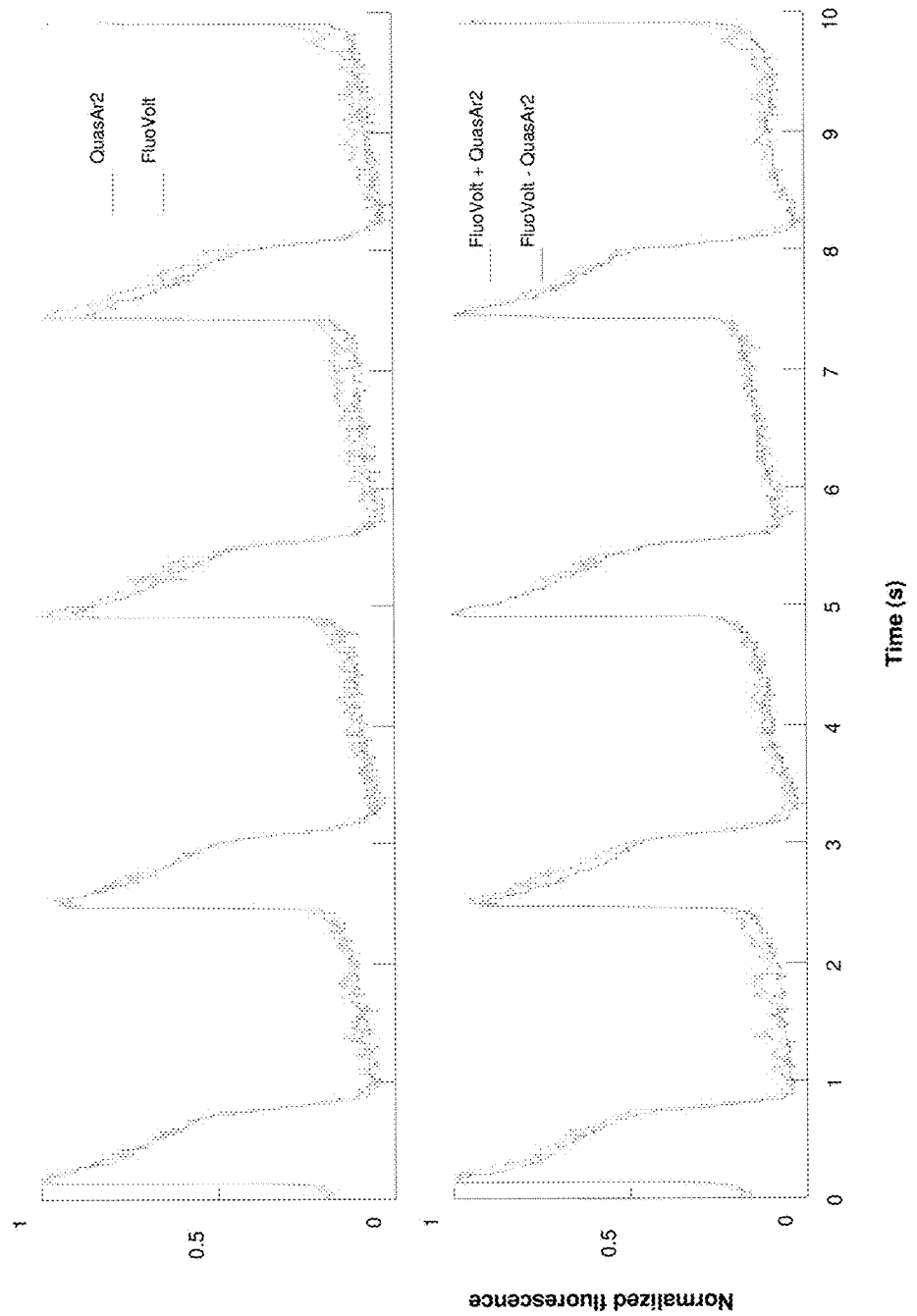
FIG. 4 shows action potential (AP) waveforms by QuasAr2 versus voltage-sensitive dye.

FIG. 4 shows action potential (AP) waveforms as measured by QuasAr2 compared to those measured using voltage-sensitive dye, such as FluoVolt. Cells are sparsely transfected with the QuasAr2 construct and then treated with FluoVolt dye. QuasAr2 is excited by red laser light at a wavelength of 635 nm with fluorescence detection centered at 720 nm. FluoVolt was excited by 488 nm laser light with fluorescence detection centered at 525 nm. The top panel shows the simultaneously recorded AP waveforms from a cell expressing QuasAr2 (red line) and labeled with FluoVolt (green line). The similarity of these traces establishes that QuasAr2 fluorescence accurately represents the underlying AP waveform. The lower trace compares the FluoVolt AP waveform in the presence (FluoVolt+, QuasAr2+, green) and absence (FluoVolt+, QuasAr2−, cyan) of QuasAr2 expression. The similarity of these two traces establishes that expression of QuasAr2 does not perturb the AP waveform.

Membrane potential is only one of several mechanisms of signaling within cells. One may correlate changes in membrane potential with changes in concentration of other species, such as $Ca^{2+}$, $H^+$ (i.e. pH), $Na^+$, ATP, cAMP, NADH. See FIG. 3. In some embodiments, systems and methods of the invention include or use an optical voltage reporter fused to another reporter such as a genetically encoded Ca++ indicator (GECI).

ii. GECIs

A fusion of an Arch-based voltage indicator and a genetically encoded $Ca^{2+}$ indicator (GECI) is called CaViar. See Hou et al. 2014, Simultaneous mapping of membrane voltage and calcium in zebrafish heart in vivo reveals chamber-specific developmental transitions in ionic currents, *Frontiers in physiology* 5, incorporated by reference. One can also use fusions with other protein-based fluorescent indicators to enable other forms of multimodal imaging using the concept as taught herein. Concentration of ions such as sodium, potassium, chloride, and calcium can be simultaneously measured when the nucleic acid encoding the microbial rhodopsin is operably linked to or fused with an additional fluorescent analyte sensitive indicator; or when the microbial rhodopsin and the additional fluorescent analyte sensitive indicator are co-expressed in the same cell.

A fusion of an Arch-based voltage indicator and a genetically encoded $Ca^{2+}$ indicator (GECI) is called CaViar. See Hou et al. 2014, Simultaneous mapping of membrane voltage and calcium in zebrafish heart in vivo reveals chamber-specific developmental transitions in ionic currents, *Frontiers in physiology* 5, incorporated by reference. One can also use fusions with other protein-based fluorescent indicators to enable other forms of multimodal imaging using the concept as taught herein. Concentration of ions such as sodium, potassium, chloride, and calcium can be simultaneously measured when the nucleic acid encoding the microbial rhodopsin is operably linked to or fused with an additional fluorescent analyte sensitive indicator; or when the microbial rhodopsin and the additional fluorescent analyte sensitive indicator are co-expressed in the same cell.

Genetically encoded calcium indicators (GECIs) (also called fluorescent calcium indicator proteins; FCIPs) may be delivered for expression in cardiomyocytes. GECIs are compatible with long-term, repeated in vivo measurements. GECIs typically include a calcium-binding domain. such as calmodulin or troponin C, fused to one or more (e.g., one, two, three, four, or more) fluorescent proteins (FPs). In single-FP GECIs, the fluorescence intensity of a circularly permuted FP (cpFP) is modulated by calcium binding-dependent changes in the chromophore environment. In two-FP GECIs, and multiple-FP GECIs, calcium binding modulates fluorescence resonance energy transfer (FRET) between FPs.

The calmodulin-based FRET indicator D3cpVenus (D3cpV) 13 may detect single APs. The troponin C-based indicator TN-XXL may be useful. Among single-FP based GECIs, the GCaMP family has found the broadest use across multiple model organisms. GCaMP is created from a fusion of green fluorescent protein (GFP), calmodulin, and M13, a peptide sequence from myosin light chain kinase. See Nakai et al., 2001, A high signal-to-noise Ca(2+) probe composed of a single fluorescent protein, Nature Biotechnol 19:137-141, incorporated by reference. GCaMP3 is a bright, stable GECI with large dynamic range and fast kinetics. In some embodiments, a GECI is GCaMP3 or a variant thereof. The sequences for GCaMP3 and variants may be found along with additional information in U.S. Pat. No. 8,629,256, incorporated by reference.

In some embodiments, the GECI includes a red-shifted Ca2+ indicator, such as the RGECO1 reporter (See Zhao et al., 2011, An expanded palette of genetically encoded Ca(2)+ indicators, Science 333:1888-1891, incorporated by reference.) In certain embodiments, a red-shifted is GECI is used. R-CaMP2 shows good sensitivity and speed, and an expanded dynamic range compared to other single-fluorophore GECIs (Inoue et al., 2015, Rational design of a high-affinity, fast, red calcium indicator R-CaMP2, Nat Methods 12:64-70, incorporated by reference). Other improved variants jRGECO1a, jRCaMP1a, and jRCaMP1b may be used. The jRCaMP1a, jRGECO1a and RCaMP2 are commercially available from Addgene and have been described in Dana et al., 2016, Sensitive red protein calcium indicators for imaging neural activity, bioRxiv, first published online Feb. 29, 2016, and available at biorxiv.org/content/biorxiv/early/2016/02/29/041780.full.pdf and incorporated by reference.

Figure 5:
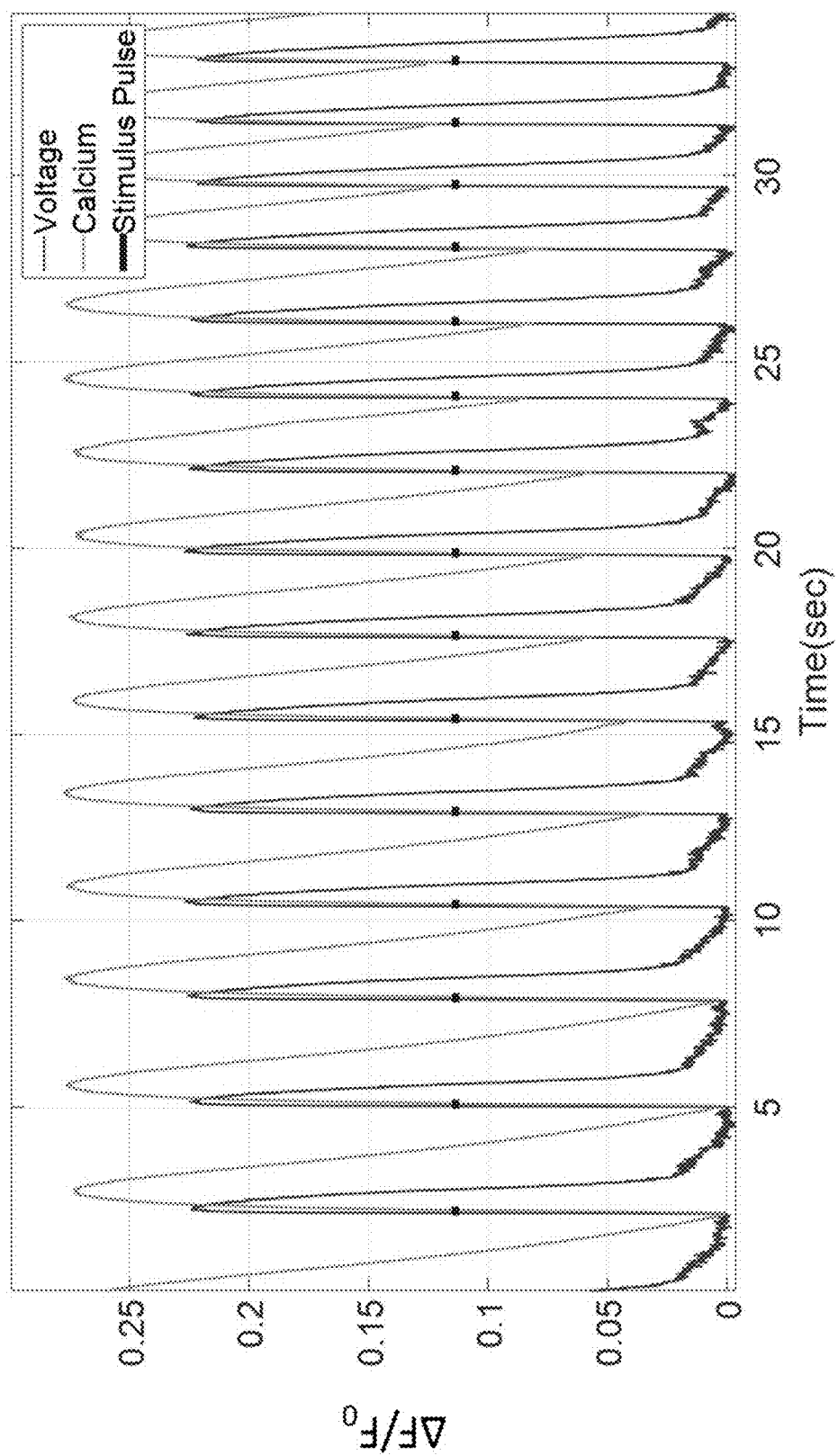

FIG. 5 shows simultaneous voltage and calcium recording during cardiomyocyte pacing with unpatterned cells. Human iPSC-derived cardiomyocytes (Takara) were co-transfected with CheRiff-eGFP (blue-stimulated channelrhodopsin), jRGECO1a (orange calcium sensor), and QuasAr2-dark mOrange2 (far-red voltage sensor) and plated homogeneously in the dish. In preferred embodiments, the GECI is a red-shifted calcium sensor such as jRGECO1a. Inward positive current, induced by 3 ms pulses of 448 nm blue LED excitation with a ramped frequency, provides cardiomyocyte pacing. This pacing allows well-controlled measurement of action potential shape properties in order to detect subtle drug-induced changes. A 556 nm LED is used to excite fluorescence from the jRGECO1a calcium reporter and a 635 nm laser is used to excite fluorescence from the QuasAr2 voltage reporter. Both reporters were simultaneously detected by a custom microscope with dual wavelength recording. Stimulation and recording occurred in the same field of view: optical cross talk is minimized, allowing the actuator and both sensors to work simultaneously. In FIG. 5, the periodic dots represent a pulse of stimulus (i.e., exposing CheRiff-eGFP to blue light); the taller, broader peaks in the figure are a waveform created with light received from the optical calcium reporter (i.e., the GCaMP variant jRGECO1a); and the shorter, narrower peaks are a waveform created by light received from the microbial rhodopsin QuasAr2-dark mOrange2. In the depicted embodiment, the microbial rhodopsin and the calcium reporter are preferably provided by a fusion protein so that they are present in a controlled ratio to one another (e.g., the same amount or one as an integer multiple of the other), which may aid meaningful comparison of signal strength and ensure that each cardiomyocyte with either has a suitable supply of the other so that both operate.

Thus FIG. 5 shows optogenetic assays for cardiomyocytes, in which the cardiomyocytes express an optogenetic reporter of membrane potential, an optogenetic reporter of calcium level, and an optogenetic actuator of electrical activity. The assay methods include receiving light from the optogenetic reporter of membrane potential and creating an AP waveform using the received light. Upon exposure to a compound, the AP waveform can be analyzed for perturbations that indicate a risk for arrhythmia associated with the compound. In the illustrated embodiment, the optogenetic reporter of membrane potential is a microbial rhodopsin (i.e., the Arch variant QuasAr2) and the optogenetic reporter of calcium level is at GECI (i.e., jRGECO1a), both co-expressed on a fusion protein. The cardiomyocyte are paced via the optogenetic actuator of electrical activity (here, the light-gated ion channel CheRiff).

Figure 6:
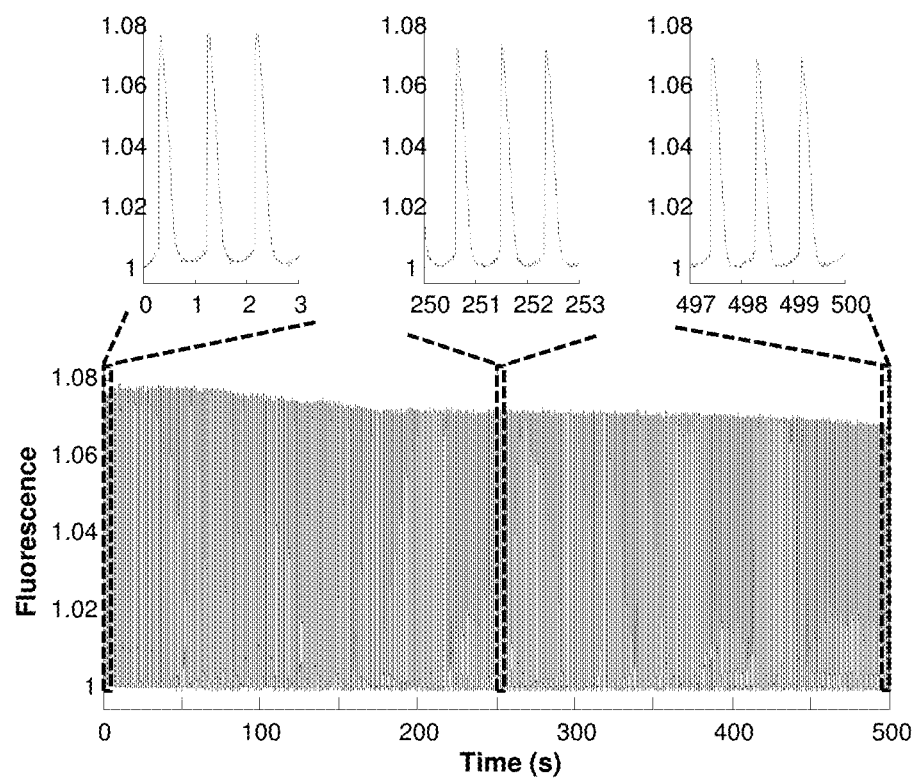
FIG. 6 presents phototoxicity and photobleaching measurement of QuasAr2.

FIG. 6 presents phototoxicity and photobleaching measurement of QuasAr2. Cells were imaged under continuous red laser illumination (~50 W/cm$^2$) for 500 s. Expanded views of the fluorescence recording are shown in the lower panels.

Figure 7:
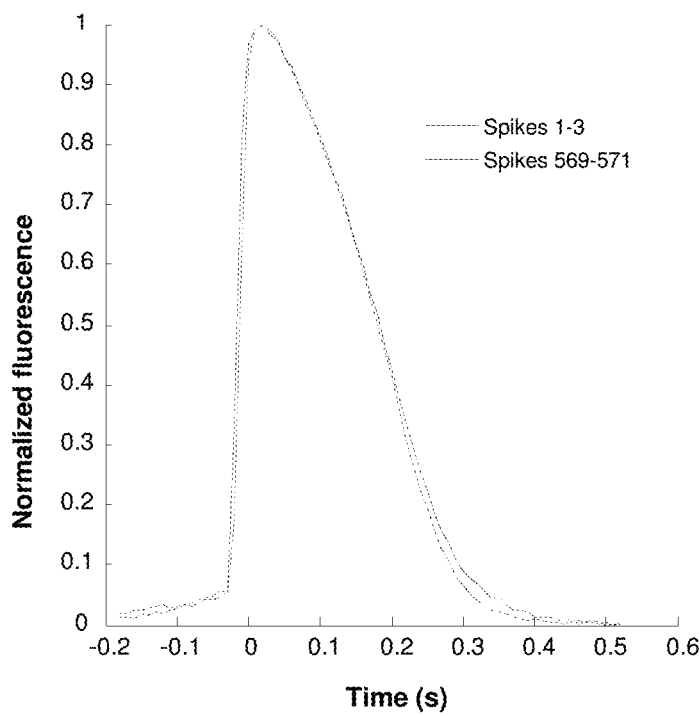
FIG. 7 graphs the average AP waveform shapes from FIG. 7.
Figure 8:
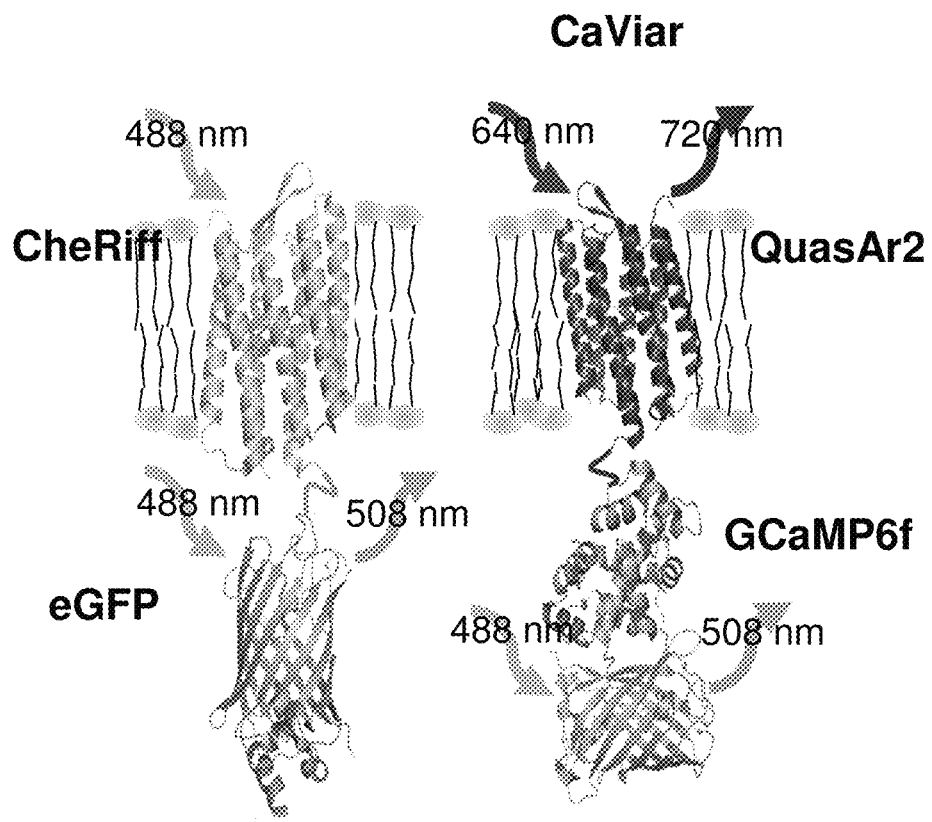
FIG. 8 shows structures of optogenetic proteins.

FIG. 7 graphs the average AP waveform shapes for the beginning (blue) and end (green) of the trace in FIG. 8.

The invention includes reporters based on Archaerhodopsin 3 (Arch 3) and its homologues. Arch 3 is Archaerhodopsin from *H. sodomense* and it is known as a genetically-encoded reagent for high-performance yellow/green-light neural silencing. Gene sequence at GenBank: GU045593.1 (synthetic construct Arch 3 gene, complete cds. Submitted Sep. 28, 2009). These proteins localize to the plasma membrane in eukaryotic cells and show voltage-dependent fluorescence.

Fluorescence recordings may be acquired on an epifluorescence microscope, described in Hochbaum et al., All-optical electrophysiology in mammalian neurons using engineered microbial rhodopsins, Nature Methods, 11, 825-833 (2014).

Optical reporters of the invention show high sensitivity. In mammalian cells, Archaerhodopsin-based reporters show about 3-fold increase in fluorescence between −150 mV and +150 mV. The response is linear over most of this range. Membrane voltage can be measured with a precision of <1 mV in a 1 s interval. Reporters of the invention show high speed. QuasAr1 shows 90% of its step response in 0.05 ms. The upstroke of a cardiac AP lasts approximately 1 ms, so the speeds of Arch-derived indicators meet the benchmark for imaging electrical activity. Reporters of the invention show high photo-stability and are comparable to GFP in the number of fluorescence photons produced prior to photobleaching. The reporters may also show far red spectrum. The Arch-derived voltage-indicating protein reporters, sometimes referred to as genetically encoded voltage indicators (GEVIs), may be excited with a laser at wavelengths between 590-640 nm, and the emission is in the near infrared, peaked at 710 nm. The emission is farther to the red than any other existing fluorescent protein. These wavelengths coincide with low cellular auto-fluorescence. This feature makes these proteins particularly useful in optical measurements of action potentials as the spectrum facilitates imaging with high signal-to-noise ratio, as well as multispectral imaging in combination with other fluorescent probes.

2b. Optogenetic Actuator

In a preferred embodiment, cells are transformed with an optical voltage actuator. This can occur, for example, simultaneously with or in parallel with transformation with the vector comprising the optogenetic reporter. The far-red excitation spectrum of certain Arch-based reporters suggests that they may be paired with a blue light-activated channelrhodopsin to achieve all-optical electrophysiology. For spatially precise optical excitation, the channelrhodopsin should carry current densities sufficient to induce action potentials (APs) when only a subsection of a cell is excited. Preferably, light used for imaging the reporter should not activate the actuator, and light used for activating the actuator should not confound the fluorescence signal of the reporter. Thus in a preferred embodiment, an optical actuator and an optical reporter are spectrally orthogonal to avoid crosstalk and allow for simultaneous use. Spectrally orthogonal systems are discussed in Carlson and Campbell, 2013, Circular permutated red fluorescent proteins and calcium ion indicators based on mCherry, Protein Eng Des Sel 26(12):763-772.

Preferably, a genetically-encoded optogenetic actuator is used. One actuator is channelrhodopsin2 H134R, an optogenetic actuator described in Nagel, G. et al., 2005, Light activation of channelrhodopsin-2 in excitable cells of *Caenorhabditis elegans* triggers rapid behavioral responses, Curr Biol 15:2279-2284.

A screen of plant genomes has identified an optogenetic actuator, *Scherffelia dubia* ChR (sdChR), derived from a fresh-water green alga first isolated from a small pond in Essex, England. See Klapoetke et al., 2014, Independent optical excitation of distinct neural populations, Nat. Meth. 11, 338-346 (2014); see also Melkonian & Preisig, 1986, A light and electron microscopic study of *Scherffelia dubia*, a new member of the scaly green flagellates (Prasinophyceae). Nord. J. Bot. 6:235-256, both incorporated by reference. SdChR may offer good sensitivity and a blue action spectrum.

An improved version of sdChR dubbed CheRiff may be used as an optical actuator. The gene for *Scherffelia dubia* Channelrhodopsin (sdChR) (selected from a screen of channelrhodopsins for its blue excitation peak (474 nm) and its large photocurrent relative to ChR2) is synthesized with mouse codon optimization, a trafficking sequence from Kir2.1 is added to improve trafficking, and the mutation E154A is introduced. CheRiff exhibits significantly decreased crosstalk from red illumination (to 10.5±2.8 pA) allowing its use in cells along with optogenetic reporters described herein. CheRiff shows good expression and membrane trafficking in cultured rat hippocampal neurons. The maximum photocurrent under saturating illumination (488 nm, 500 mW/cm$^2$) is 2.0±0.1 nA (n=10 neurons), approximately 2-fold larger than the peak photocurrents of ChR2 H134R or ChIEF (Lin et al., 2009, Characterization of engineered channelrhodopsin variants with improved properties and kinetics, Biophys J 96:1803-1814). In neurons expressing CheRiff, whole-cell illumination at only 22±10 mW/cm$^2$ induces a photocurrent of 1 nA compared to an illumination intensity of approximately 200 mW/cm$^2$ required for ChR2 H134R and ChIEF, At 23° C., CheRiff reaches peak photocurrent in 4.5±0.3 ms (n=10 cells). After a 5 ms illumination pulse, the channel closing time constant was comparable between CheRiff and ChIEF (16±0.8 ms, n=9 cells, and 15±2 ms, n=6 cells, respectively, p=0.94), and faster than ChR2 H134R (25±4 ms, n=6 cells, p<0.05). Under continuous illumination CheRiff partially desensitizes with a time constant of 400 ms, reaching a steady-state current of 1.3±0.08 nA (n=10 cells). Illumination of cells expressing CheRiff induces trains of APs with high reliability and high repetition-rate.

In some embodiments it is preferred to have an actuator whose activation is maximal at a violet light wavelength between 400-440 nm, further to the blue than CheRiff. Violet-activated channelrhodopsins can be simultaneously combined with Ca$^{2+}$ indicators (e.g. jRCaMP1a, jRGECO1a, and R-CaMP2) and a red-excited voltage indicator, e.g. QuasAr2, for simultaneous monitoring of Ca$^{2+}$ and voltage under optical pacing conditions.

A preferred violet-excited channelrhodopsin actuator is TsChR, derived from *Tetraselmis striata* (See Klapoetke et al., 2014, Independent optical excitation of distinct neural populations, Nat. Meth. 11, 338-346 (2014)). This channelrhodopsin actuator has a blue-shifted action spectrum with a peak at 435 nm. Another preferred violet channelrhodopsin actuator is PsChR, derived from *Platymonas subcordiformis* (see Govorunova, Elena G., et al. "Characterization of a highly efficient blue-shifted channelrhodopsin from the marine alga *Platymonas subcordiformis.*" *Journal of Biological Chemistry* 288.41 (2013): 29911-29922.). PsChr has a blue-shifted action spectrum with a peak at 437 nm. PsChR and TsChR are advantageously paired with red-shifted $Ca^{2+}$ indicators and can be used in the same cell or same field of view as these red-shifted $Ca^{2+}$ indicators without optical crosstalk.

2c. Vectors for Expression of Optogenetic Systems

The optogenetic reporters and actuators may be delivered in constructs described here as Optopatch constructs, CaViar, or both delivered through the use of an expression vector. Optopatch may be taken to refer to systems that perform functions traditionally associated with patch clamps, but via an optical input, readout, or both as provided for by, for example, an optical reporter or actuator. An Optopatch construct may include a bicistronic vector for co-expression of channelrhodopsin-eGFP and a reporter (e.g., a suitable Arch-based reporter such as QuasAr2). CaViar describes a system with reporters for both membrane potential and $[Ca^{2+}]$. The reporter and CheRiff constructs may be delivered separately, or a bicistronic expression vector may be used to obtain a uniform ratio of actuator to reporter expression levels.

The genetically encoded reporter, actuator, or both may be delivered by any suitable expression vector using methods known in the art. An expression vector is a specialized vector that contains the necessary regulatory regions needed for expression of a gene of interest in a host cell. Examples of vectors include plasmids (e.g. pBADTOPO, pCI-Neo, pcDNA3.0), cosmids, and viruses (such as a lentivirus, an adeno-associated virus, adenovirus, or a baculovirus).

In a preferred embodiment, about five days after plating, hiPSC-derived cardiomyocytes are transduced with lentiviral vectors. CaViar may be expressed in some wells, with CheRiff in other wells. Cells are left overnight in the viral medium at 37° C. in 5% $CO_2$. Virus is then removed from the cells and 1.5 mL of maintenance media added to each well. Viral delivery typically results in 8-10 expressing cells per field of view at 20× magnification.

In some embodiments the gene of interest is operably linked to another sequence in the vector. In some embodiments, it is preferred that the viral vectors are replication defective, which can be achieved for example by removing all viral nucleic acids that encode for replication. A replication defective viral vector will still retain its infective properties and enters the cells in a similar manner as a replicating vector, however once admitted to the cell a replication defective viral vector does not reproduce or multiply. The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

Many viral vectors or virus-associated vectors are known in the art. Such vectors can be used as carriers of a nucleic acid construct into the cell. Constructs may be integrated and packaged into non-replicating, defective viral genomes like Adenovirus, Adeno-associated virus (AAV), serotypes of AAV that include AAV1-AAV9, or Herpes simplex virus (HSV) or others, including retroviral and lentiviral vectors, for infection or transduction into cells.

Suitable delivery methods include viral and non-viral vectors, as well as biological or chemical methods of transfection. The methods can yield either stable or transient gene expression in the system used. In some embodiments, a viral vector such as an (i) adenovirus, (ii) adeno-associated virus, (iii) retrovirus, (iv) lentivirus, or (v) other is used. Viral vectors suitable for use with the invention are discussed in greater detail in U.S. Pub. 2014/0295413, the contents of which are incorporated by reference in their entirety.

In certain embodiments, genetic material is delivered by a non-viral method. Non-viral methods include plasmid transfer, electroporation, modified RNA, and the application of targeted gene integration through the use of integrase or transposase technologies. Exemplary recombinase systems include: cre recombinase from phage P1 (Lakso et al., 1992, Targeted oncogene activation by site-specific recombination in transgenic mice, PNAS 89:6232-6236; Orban et al., 1992, Tissue- and site-specific DNA recombination in transgenic mice, PNAS 89:6861-6865), FLP (flippase) from yeast 2 micron plasmid (Dymecki, 1998, Using Flp-recombinase to characterize expansion of Wnt1-expressing neural progenitors in the mouse, Dev Biol 201:57-65), and an integrase isolated from streptomyses phage I C31 (Groth et al., 2000, A phage integrase directs efficient site-specific integration in human cells, PNAS 97(11):5995-6000). Each of these recombinases recognizes specific target integration sites. Cre and FLP recombinase catalyze integration at a 34 bp palindromic sequence called lox P (locus for crossover) and FRT (FLP recombinase target) respectively. Phage integrase catalyzes site-specific, unidirectional recombination between two short att recognition sites in mammalian genomes. Recombination results in integration when the att sites are present on two different DNA molecules and deletion or inversion when the att sites are on the same molecule. It has been found to function in tissue culture cells (in vitro) as well as in mice (in vivo).

In certain embodiments, actuators, reporters, or other genetic material may be delivered using chemically-modified mRNA. It may be found and exploited that certain nucleotide modifications interfere with interactions between mRNA and toll-like receptor, retinoid-inducible gene, or both. Exposure to mRNAs coding for the desired product may lead to a desired level of expression of the product in the cells. See, e.g., Kormann et al., 2011, Expression of therapeutic proteins after delivery of chemically modified mRNA in mice, Nat Biotech 29(2):154-7; Zangi et al., 2013, Modified mRNA directs the fate of heart progenitor cells and induces vascular regeneration after myocardial infarction, Nat Biotech 31:898-907.

It may be beneficial to culture or mature the cells after transformation with the genetically encoded optical reporter with optional actuator. In some embodiments, the cardiomyocytes are matured for 5-10 days post infection. Using microscopy and analytical methods described herein, the cell and its action potentials may be observed. For additional discussion, see U.S. Pub. 2013/0224756, incorporated by reference in its entirety for all purposes.

Other methods for transfection include physical methods such as electroporation as well as methods that employ biomolecules, liposomes, etc. Such methods are discussed in greater detail in U.S. Pub. 2014/0295413, the contents of which are incorporated by reference in their entirety.

As discussed above, the invention includes optogenetic reporters, optogenetic actuators, and vectors for the expression of microbial rhodopsins. See also U.S. Pat. No. 8,716,447 to Deisseroth; U.S. Pat. No. 8,647,870 to Hegemann; U.S. Pat. No. 8,617,876 to Farrar; U.S. Pat. No. 8,603,790 to Deisseroth; U.S. Pat. No. 8,580,937 to Spudich; U.S. Pat. No. 8,562,658 to Shoham; and U.S. Pat. No. 8,202,699 to Hegemann, the contents of each of which are incorporated by reference.

Using such vectors with the optogenetic systems, the invention can thus be used to provide cells or cell cultures. For example, methods of the invention can be used to provide a cell with a eukaryotic genome that expresses a voltage-indicating microbial rhodopsin and a light-gated ion channel such as an algal channel rhodopsin as described herein. The cell may be a cardiomyocyte, neuron, or other electrically-active cell. The microbial rhodopsin may provide an optical reporter of membrane electrical potential such as QuasAr1 or QuasAr2. Preferably the cell also expresses a GECI such as jRCaMP1a, jRGECO1a, or RCaMP2. In some embodiments, the light-gated ion channel comprises a blue-shifted actuator with an excitation maximum at a wavelength <450 nm and the protein that reports the change in the intracellular calcium level comprises a red-shifted calcium indicator with an excitation maximum between 520 nm and 570 nm inclusive. The light-gated ion channel can include a blue-shifted actuator such as TsChR or PsChR. In preferred embodiments, the microbial rhodopsin, the light-gated ion channel, or both are expressed from a gene that is integrated into the metazoan genome. Additionally or alternatively, methods of the invention can be used to provide a cell culture that includes a first plurality of animal cells expressing an optogenetic actuator and a second plurality of animal cells, electrically contiguous with the first plurality of animal cells, expressing a genetically-encoded optical reporter of activity.

3. Optical Pacing with Optical Readout

Materials and methods described herein may be used to pace cardiomyocytes as well as measure membrane voltage and intracellular Ca2+ of cardiomyocytes. In a cardiomyocyte sample, pacing, voltage measurement, and Ca2+ measurement may be performed simultaneously by spatially segregating CheRiff expressing cardiomyocytes from CaViar expressing cardiomyocytes; by using patterned illumination to selectively illuminate particular cells in a mixed culture, or by using spectrally orthogonal optogenetic constructs (e.g., TsChR for Pacing; a QuasAr for voltage measurement, and RGECO1 for calcium measurement).

FIG. 8 presents schematic structures of optogenetic proteins used for pacing and detection of voltage and intracellular Ca2+. The diagrams show proteins homologous to CheRiff and QuasAr2. Pacing of CMs is achieved through pulsed 488 nm LED illumination of CheRiff. The CheRiff construct is coupled to an eGFP tag for detection of CheRiff expression. A fusion protein called CaViar (Hou et al., 2014), consisting of QuasAr2 (Hochbaum et al., 2014) fused to a GECI such as GCaMP6f may be used for simultaneous voltage and $Ca^{2+}$ imaging. QuasAr2 is excited via red laser light. GCaMP6f is excited via blue laser light. Cells are separately transduced with either CheRiff or CaViar vectors.

In human iPSC-derived cultures, cells may beat spontaneously. However, if not paced according to methods herein, the beat rate may vary significantly with state of maturation, from dish to dish, and upon pharmacological or environmental perturbation. Uncontrolled beat rate variation presents an undesirable source of noise in cell-based assays.

Mature ventricular cardiomyocytes do not beat spontaneously. As iPSC-based cultures become more mature, there may be a need to pace these cells to have any beating at all. Furthermore, in studies on primary adult ventricular myocytes (e.g. from rodents, rabbits, dogs, or pigs), it is necessary to supply an exogenous pacing signal.

Traditionally, cardiomyocytes were paced with field-stimulation electrodes. Physical electrodes generate electrochemical byproducts which gradually foul the solution and are thus incompatible with long-term measurements. Physical electrodes also present a challenge for maintaining sterility, a requirement for chronic or long-term measurements.

Expression of channelrhodopsin-based light-gated ion channels provides a means to achieve optical pacing. However, the blue light used to activate these channels may overlap spectrally with the light used to image most small-molecule and genetically encoded fluorescent reporters of physiological activity (e.g. gCaMP $Ca^{2+}$ indicators, Percival ATP indicators, pHluorin pH indicators, VF2.1.Cl voltage-sensitive dyes). Also, the light used to image these reporters may lead to off-target activation of all known channelrhodopsin actuators. Ideally, one would like to optically pace a cardiac culture while maintaining freedom to record from fluorescent reporters of any color, without optical crosstalk between the pacing and the physiological measurement. Methods of the invention allow a cardiac culture to be optically paced while also using fluorescent reporters of any color, without optical crosstalk between the pacing and the physiological measurement through the spatial separation of pacemaker cells and reporter cells.

One solution presented here comprises expressing channelrhodopsin actuators in one set of hiPSC-derived cardiomyocytes, and expressing reporters (e.g. CaViar dual-function $Ca^{2+}$ and voltage reporter) in another set of reporters. Flashes of blue light are delivered to the actuator cells, while continuous blue light is used to monitor the reporter cells. The actuator cells pace the reporter cells through gap junction-mediated in-plane conduction. This approach is the most physiologically relevant pacing mechanism, as this is how cardiac signals propagate in the heart. The key challenge is to identify and target the pacing and the measurement light beams to the appropriate corresponding cells. Methods of the invention provide at least two embodiments of the solution to the problem of targeting separate pacing and measurement light beams to the appropriate cells: a first approach based on spatial segregation and a second approach based on image processing and patterned illumination.

3a. Spatial Segregation

Embodiments of the invention provide for spatial separation of pacemaker cells and reporter cells. Many aspects of cardiac physiology are beat-rate dependent. Action potential waveform, calcium levels, pH, ATP levels, and mitochondrial function depend, not just on current beat rate, but also on recent history of beat rate. In many cardiac diseases arrhythmias develop only under certain pacing conditions (e.g. exercise, surprise, or sleep). To accurately predict cardiotoxicity and to study the mechanisms of cardiac arrhythmias, it is essential to pace cells in well-defined temporal patterns using methods described herein.

Figure 9:
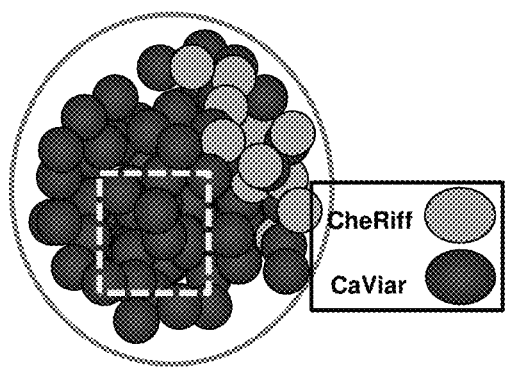
FIG. 9 illustrates a cardiomyocyte plating configuration for spatial segregation.

FIG. 9 illustrates a cardiomyocyte plating configuration for spatial segregation. For simultaneous optical pacing and imaging of both $Ca^{2+}$ and membrane voltage, cells may be plated to spatially segregate CheRiff-expressing cells from CaViar-expressing cells to avoid optical crosstalk between the pulsed blue light used to periodically stimulate the CheRiff-expressing cells and the continuous blue light used to image the CaViar-expressing cells. The CheRiff-expressing cells lay outside the imaging region. Light is targeted to the pacing cells using spatial segregation of actuator and reporter-expressing cells.

Cells are independently infected with actuator and reporter and are re-plated in distinct but electrically contiguous regions. Optical stimulus is delivered only to regions of the dish with cells expressing the actuator, and sensor measurements using any wavelength of light are recorded in regions of the dish away from cells expressing the actuator. In one instance, the actuator is CheRiff, and the sensor is CaViar in human iPSC-derived cardiomyocytes.

Figure 10:
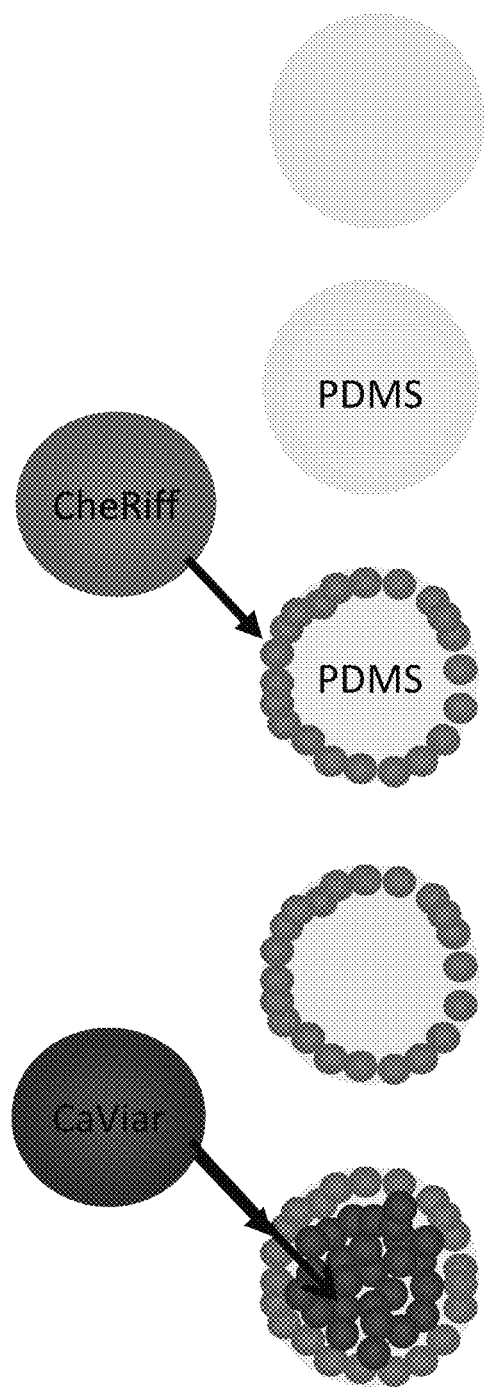
FIG. 10 shows cells expressing CheRiff plated in an annular region.

FIG. 10 shows an alternative embodiment in which cells expressing CheRiff plated in an annular region, 10 mm outer diameter, ~8 mm diameter. The inner radius is set by a disk of polydimethyl siloxane (PDMS) adhered to the coverslip and the outer diameter is set by the edge of the chamber. The PDMS disk is then removed and cells expressing CaViar are plated throughout. Pacing is controlled by a blue LED whose illumination is confined to a small region of the actuating cells. Voltage and calcium imaging are achieved with a red and blue laser, respectively, in a region free of CheRiff-expressing cells.

Figure 11:
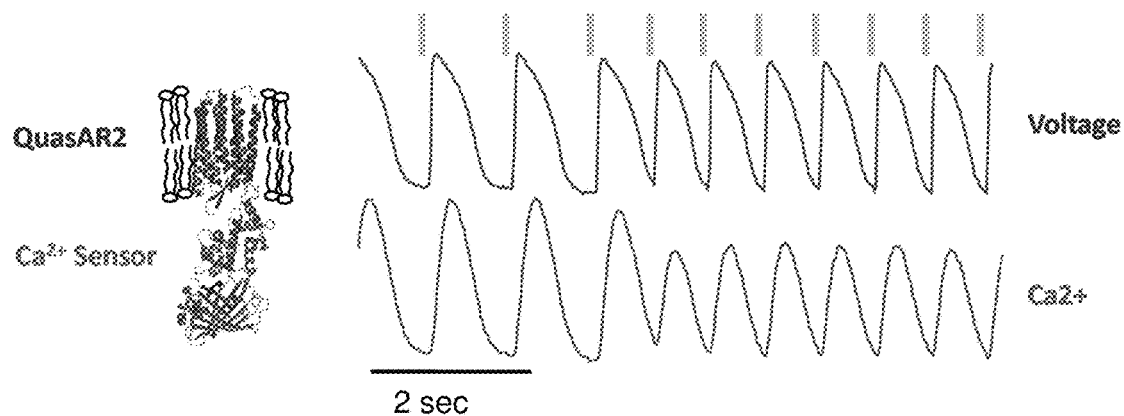
FIG. 11 shows examples of calcium and voltage traces from a cell expressing CaViar.

FIG. 11 shows examples of calcium and voltage traces from a cell expression a joint $Ca^{2+}$ and voltage indicator (CaViar), paced via gap junction-mediated conduction from a cell expressing the CheRiff optogenetic actuator. This sample was prepared via the spatial segregation approach.

3b. Patterned Illumination

In a second embodiment using patterned illumination, light is targeted to the pacing cells using image processing and patterned illumination to separately target intermingled actuator- and reporter-expressing cells.

For image processing and patterned illumination, cells expressing either actuator or reporters are randomly intermixed. The cells are then lifted from their respective dishes, mixed, and co-plated onto the imaging dish. In another embodiment, cells are plated directly in the imaging chamber, and doubly infected with lentivirus encoding Cre-On actuator and a Cre-Off reporter. The cells are then infected sparsely with lentivirus encoding the Cre protein, so that in a sparse subset of cells the actuator is switched on and the reporter is switched off.

Figure 12:
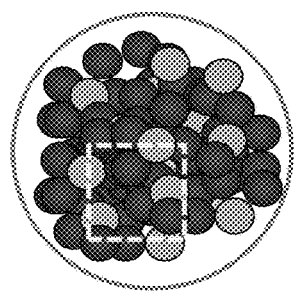
FIG. 12 shows cardiomyocytes that express either an actuator or a reporter.

FIG. 12 shows cardiomyocytes initially plated separately and caused to express either the actuator or the reporter. For simultaneous optical pacing and voltage imaging, CheRiff cells (solid lighter circles) were co-mingled with CaViar cells (solid darker circles). The yellow dotted line indicates a microscope field of view.

Cells expressing the actuator are identified via a recognizable marker, e.g. a fluorescent protein, or by their absence of fluorescence transients indicating presence of a reporter. Optical pacing is achieved by spatially patterning the excitation light using a digital micromirror device (DMD) to project pacing flashes onto only those cells expressing the actuator.

Figure 13:
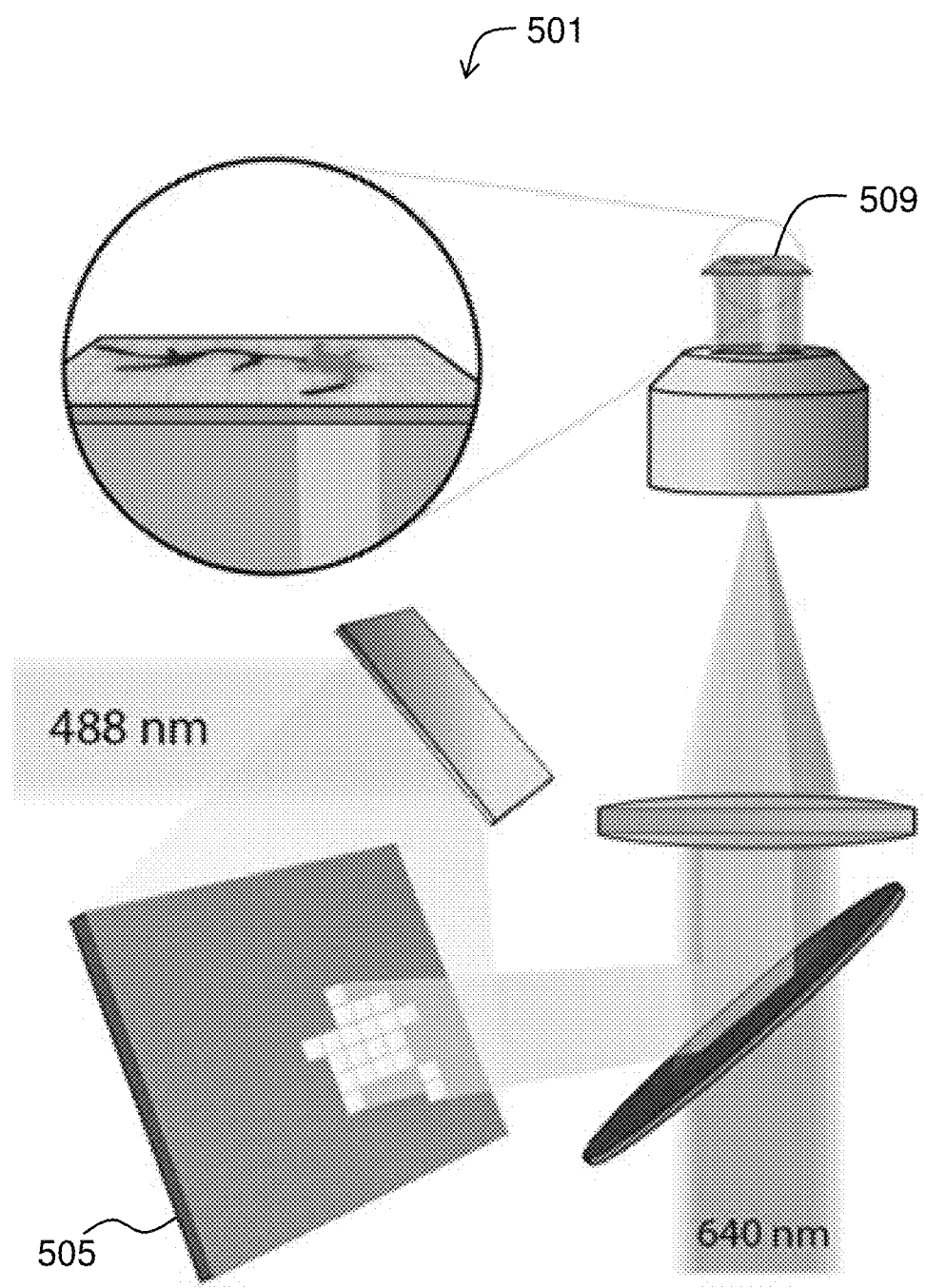
FIG. 13 shows components of an optical imaging apparatus

FIG. 13 gives a functional diagram of components of an optical imaging apparatus 501 according to certain embodiments. A 488 nm blue laser beam is modulated in intensity by an acousto-optic modulator (not shown), and then reflected off a digital micromirror device (DMD) 505. The DMD imparted a spatial pattern on the blue laser beam (used for CheRiff excitation) on its way into the microscope. The micromirrors were re-imaged onto the sample 509, leading to an arbitrary user-defined spatiotemporal pattern of illumination at the sample. Simultaneous whole-field illumination with 640 nm red light excites fluorescence of the reporter.

With the inverted fluorescence microscope, illumination from a blue laser 488 nm 50 mW (Omicron PhoxX) is sent through an acousto-optic modulator (AOM; Gooch and Housego 48058-2.5-0.55-5W) for rapid control over the blue intensity. The beam is then expanded and modulated by DMD 505 with 608×684 pixels (Texas Instruments LightCrafter). The DMD is controlled via custom software (Matlab) through a TCP/IP protocol. The DMD chip is re-imaged through the objective onto the sample, with the blue and red beams merging via a dichroic mirror. Each pixel of the DMD corresponds to 0.65 µm in the sample plane. A 532 nm laser is combined with the red and blue beams for imaging of mOrange2. Software is written to map DMD coordinates to camera coordinates, enabling precise optical targeting of any point in the sample.

To achieve precise optical stimulation of cardiomyocytes, pixels on DMD 505 are mapped to pixels on the camera. The DMD projects an array of dots of known dimensions onto the sample. The camera acquires an image of the fluorescence. Custom software locates the centers of the dots in the image, and creates an affine transformation to map DMD coordinates onto camera pixel coordinates.

A dual-band dichroic filter (Chroma zt532/635rpc) separates reporter (e.g., Arch) from excitation light. A 531/40 nm bandpass filter (Semrock FF01-531/40-25) may be used for eGFP imaging; a 710/100 nm bandpass filter (Chroma, HHQ710/100) for Arch imaging; and a quad-band emission filter (Chroma ZET405/488/532/642m) for mOrange2 imaging and pre-measurement calibrations. A variable-zoom camera lens (Sigma 18-200 mm f/3.5-6.3 II DC) is used to image the sample onto an EMCCD camera (Andor iXon+ DU-860), with 128×128 pixels. Images may be first acquired at full resolution (128×128 pixels). Data is then acquired with 2×2 pixel binning to achieve a frame rate of 1,000 frames/s. For runs with infrequent stimulation (once every 5 s), the red illumination is only on from 1 s before stimulation to 50 ms after stimulation to minimize photobleaching. Cumulative red light exposure may be limited to <5 min. per cardiomyocyte.

Low magnification wide-field imaging is performed with a custom microscope system based around a 2×, NA 0.5 objective (Olympus MVX-2). Illumination is provided by six lasers 640 nm, 500 mW (Dragon Lasers 635M500), combined in three groups of two. Illumination is coupled into the sample using a custom fused silica prism, without passing through the objective. Fluorescence is collected by the objective, passed through an emission filter, and imaged onto a scientific CMOS camera (Hamamatsu Orca Flash 4.0). Blue illumination for channelrhodopsin stimulation is provided by a 473 nm, 1 W laser (Dragon Lasers), modulated in intensity by an AOM and spatially by a DMD (Digital Light Innovations DLi4130-ALP HS). The DMD is re-imaged onto the sample via the 2× objective. During a run, cardiomyocytes may be imaged using wide-field illumination at 488 nm and eGFP fluorescence. A user may select regions of interest on the image of the neuron, and specify a time course for the illumination in each region. The software maps the user-selected pixels onto DMD coordinates and delivers the illumination instructions to the DMD. The fluorescent protein serving as a recognizable marker of the cells expressing the actuator is imaged to determine a pattern of those actuator cells. The digital coordinates of that image are used to control the DMD 505 so that the DMD 505 directs the blue 488 nm light only onto the actuator cells. Due to the precision of the patterned illumination provided by the DMD 505, the cells expressing the reporter are not exposed to the 488 nm light. Cells expressing the reporter are imaged under continuous illumination, with the 640 nm light targeted via the DMD to illuminate only those cells expressing the reporter, and optionally continuous illumination at a wavelength of 488 nm to illuminate an additional reporter such as a GCaMP calcium indicator.

By the patterned illumination method, flashes of blue light are delivered to the actuator cells, while continuous red and/or blue light is used to monitor the reporter cells. The actuator cells pace the reporter cells through gap junction-mediated in-plane conduction. Preferably, the actuator cells comprise a first set of cardiomyocytes expressing channelrhodopsin actuators and the reporter cells comprise a second set of cardiomyocytes expressing reporters (e.g. QuasAr2 or CaViar dual-function $Ca^{2+}$ and voltage reporter).

3c. Simultaneous Pacing, Voltage and Ca2+ Measurement.

Simultaneous optical stimulation of cardiomyocytes with calcium and voltage imaging may be achieved without spatial segregation using spectrally orthogonal proteins. In some embodiments, to achieve all three modalities in the same cell, the invention provides for a violet-excited Channelrhodopsin actuator (psChR or TsChR); a red-shifted genetically encoded calcium indicator; and a far red Arch-derived voltage indicator. Suitable GECIs include jrGECO1a, jrCaMP1a, and RCaMP2. See Zhao et al., 2011, An expanded palette of genetically encoded $Ca^{2+}$ indicators, *Science* 333(6051):1888-1891; Wu et al., 2013, Improved orange and red $Ca^{2+}$ indicators and photophysical considerations for optogenetic applications, *ACS chem neurosci* 4:963-972; Inoue et al., 2015, Rational design of a high-affinity, fast, red calcium indicator R-CaMP2, *Nature methods* 12:64-70, each incorporated by reference. In particular, jRCaMP1a may be obtained as Addgene plasmid 61562 and jRGECO1a may be obtained as Addgene plasmid 61563. Such GECIs are excited by wavelengths between 540 and 560 nm, and emit at wavelengths between 570 and 620 nm, thereby permitting spectral separation from the violet-excited channelrhodopsin actuator and the Arch-based voltage indicator. By these means, one may simultaneously pace cardiomyocytes, measure voltage, and measure calcium without spatial segregation or light patterning.

4. Preparation of Plates for Voltage Imaging with Pacing Via Separate Expression and Co-Plating MatTek dishes (MatTek corp.; 10 mm glass diameter, #1.5) are coated with 10 μg/mL fibronectin (Sigma-Aldrich) in 0.1% gelatin overnight at 4° C. Cardiomyocytes expressing CaViar and CheRiff are trypsinized according to the manufacturer's protocol (CDI). Trypsinized CaViar and CheRiff-expressing cells are first mixed at a ratio of 5:1 CaViar:CheRiff, and then pelleted. The combined cells are re-suspended in 2.1 mL of maintenance medium and plated at a density of $2.5 \times 10^4$ cells/cm$^2$ in 100 μL of plating medium to cover the entire glass surface. Cells were kept at 37° C. in 5% $CO_2$ overnight to adhere to the glass. Maintenance medium (1.0 mL) was added to each dish and the cells were fed every 48 hours by removing 750 μL of medium from the dish and replacing with 750 μL fresh maintenance medium.

Preparation of Plates for Simultaneous Voltage and Calcium Imaging with Pacing

For simultaneous voltage and calcium imaging, MatTek dishes (10 mm glass diameter) are prepared to segregate CheRiff-expressing cells from CaViar-expressing cells (e.g., according to one of the methods described above). This allows simultaneous calcium imaging and CheRiff pacing, both with blue light, without optical crosstalk between the two functions. In certain embodiments, 8 mm-diameter poly-dimethylsiloxane (PDMS) discs are treated with a solution of 10 μg/mL fibronectin in 0.1% gelatin on one side for 10 minutes at room temperature. The coated discs are then dried and then pressed onto the MatTek dish glass surface, slightly offset to one side. The remaining exposed area of the glass is then coated with 10 μg/mL fibronectin in 0.1% gelatin. Cells expressing the CheRiff are trypsinized according to the manufacturer's protocol and re-suspended in 50 μL of maintenance medium per dish. For plating, 50 μL of the CheRiff cells are then added to the exposed portion of the glass surface and allowed to sit for 40 minutes at 37° C. in 5% $CO_2$ to allow the cells to adhere. The PDMS discs are then removed, the glass surface washed with 150 μL of maintenance media medium and the remaining volume aspirated. Trypsinized CaViar cells are then re-suspended in 100 μL of maintenance medium per dish and plated at a density of $2.0 \times 10^4$ cells/cm$^2$ in 100 μL to cover the entire glass surface. Cells are kept at 37° C. in 5% $CO_2$ overnight to adhere to the glass. 1.0 0 mL of maintenance medium is added to each dish and the cells were fed every 48 hours by removing 750 μL of media from the dish and adding 750 μL fresh maintenance medium.

5. Imaging Activity Assay

Methods of the invention may include pacing cardiomyocytes with a light source (e.g., by optical stimulation of an optical actuator or stimulating an upstream cell in gap junction-mediated communication with the cell(s) to be observed). The reporters (e.g., QuasAr and GECI) are also excited with a light source so that the emitted fluorescence can be detected. The wavelength of the excitation light depends on the fluorescent molecule. For example, a voltage-reporter such as an Archaerhodopsin may be excited using a second light source with wavelengths varying between lambda=594 nm and lambda=645 nm. Alternatively, the range may be between lambda=630-645 nm.

A calcium reporter may be excited using a third light source. For example, if the cell expresses a GECI, a second wavelength preferably differs from the first wavelength. Examples of useful wavelengths include wavelengths in the range of lambda=447-594 nm, for example, lambda=473 nm, lambda=488 nm, lambda=514 nm, lambda=532 nm, and lambda=561 nm.

Methods of the invention allow for the measurement of action potentials with sub-millisecond temporal resolution. A cell expressing an Optopatch construct may be exposed to whole-field illumination with pulses of blue light (10 ms, 25 mW/cm$^2$) to stimulate CheRiff, and simultaneous constant illumination with red light (800 W/cm$^2$) to excite fluorescence of the reporter (e.g., QuasAr1 or QuasAr2 or a suitable variant thereof). The fluorescence of the reporter may be imaged at a 1 kHz frame rate. Key parameters include temporal precision with which single spikes can be elicited and recorded, signal-to-noise ratio (SNR) in fluorescence traces, and long-term stability of the reporter signal. Methods provided herein may be found to optimize those parameters.

In some embodiments, measurements are made using a low-magnification microscope that images a 1.2×3.3 mm field of view with 3.25 μm spatial resolution and 2 ms temporal resolution. In other embodiments, measurements are made using a high-magnification microscope that images a 100 μm field of view with 0.8 μm spatial resolution and 1 ms temporal resolution. A suitable instrument is an inverted fluorescence microscope, similar to the one described in the Supplementary Material to Kralj et al., 2012, Optical recording of action potentials in mammalian neurons using a microbial rhodopsin, Nat. Methods 9:90-95. Briefly, illumination from a red laser 640 nm, 140 mW (Coherent Obis 637-140 LX), is expanded and focused onto the back-focal plane of a 60× oil immersion objective, numerical aperture 1.45 (Olympus 1-U2B616).

Figure 14:
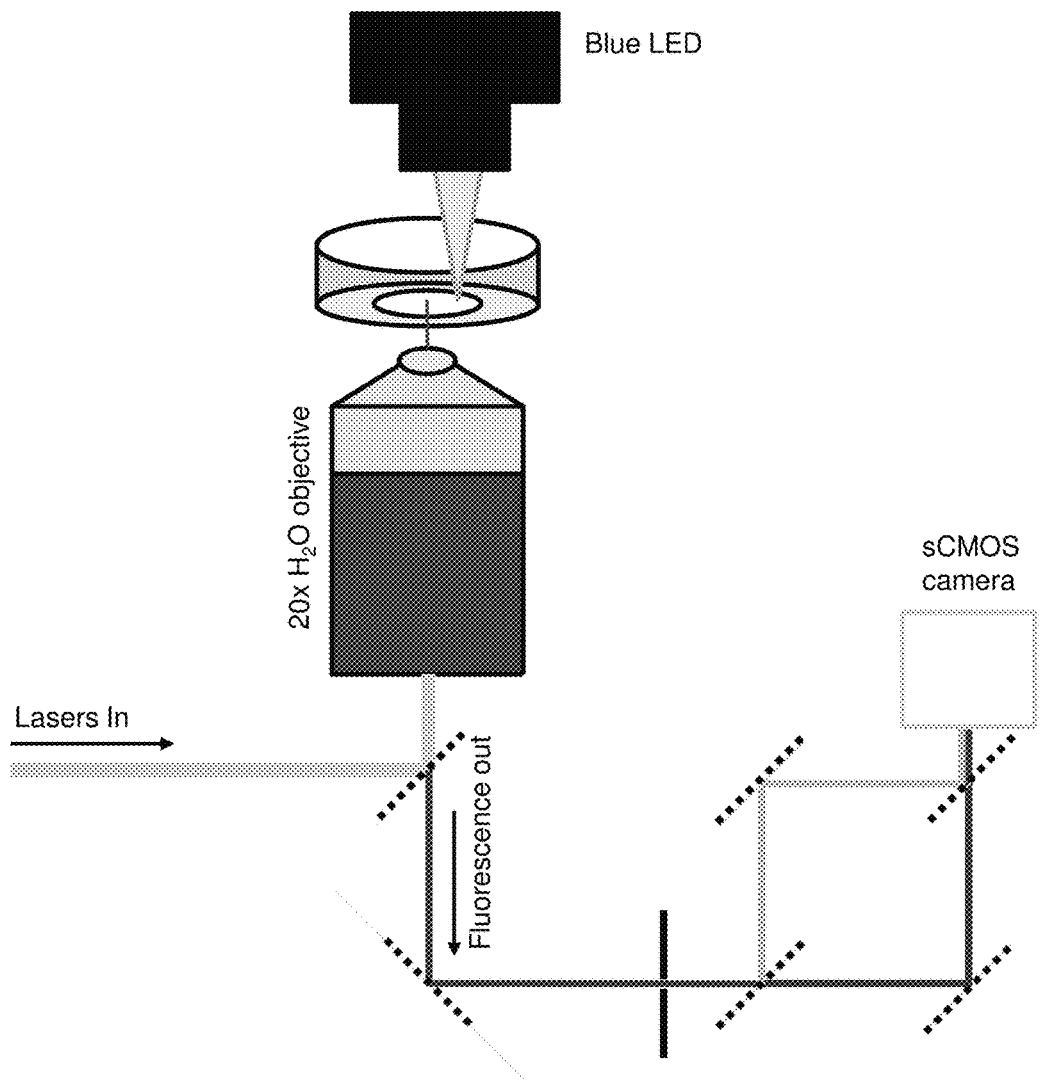
FIG. 14 shows an instrument for Optopatch measurements for cardiomyocytes.

FIG. 14 shows a schematic of custom instrument for Optopatch measurements as applicable to imaging paced cardiomyocytes. Red (635 nm) and/or blue (488 nm) laser light is directed towards the sample ("Lasers in") through a 20×, NA 1.0 water-immersion objective in an epifluorescence format. Fluorescence is collected by the same objective and passed through a dichroic mirror. A home-built dual view detection scheme is used to image each fluorescent band (split and re-joined in path to sCMOS camera) onto adjacent halves of a scientific CMOS (sCMOS) camera. The described schematic allows simultaneous detection of QuasAr2 and GCaMP6f, jRCaMP1a, jRGECO1a, or R-CaMP2 fluorescence. For pacing of cardiomyocytes, a blue or violet LED source is positioned above the dish.

The inverted fluorescence micro-imaging system records optically from numerous (e.g., 50-5,000) expressing cells or cell clusters in a single field of view. The system may be used to characterize optically evoked firing patterns and AP waveforms in cardiomyocytes expressing an Optopatch construct. Each field of view is exposed to whole-field pulses of blue light to evoke activity (e.g., 5 ms, repeated at 1 Hz, 10 mW/cm$^2$). Reporter fluorescence such as QuasAr1 or QuasAr2 may be simultaneously monitored with whole-field excitation at 640 nm, 100 W/cm$^2$. Additional useful discussion of microscopes and imaging systems may be found in U.S. Pat. No. 8,532,398 to Filkins; U.S. Pat. No. 7,964,853 to Araya; U.S. Pat. No. 7,560,709 to Kimura; U.S. Pat. No. 7,459,333 to Richards; U.S. Pat. No. 6,972,892 to DeSimone; U.S. Pat. No. 6,898,004 to Shimizu; U.S. Pat. No. 6,885,492 to DeSimone; and U.S. Pat. No. 6,243,197 to Schalz, the contents of each of which are incorporated by reference.

Using the described methods, action potentials of cardiomyocytes may be determined.

The imaging system is used to capture movies of fluorescence emitted by the cells. Fluorescence values are extracted from raw movies by any suitable method. One method uses the maximum likelihood pixel weighting algorithm described in Kralj et al., 2012, Optical recording of action potentials in mammalian neurons using a microbial rhodopsin, Nat Methods 9:90-95. Briefly, the fluorescence at each pixel is correlated with the whole-field average fluorescence. Pixels that showed stronger correlation to the mean are preferentially weighted. This algorithm automatically finds the pixels carrying the most information, and de-emphasizes background pixels.

Methods of the invention are used to obtain a signature from the observed cell or cells tending to characterize a physiological parameter of the cell. Measurements can include different modalities, stimulation protocols, or analysis protocols. Exemplarily modalities for measurement include voltage, calcium, ATP, or combinations thereof. Exemplary stimulation protocols can be employed to simulate gradual or sudden changes in beat rate, or response to triggers of ectopic beats delivered at defined points during the AP waveform, or to determine the maximum beat rate under stimulus of gradually increasing frequency. These measurements can be applied in the presence of modulatory chemicals or genetic perturbations, or combinations thereof. Methods of invention may employ various analysis protocols to measure: beat frequency under different stimulus types, action potential waveform, resting potential, AP peak amplitude, others, or combinations thereof.

6. Drug Screens in Cardiomyocytes

A recent article reported that "Among the 100 top-selling drugs, 15 are ion-channel modulators with a total market value of more than $15 billion." See Molokanova & Savchenko, 2008, Bright future of optical assays for ion channel drug discovery, Drug Discov Today 13:14-22. However, searches for new ion-channel modulators are limited by the absence of good indicators of membrane potential. See Przybylo et al., 2010, Fluorescence techniques for determination of the membrane potentials in high throughput screening, J Fluoresc 20(6):1139-1157. In some embodiments, the optical reporters described herein are used to measure or monitor membrane potential changes in response to a candidate ion channel modulator. Such screening methods can be performed in a high throughput manner by simultaneously screening multiple candidate ion channel modulators in cells.

The constructs disclosed in the present application can be used in methods for drug screening for efficacy or safety. An exemplary protocol for drug screening and results are provided in the Examples section, below.

In a culture of cells expressing specific ion channels, one can screen for agonists or antagonists without the labor of applying patch clamp to cells one at a time. The constructs provided herein provide a new and much improved method to screen for drugs that modulate the cardiac action potential and its intercellular propagation. These screens will be useful both for determining safety of candidate drugs and to identify new cardiac drug leads. Identifying drugs that interact with the hERG channel is a particularly promising direction because inhibition of hERG is associated with ventricular fibrillation in patients with long QT syndrome. Application in human iPSC-derived cardiomyocytes will enable studies on genetically determined cardiac conditions, as well as studies on the response to environmental stresses (e.g. anoxia).

For example, in one embodiment, the invention provides a method wherein the cell expressing a microbial rhodopsin is further exposed to a stimulus capable of or suspected to be capable of changing membrane potential.

Stimuli that can be used include candidate agents, such as drug candidates, small organic and inorganic molecules, larger organic molecules and libraries of molecules and any combinations thereof. One can also use a combination of a known drug, such as an antiarrhythmic with a candidate agent to screen for agents that may increase the effectiveness of the one or more of the existing drugs, such as antiarrhythmics.

The methods of the invention are useful for in vitro toxicity screening and drug development. For example, using the methods described herein one can make a human cardiomyocyte from induced pluripotent cells, which cardiomyocyte stably expresses a modified Archaerhodopsin wherein the proton pumping activity is substantially reduced or abolished. Such cells are particularly useful for in vitro toxicity screening in drug development.

In a preferred embodiment, candidate compounds are screened and a non-binary cardiotoxicity score is assigned to a compound. Since methods of the invention provide for a greater number of variable measurements to be made, methods of the invention can provide a cardiotoxicity evaluation with greater information content than simple yes or no. With the measurements made, a cardiotoxicity score can be assigned from a range (e.g., 1-10, 0-100, A-F). In some embodiments, a multivariable cardiotoxicity score is assigned (e.g., with a separate score value assigned to each of two or more aspects of cardiac effect). A multivariable non-binary score is possible since methods described herein measure more than one physiological parameter of a cell and also measure full waveforms (e.g., AP and/or CT) over time. Thus in some embodiments, methods of the invention include assigning a non-binary score that includes individual scores for cardiac effects of a compound for two or more of recorded QT interval, early after depolarization, alternans, cessation of beating, change in spontaneous beat rate, conduction velocity, action potential width at 30% maximum depolarization, action potential width at 70% maximum depolarization, action potential width at 90% maximum depolarization, voltage drift during diastolic interval, and maximal upstroke velocity.

7. Systems of the Invention

Figure 15:
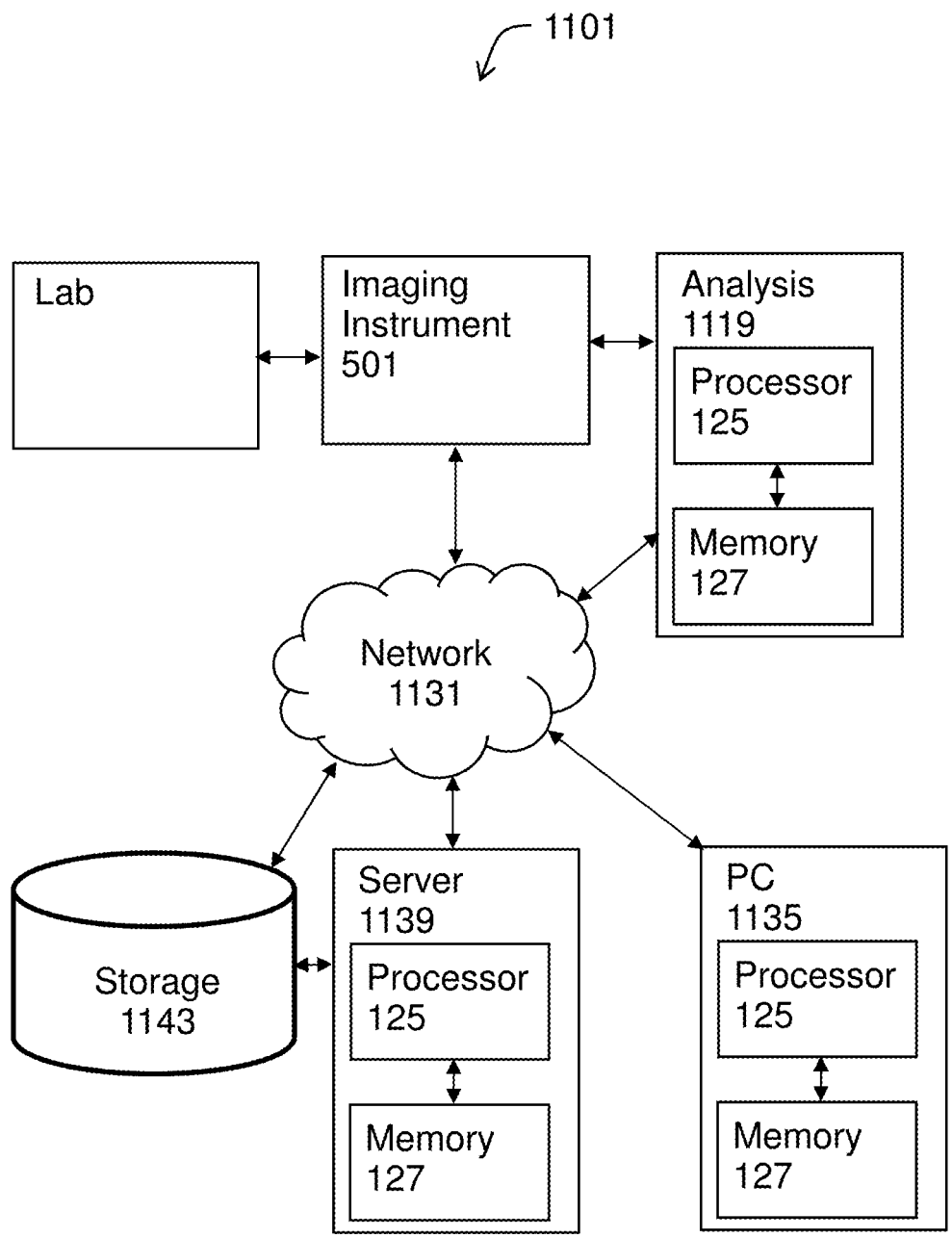
FIG. 15 presents a system of the invention.

FIG. 15 presents a system 1101 useful for performing methods of the invention. Results from a lab (e.g., transformed, converted patient cells) are loaded into imaging instrument 501. Imaging instrument 501 is operably coupled to an analysis system 1119, which may be a PC computer or other device that includes a processor 125 coupled to a memory 127. A user may access system 1101 via PC 1135, which also includes a processor 125 coupled to a memory 127. Analytical methods described herein may be performed by any one or more processor 125 such as may be in analysis system 1119, PC 1135, or server 1139, which may be provided as part of system 1101. Server 1139 includes a processor 125 coupled to a memory 127 and may also include optional storage system 1143. Any of the computing device of system 1101 may be communicably coupled to one another via network 1131. Any, each, or all of analysis system 1119, PC 1135, and server 1139 will generally be a computer. A computer will generally include a processor 125 coupled to a memory 127 and at least one input/output device.

A processor 125 will generally be a silicon chip microprocessor such as one of the ones sold by Intel or AMD. Memory 127 may refer to any tangible, non-transitory memory or computer readable medium capable of storing data or instructions, which—when executed by a processor 125—cause components of system 1101 to perform methods described herein. Typical input/output devices may include one or more of a monitor, keyboard, mouse, pointing device, network card, Wi-Fi card, cellular modem, modem, disk drive, USB port, others, and combinations thereof. Generally, network 1131 will include hardware such as switches, routers, hubs, cell towers, satellites, landlines, and other hardware such as makes up the Internet.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Cardiotoxicity Screening with Simultaneous Optogenetic Pacing, Voltage Imaging and Calcium Imaging Toxicity accounts for 20% of all drug attrition during drug development, of which more than one third is cardiovascular. In particular, drug induced abnormalities in the electrocardiogram (ECG), which can lead to sudden death, account for roughly half of those failures in pharmaceutical development. Because the cost of bringing a novel chemical entity to market is estimated to exceed $1.2 billion, along with >10 years of research and development, it is critical to address and eliminate the cardiovascular toxicity to bring the best compounds forward.

A major focus in reducing acute cardiotoxicity has been to identify compounds that cause acquired long QT syndrome in humans; as a causal link between QT prolongation and increased incidence of the potentially lethal arrhythmia, TdP, has been established. As our understanding of the electrophysiological mechanisms for QT prolongation has increased, especially the propensity of hERG potassium channel blockade to cause long QT and TdP, regulatory agencies have created guidance documents (ICHS7A/B) to characterize both the in vitro and in vivo consequences of this property.

However, studies on clinically relevant compounds have shown that hERG inhibition is not always predictive of QT prolongation and torsadogenic potential. While highly selective hERG blockers tend to prolong the ECG when unbound plasma concentrations fall within 30-100 fold of their hERG IC50, compounds with multiple targets can exist in this concentration range yet elicit little to no change in QTc.

Here, optogenetic assays are used to stimulate depolarization through paced cultures and to visualize simultaneously the AP and CT of hiPSC-derived cardiomyocytes. Stimulation and pacing of cardiomyocytes are achieved via CheRiff. Detection of action potential (AP) and calcium transient (CT) waveforms is accomplished via a fusion protein of QuasAr2 and a GECI.

Materials and Methods

Culturing of Cardiomyocytes

Cardiomyocytes sold under the trademark ICELL are purchased from Cellular Dynamics Inc. (CDI, Madison Wis.). The cardiomyocytes are thawed, plated, and incubated before transduction with optogenetic vectors.

Five days after plating, cardiomyocytes are transduced with lentiviral vectors. Lentiviral delivery is used to express CaViar & CheRiff. Viral delivery typically resulted in 8-10 expressing cells per field of view at 20× magnification.

Each compound may be dissolved in DMSO or H2O by vortexing the solution at room temperature until completely dissolved, typically 2-3 minutes. Aliquots (100 µL) are prepared and immediately stored at −20° C. until use. Optopatch measurements are made using the instrument depicted in FIG. 14. Red (635 nm) and/or blue (488 nm) laser light is directed towards the sample through a 20×, NA 1.0 water-immersion objective in an epifluorescence format. Fluorescence is collected by the same objective and passed through a dichroic mirror. A home-built dual view detection scheme is used to image each fluorescent band onto adjacent halves of a scientific CMOS (sCMOS) camera. This approached allows for simultaneous detection of QuasAr2 and GECI fluorescence. For pacing of cardiomyocytes, a blue LED source is positioned above the dish.

For each compound and each concentration, stocks are prepared by dilution from the 10 10 mM stock in cardiac imaging buffer and kept at 37° C. in 5% CO2 prior to use. The diluted drug stocks are made such that the desired final drug concentration could be achieved upon addition of 100 μL to the dish. A 'blank' containing cardiac imaging buffer alone was also prepared for each drug and kept at 37° C. in 5% CO2 prior to use. All dilutions were prepared fresh from a 10 10 mM stock the day of the measurement.

Measurement of Electrophysiological Response

Spontaneous Beating and Paced Action Potentials

Figure 16:
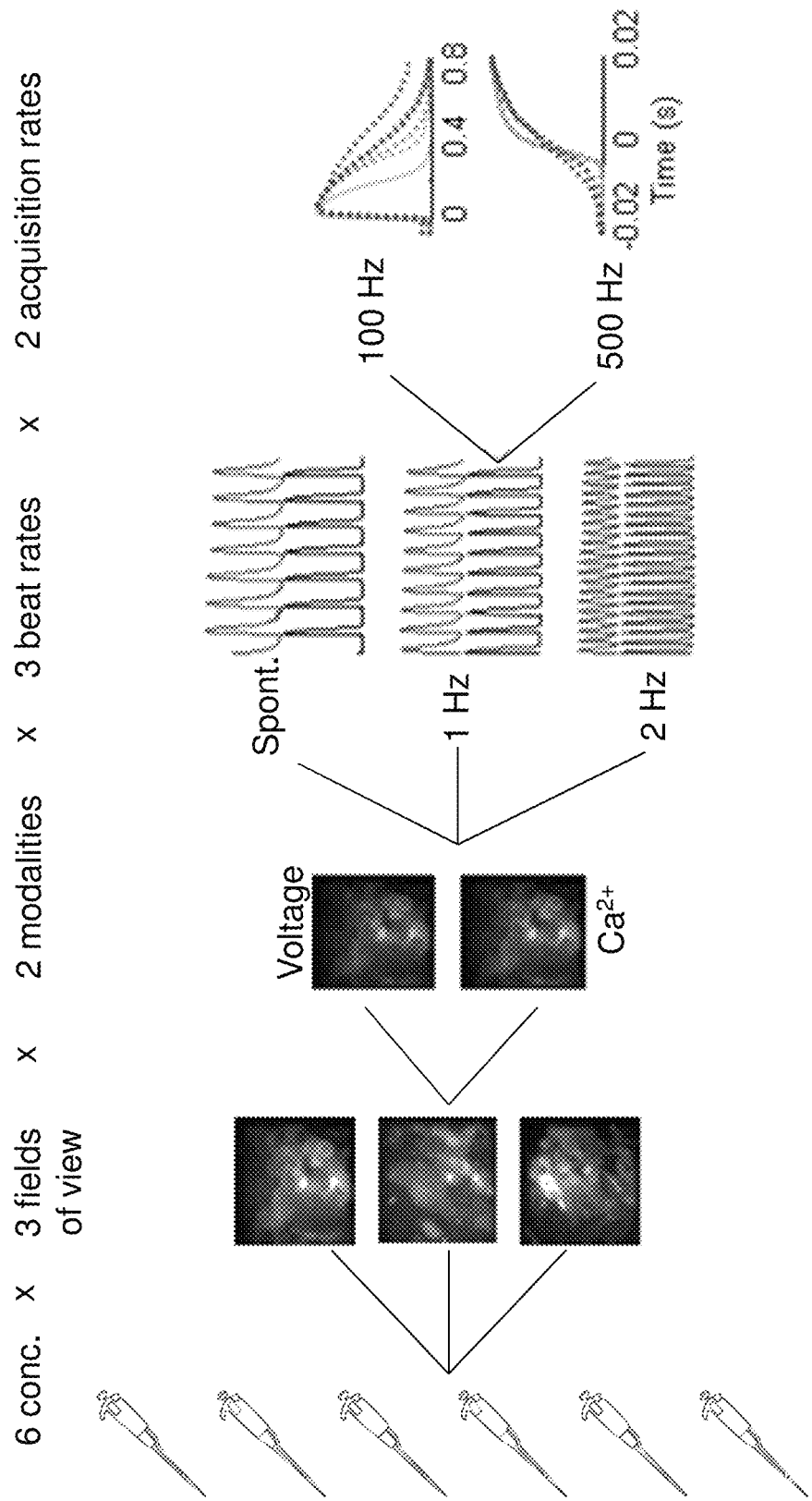
FIG. 16 gives a summary of Optopatch acute drug screening measurements.

FIG. 16 gives a summary of Optopatch acute drug screening measurements. Dose-response curves are acquired on two independent cultures to control for dish-to-dish variation, and in three regions within each dish to control for region-to-region variation. Action potential (AP) waveforms and Ca2+ transients (CTs) are recorded under three optical pacing regimes, to detect beat rate-associated changes in behavior. Two data acquisition rates were used, 100 Hz to record AP waveform, and 500 Hz to record rising edge velocity.

For measurement of spontaneous activity, hiPSC-derived CMs expressing CaViar are exposed to whole-field, constant illumination with red laser light ($\lambda$=640 nm, 50 W/cm2) to excite fluorescence of the QuasAr2 voltage indicator. Fluorescence was collected via a 20× water immersion objective with a numerical aperture (NA) of 1.0 (Olympus or Zeiss) and separated from illumination light via a Cy5 emission filter (Chroma). Signals are recorded on a scientific CMOS (sCMOS) camera (Hamamatsu) at frame rates of 100 Hz or 500 Hz.

For pacing, pulses of blue LED illumination (6 ms, 0.5 W/cm2) are delivered to the dish to stimulate the optogenetic actuator, which paces the entire syncytium through gap junction-mediated lateral conduction. Fluorescence is then recorded from the central QuasAr2-expressing cells under simultaneous constant red illumination (as described above). Simultaneous pacing and measurements of voltage and Ca2+ are performed by plating CheRiff- and Caviar-expressing cardiomyocytes Pulses of blue LED illumination are delivered to pace the cells.

Continuous blue and red illumination are delivered to monitor voltage and Ca2+ and voltage simultaneously. This is achieved through whole-field illumination with continuous blue laser light ($\lambda$=488 nm, 0.15 W/cm2) to excited fluorescence of the GECI, and red laser light ($\lambda$=640 nm, 50 W/cm2) to excited fluorescence of the QuasAr2 voltage indicator. A dual-view imaging system projected emission from the GECI (525-575 nm) and from QuasAr2 (660-760 nm) onto adjacent halves of a sCMOS camera, operating at a frame rates of either 100 Hz or 500 Hz. Custom LabView scripts (National Instruments) scripts controlled the illumination, camera and electrophysiological optogenetic stimuli.

Addition of Compounds and Imaging Protocol

Imaging is performed on a custom-built epi-fluorescence microscope. Cells are maintained at a temperature of 35-37° C. on the microscope using a heated stage (Warner Instruments) and objective collar (Bioptechs). A home-built environmental chamber is constructed for environmental control of the sample during imaging. Humidified air with 5% CO2 was flowed into the chamber throughout the experiments.

Each serial addition of a compound is performed as follows. A MatTek dish is placed on the microscope for 10 minutes to allow the cells to stabilize in the environmental chamber before imaging. Cells are then pre-paced at a pulse-rate of 2 Hz for 1 minute, followed by continuous illumination with red light for 20 seconds. This serves to expose all the cells in the dish to the same pacing stimulus before addition of a compound. A 'blank' negative buffer control of 100 μL is then added to the dish and thoroughly mixed by pipetting ten times. The sample is then allowed to stabilize for 3-5 minutes before the start of the imaging protocol. The imaging protocol is performed for three fields of view (FOV) and the microscope xy-stage positions saved for each. Immediately after, 100 μL of the warmed, diluted stock concentration is added to the dish and mixed ten times to achieve the lowest desired drug concentration. The imaging protocol is then performed for the same 3 FOV. This process was repeated for each drug concentration, as listed in FIG. 17. A vehicle control is performed for DMSO at concentrations of 0.003%, 0.01%, 0.03%, 0.1% and 0.3%.

The imaging protocol performed for each FOV is was as follows:

3 seconds of red laser illumination to reduce the presence of phototransients before the recording;

30 seconds of red laser and blue laser to record spontaneous beating: 25 seconds recording at 100 Hz frame rate followed by 5 seconds recording at 500 Hz; frame rate Red (and blue) laser illumination turned off for 4 seconds to allow for data storage;

Blue LED illumination to pace the cells at 1 Hz for 1 minute;

Simultaneous 1 Hz pacing of the cells with 15 seconds of red and blue laser illumination: 10 seconds recording at 100 Hz frame rate followed by 5 seconds recording at 500 Hz; frame rate Red and blue laser illumination turned off for 4 seconds to allow for data storage;

Blue LED illumination to pace the cells at 2 Hz for 1 minute;

Simultaneous pacing of the cells at 2 Hz with 15 seconds of red and blue laser illumination: 10 seconds recording at 100 Hz frame rate followed by 5 seconds recording at 500 Hz. frame rate Analysis Data analysis is performed using custom Matlab software focused on quantifying:

Changes in AP waveform (early after depolarizations or EADs, alternans, cessation of beating)

Changes in calcium handling: cessation of Ca2+ flux, Ca2+ sparks, baseline Ca2+ and Ca2+ amplitude (3 compounds and 1 control)

AP50, AP90, beat rate, and maximal upstroke velocity (14 compounds and 1 control)

Identification of Action Potentials

To identify the timing of the action potentials, voltage traces are first corrected for photobleaching using a sliding linear interpolation with a 2 second window. Each trace is scaled to report fractional changes in fluorescence relative to baseline ($\Delta$F/F). The first derivative of each trace is used to locate the spike upstroke (maximal dF/dt) and this is recorded as the spike time.

In paced recordings, blue light stimulus artifacts are removed by linear interpolation between the frames immediately before and after the stimulus pulse. There is typically a 10 ms delay between the onset of the blue pulse and the upstroke of the AP.

Ca2+ traces are not corrected for photobleaching. The spike timing is extracted using the information from the voltage traces. Each Ca2+ trace is scaled to fractional fluorescence units, $\Delta$F/F.

Classification of Action Potentials

The inter-beat interval is calculated by recording the average time, in seconds, between each beat. Beats per minute is calculated dividing 60 by this time.

AP50 and AP90 are measured by normalizing (between 0 and 1) the average beat from each 100 Hz frame frame-rate movie. The AP width is then measured as the time between the crossing of 0.5 (or 0.1) on the upstroke and the downstroke. Linear interpolation is used to achieve sub-frame precision in this timing.

The rise time is determined from the 500 Hz movies. Each beat is normalized between 0 and 1, and the upstroke is defined as the time for the voltage to travel between 30 and 70% of the full amplitude. Timing is calculated with sub-frame precision using linear interpolation. The reported value is the mean rise time of each beat over all beats in a given trace.

Ca2+ transient amplitude is calculated by taking the maximal value of the scaled, averaged calcium beat.

Results

QuasAr2 Reports AP Waveforms with Minimal Perturbation to CMs

QuasAr2 is a red-light-excited voltage indicating fluorescent protein, which has been shown in neurons to have high sensitivity to voltage changes (90% ΔF/F per 100 mV), a rapid response time (0.3 ms at 34° C.) and improved brightness over previous versions of Arch. In neurons, expression of QuasAr2 does not perturb resting voltage, membrane resistance, membrane capacitance, action potential initiation voltage, or action potential waveform. QuasAr2 operates as a voltage indicator in cardiomyocytes.

The capability of QuasAr2 to report AP waveforms is tested by comparing with the voltage-sensing dye (VSD), FluoVolt. The QuasAr2 gene is expressed under control of the CMV promoter in a subset of hiPSC-derived CMs and then all cells in the dish are labelled with FluoVolt. Comparison of FluoVolt and QuasAr2 signals in cells expressing QuasAr2 probed whether QuasAr2 accurately reported the AP waveform in the cells in which it was expressed. Comparison of FluoVolt signals between cells +/−QuasAr2 probed whether expression and imaging of QuasAr2 perturbed the AP waveform.

Measurements are performed on spontaneously beating cells in a dual-view wavelength imaging setup system to simultaneously record protein and dye fluorescence for the same field of view. In all cases, the cells showed spontaneous beating activity. Cells expressing QuasAr2 and labeled with FluoVolt showed transient bursts of fluorescence in the near-IR and blue/green portions of the spectrum, respectively, concomitant, synchronous with the beating. The average AP waveform was calculated independently for both QuasAr2 and FluoVolt. An overlay of the two waveforms showed good correspondence, with a <2% difference in the AP50. To test whether expression of QuasAr2 affected the AP waveform parameters, we compared FluoVolt signals in cells +/−QuasAr2 expression. The FluoVolt waveform showed no detectable difference between cells +/−QuasAr2.

CheRiff and CaViar Form the Optopatch System to Optically Stimulate and Record Voltage and Ca2+ in hiPSC-Derived CMs We next sought to create: 1) a fluorescent indicator for simultaneous detection of both voltage and $Ca^{2+}$ and 2) an optogenetic actuator for CM pacing. The first goal was motivated by the importance of both voltage and $Ca^{2+}$ in CM electrophysiology. Excitation contraction coupling is mediated through voltage dependent Ca2+ flow into the cytoplasm, followed by calcium-triggered calcium release from the sarcoplasmic reticulum. Simultaneous measurement of multiple modalities can distinguish among multiple possible drug mechanisms of action. The second goal was motivated by the importance of pacing in CMs. Pacing eliminates drug induced changes in beat rate, thereby highlighting direct effects of drugs on AP parameters.

A channelrhodopsin variant such as CheRiff, TsChR, or PsChR triggers APs in neurons using approximately 9-fold lower blue light intensity than is required for the widely used Channelrhodopsin 2 H134R actuator. The second construct is a fusion protein called CaViar. CaViar consists of QuasAr2 fused to a GECI. The combination of the channelrhodopsin actuator and CaViar reporter form the basis of the platform we call cardiac Optopatch.

To avoid artifacts from non-specific channelrhodopsin conductance, cells may be independently transduced with either CheRiff or CaViar and re-plated onto glass bottom dishes. The CheRiff-expressing cells provided pacing, but are not directly measured, so ionic perturbation due to the CheRiff conductance does not contaminate the measurements of the CaViar-expressing cells. Pacing is achieved via 6 ms flashes from a blue LED placed above the sample. Imaging is achieved via continuous epifluorescence illumination from below with a red laser for QuasAr2 excitation and a blue laser, when used, for GECI excitation. AP and CT waveforms could be detected for spontaneous or paced beating at 1 Hz and 2 Hz.

In preferred embodiments, the actuator is a channelrhodopsin variant such as CheRiff or one such as TsChR or PsChR with maximal activation at a violet light wavelength between 400-440 nm (further to the blue than CheRiff). The channelrhodopsin variant is simultaneously combined with a GECI (such as jRCaMP1a, jRGECO1a, or R-CaMP2) and a red-excited voltage indicator, e.g. QuasAr2, for simultaneous monitoring of $Ca^{2+}$ and voltage under optical pacing.

Cardiac Optopatch as a Platform for Cardiotoxicity Screening/Testing

We next tested the effects of drugs on cardiac AP dynamics.

FIG. 17 lists compounds for testing with cardiomyocytes. For each measurement, the quantified parameters include the AP30 (ms), AP60 (ms), AP90 (ms), AP90-AP30 (ms), AP rise time (ms), Ca2+ amplitude, and spontaneous beat rate. Nine compounds are tested—a DMSO control and eight with known mechanisms, including a variety of several hERG K+ and Na+ channel blockers. Results for the nine compounds are given.

FIGS. 18-44 give results of exposing cardiomyocytes to the compounds.

FIGS. 18, 21, 24, 27, 30, 33, 36, and 39 show representative segments of the mean fluorescence (ΔF/F) versus time (seconds, s) traces at each concentration (0 μM 'blank', 1 μM, 3 μM, 10 μM, and 30 μM) are shown. For FIGS. 18, 21, 24, 27, 30, 33, 36, and 39: the top row shows CT printed above AP waveforms for spontaneously beating cells; and the CTs above AP waveforms are shown for cells paced at 1 Hz and 2 Hz in the middle and bottom rows, respectively.

For FIGS. 19, 22, 25, 28, 31, 34, 37, 40, and 43, the left panels show average waveform and the right panels show rise time, with the top row=spontaneously beating cells; the middle row=cells paced at 1 Hz; and the bottom row=cells paced at 2 Hz (dashed lines indicate that the cells did not beat at the specified pacing rate). Left and right panels are calculated from data taken at 100 Hz and 500 Hz, respectively.

FIGS. 23, 26, 29, 32, 35, 38, 41, and 44 show—for the various compounds—the dose dependence of certain AP waveform and CT parameters that include the AP30 (ms), AP60 (ms), AP90 (ms), AP90-AP30 (ms), AP rise time (ms), Ca2+ amplitude, and spontaneous beat rate, in the respectively labeled panels. In each panel, the top trace is for spontaneously beating cells, the middle trace for cells paced at 1 Hz, and the lower trace for cells paced at 2 Hz. Note that in the case of 1 Hz and 2 Hz pacing, data points are omitted from the plot in the event that the cells do not pace at the specified pace rate. Data points are also omitted in the event that the cells stop beating. Data and error bars are reported as the mean+/−standard error of the mean.

Figure 18:
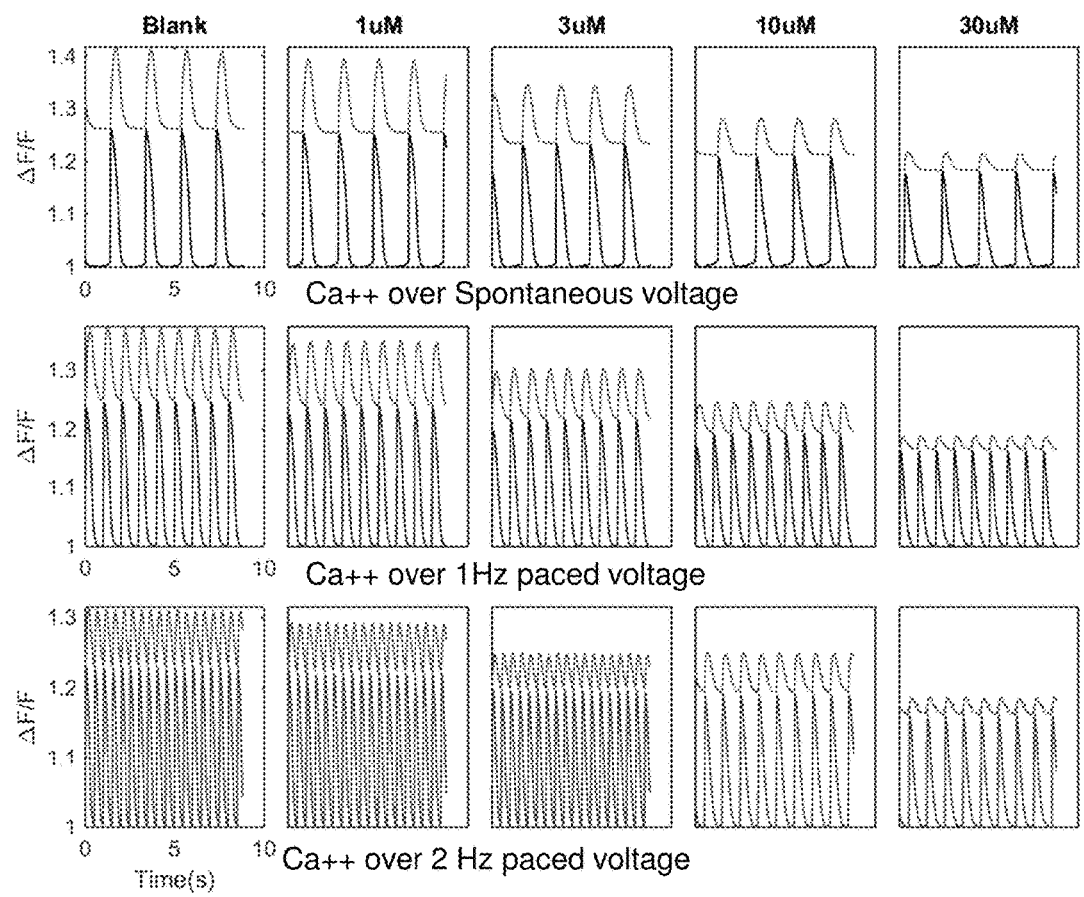
FIG. 18 shows the effects of ranolazine on cardiomyocytes.

FIG. 18 shows the effects of ranolazine on cardiomyocytes.

Figure 19:
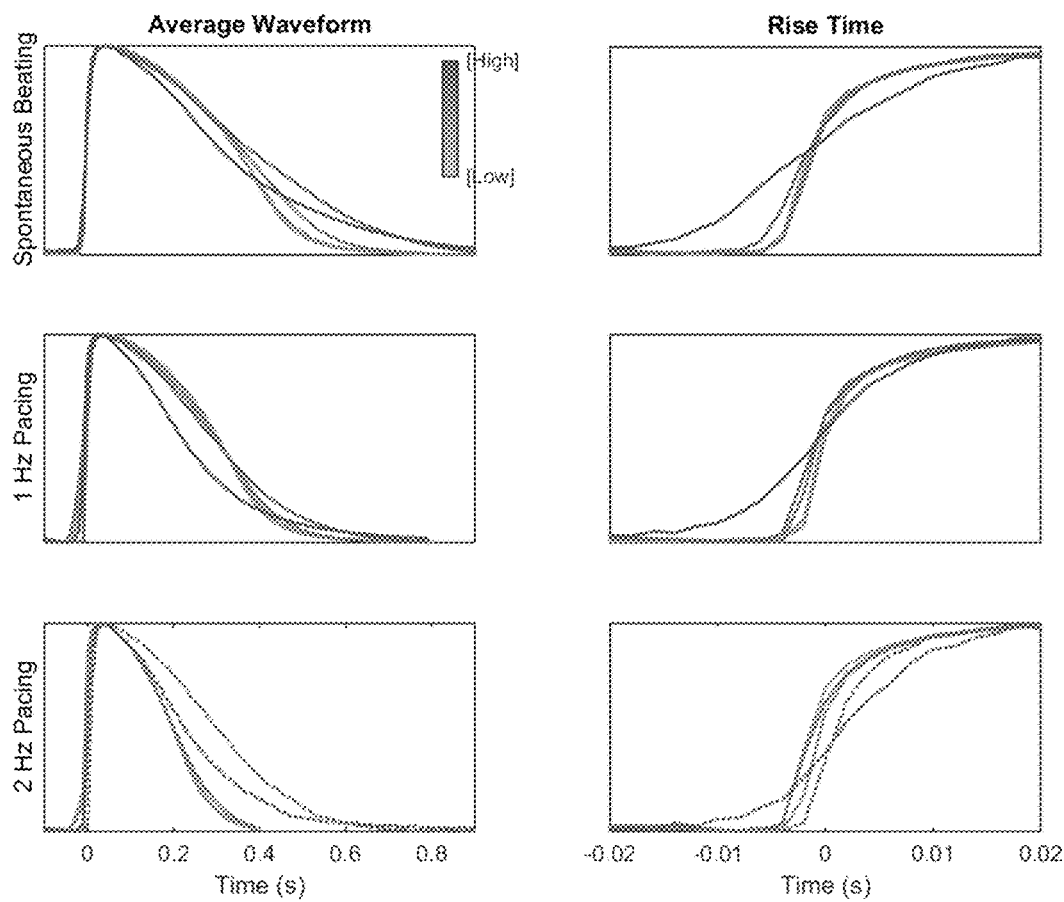
FIG. 19 shows the effect of ranolazine on average AP waveform and rise time

FIG. 19 shows the effect of ranolazine on average AP waveform and rise time

Figure 20:
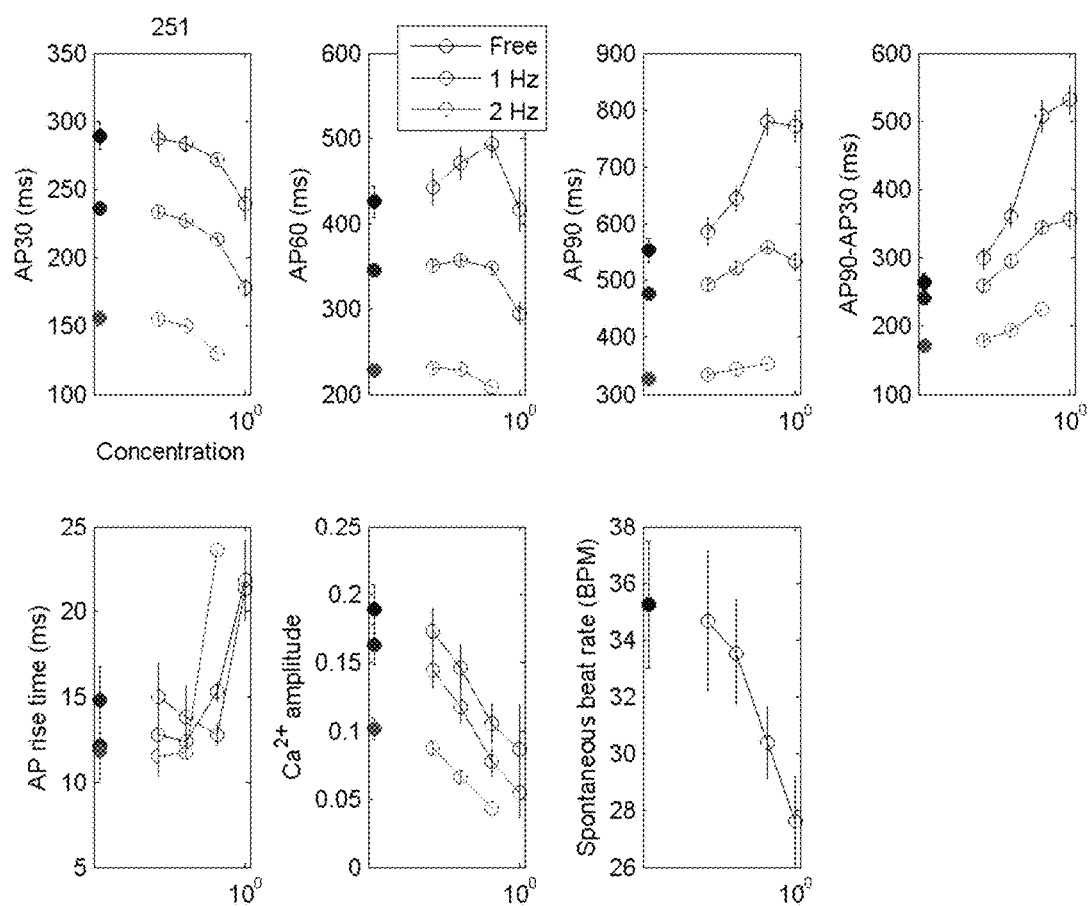
FIG. 20 shows the ranolazine dose dependence of certain AP waveform and CT effects.

FIG. 20 shows the ranolazine dose dependence of certain AP waveform and CT effects.

Figure 21:
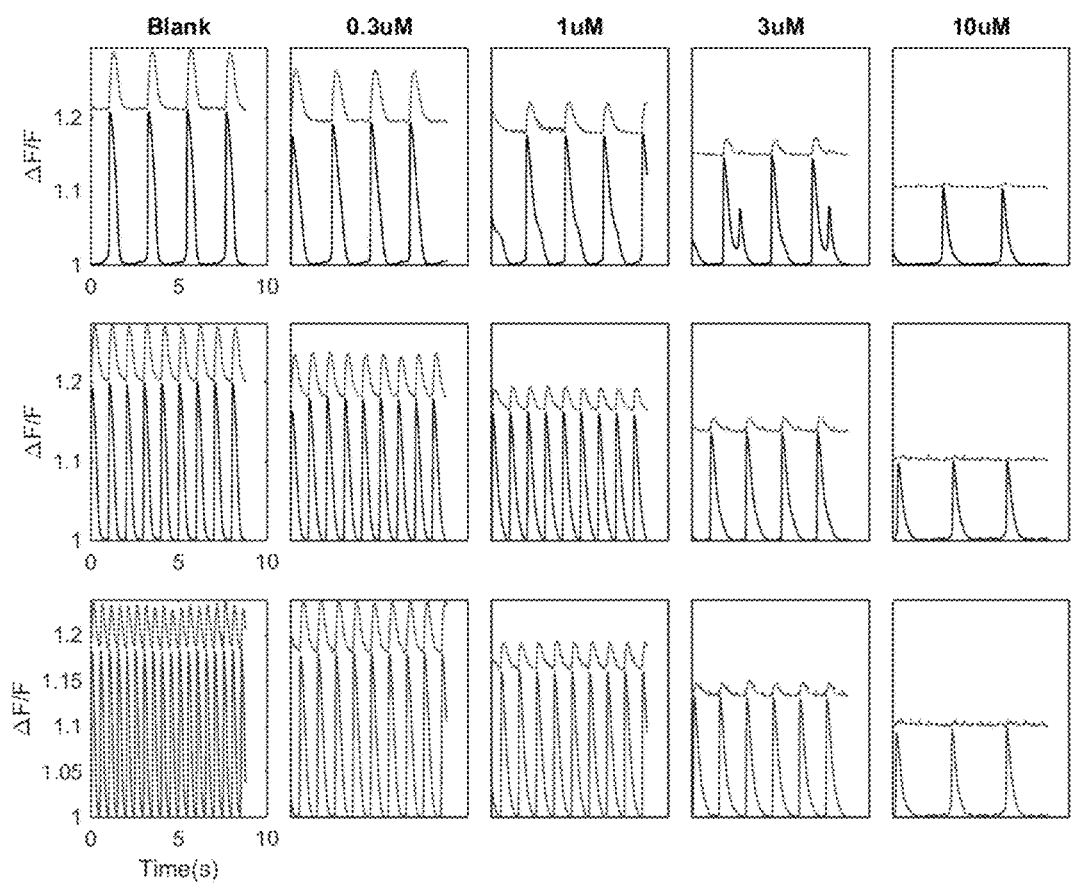
FIG. 21 shows the effects of quinidine on cardiomyocytes.

FIG. 21 shows the effects of quinidine on cardiomyocytes.

Figure 22:
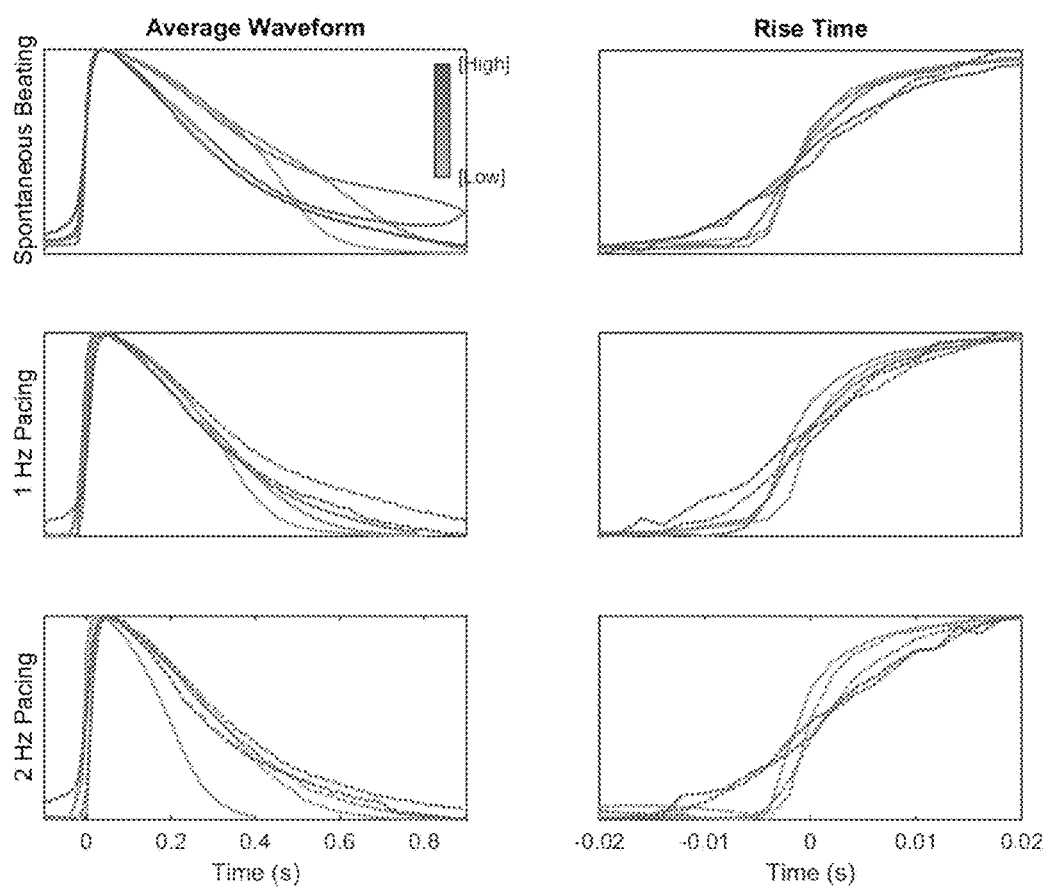
FIG. 22 shows the effect of quinidine on average AP waveform and rise time

FIG. 22 shows the effect of quinidine on average AP waveform and rise time

Figure 23:
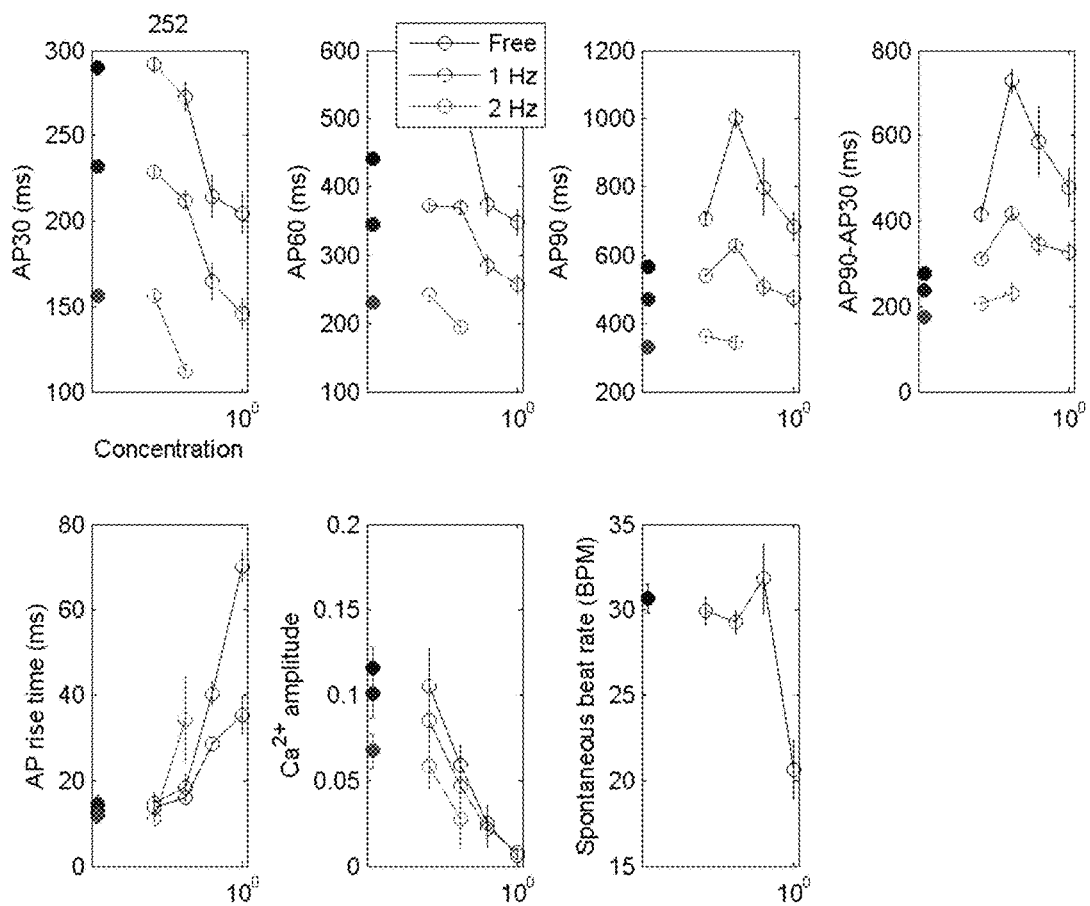
FIG. 23 shows the quinidine dose dependence of certain AP waveform and CT effects.

FIG. 23 shows the quinidine dose dependence of certain AP waveform and CT effects.

Figure 24:
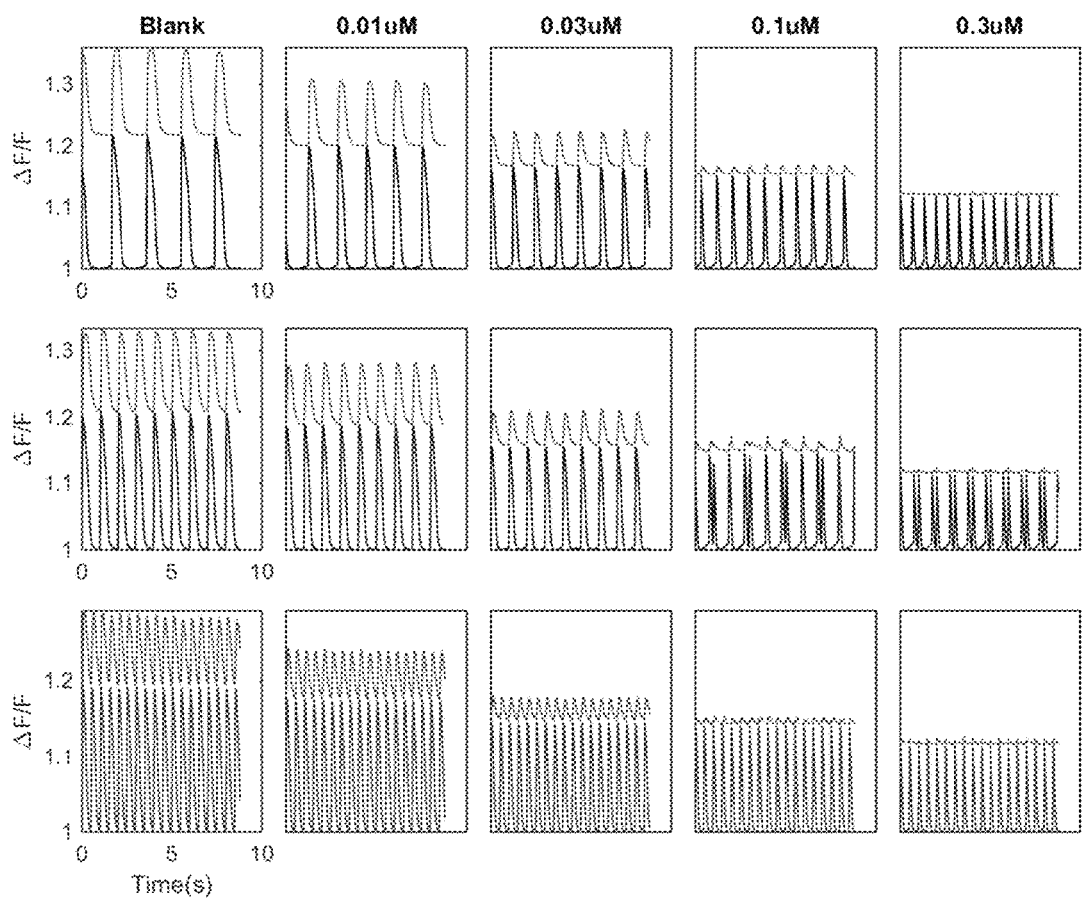
FIG. 24 shows the effects of nifedipine on cardiomyocytes.

FIG. 24 shows the effects of nifedipine on cardiomyocytes.

Figure 25:
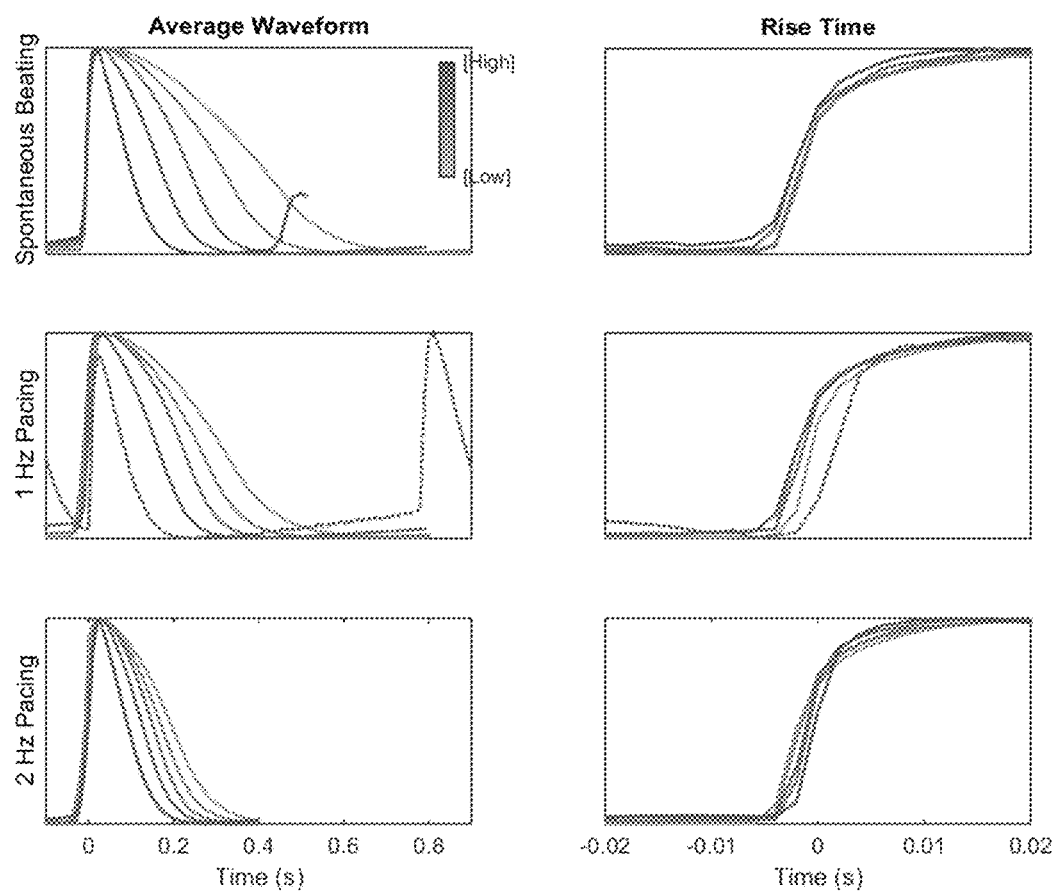
FIG. 25 shows the effect of nifedipine on average AP waveform and rise time

FIG. 25 shows the effect of nifedipine on average AP waveform and rise time

Figure 26:
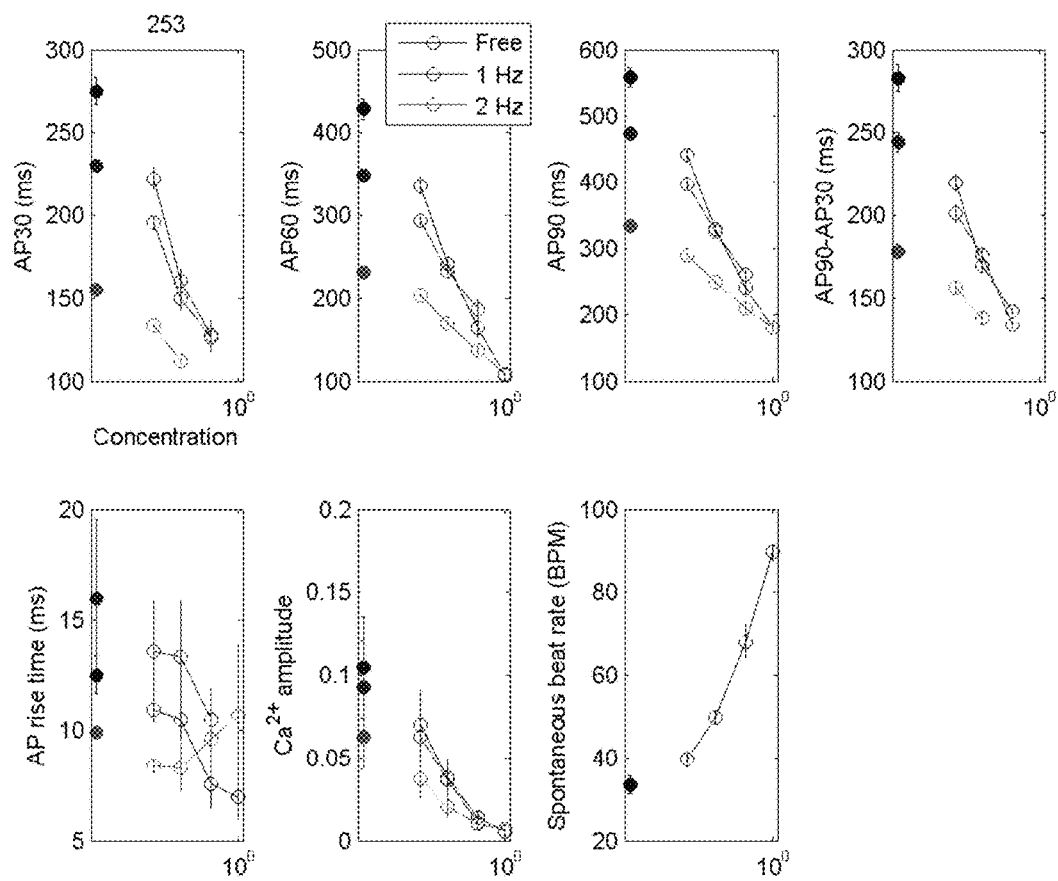
FIG. 26 shows the nifedipine dose dependence of certain AP waveform and CT effects.

FIG. 26 shows the nifedipine dose dependence of certain AP waveform and CT effects.

Figure 27:
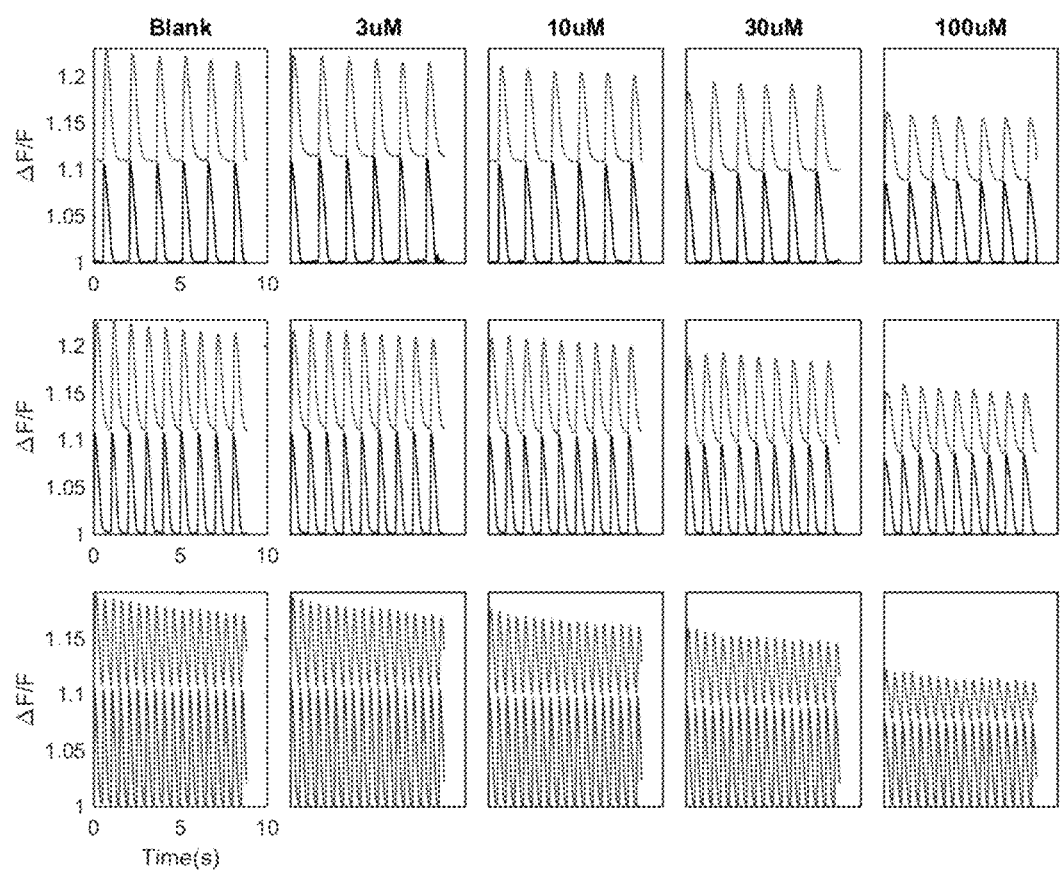
FIG. 27 shows the effects of moxifloxacin on cardiomyocytes.

FIG. 27 shows the effects of moxifloxacin on cardiomyocytes.

Figure 28:
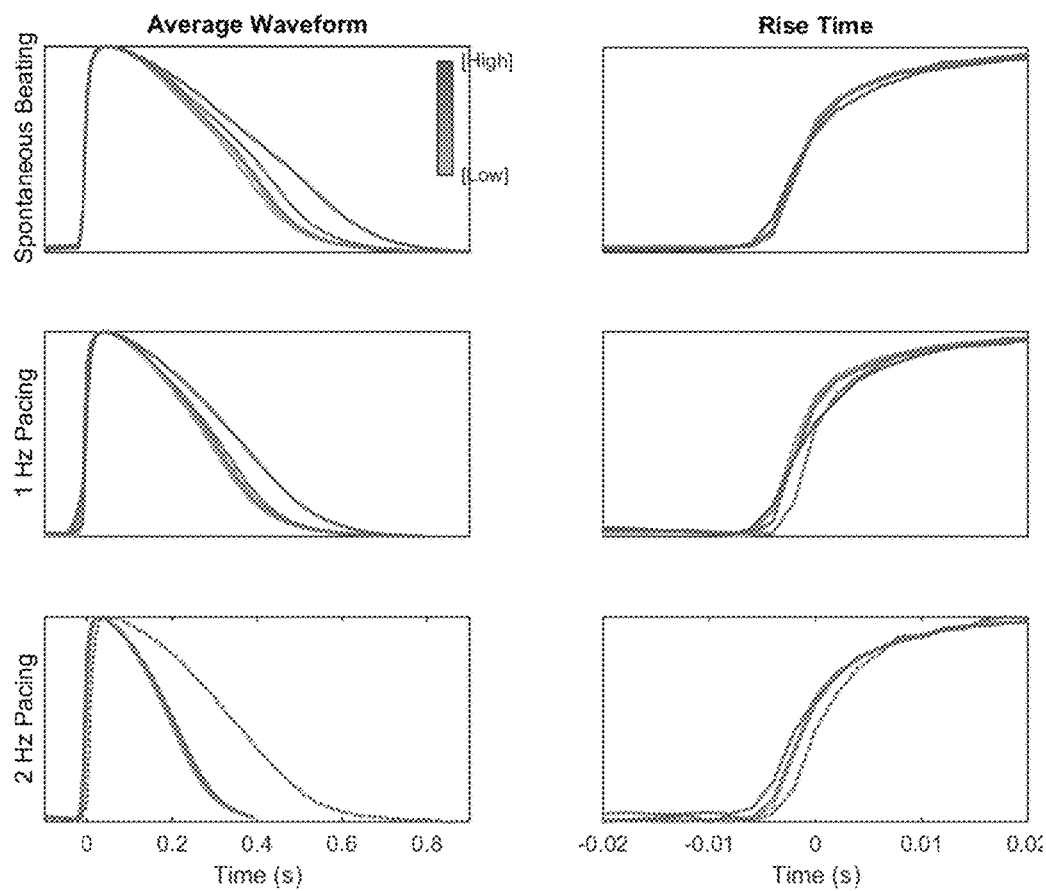
FIG. 28 shows the effect of moxifloxacin on average AP waveform and rise time

FIG. 28 shows the effect of moxifloxacin on average AP waveform and rise time

Figure 29:
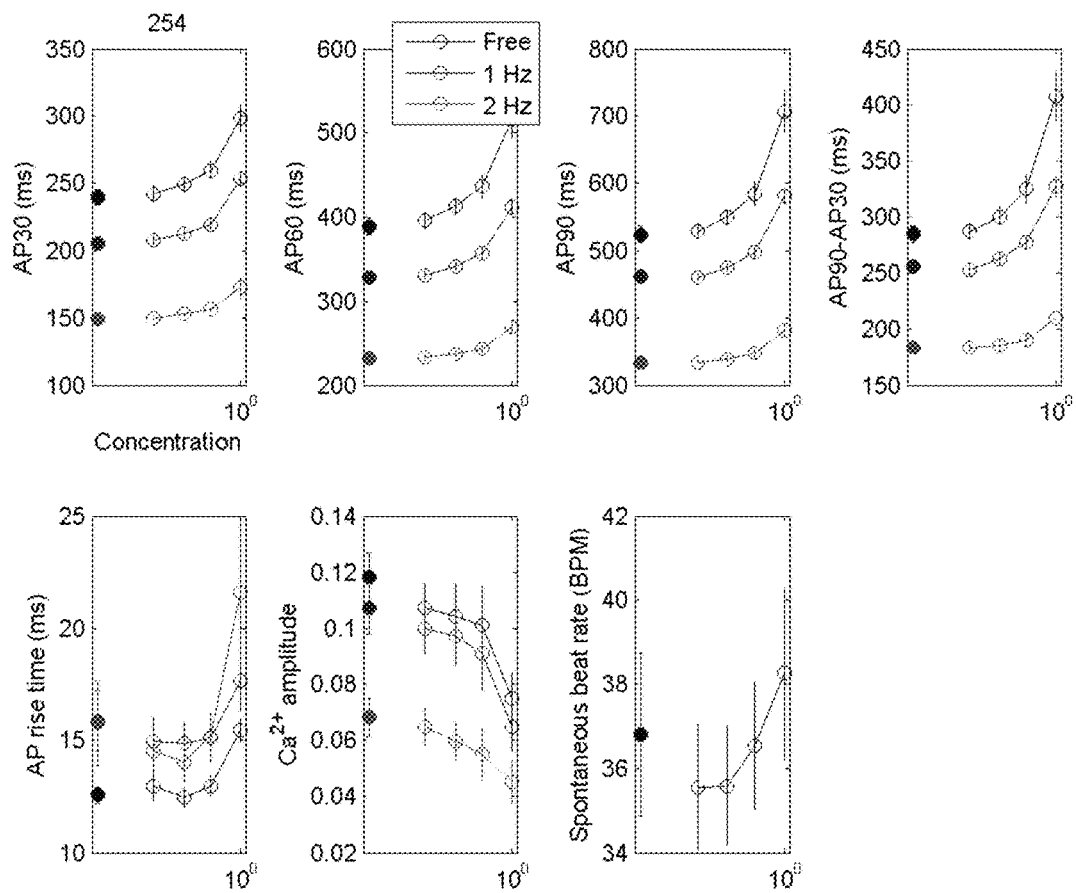
FIG. 29 shows the moxifloxacin dose dependence of AP waveform and CT effects.

FIG. 29 shows the moxifloxacin dose dependence of certain AP waveform and CT effects.

Figure 30:
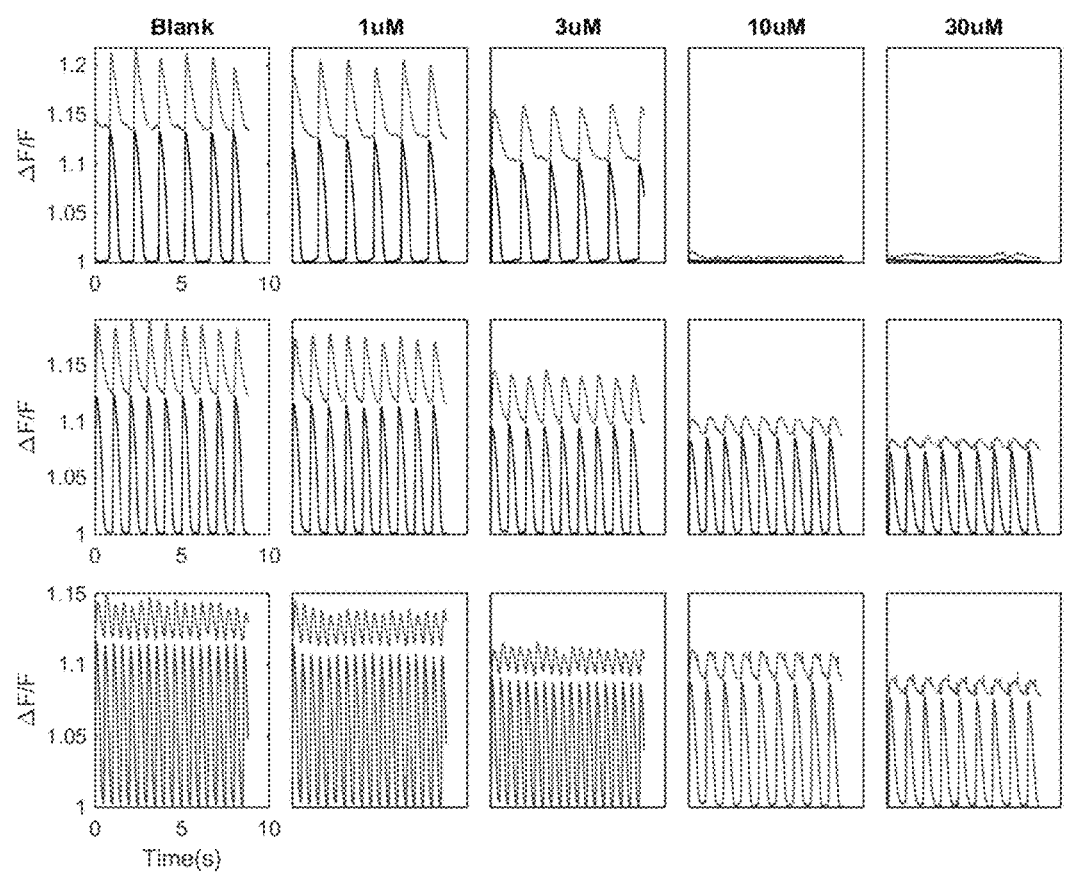
FIG. 30 shows the effects of mexiletine on cardiomyocytes.

FIG. 30 shows the effects of mexiletine on cardiomyocytes.

Figure 31:
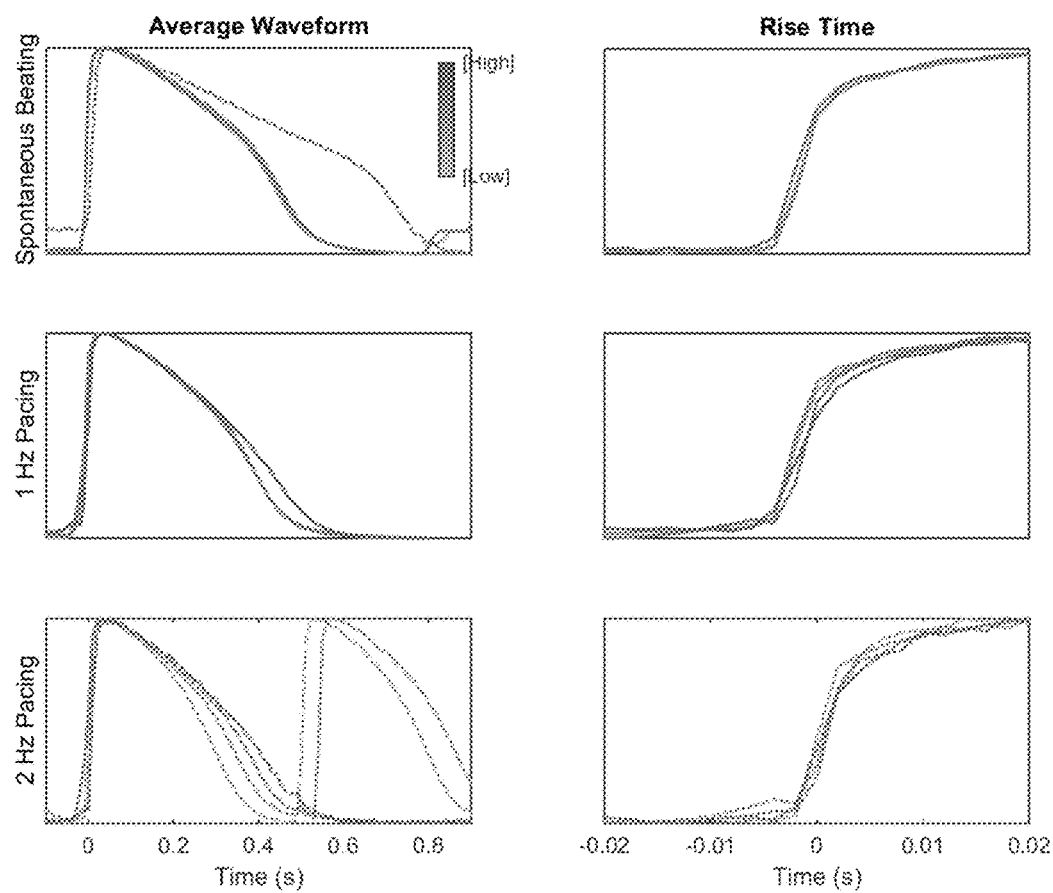
FIG. 31 shows the effect of mexiletine on average AP waveform and rise time

FIG. 31 shows the effect of mexiletine on average AP waveform and rise time

Figure 32:
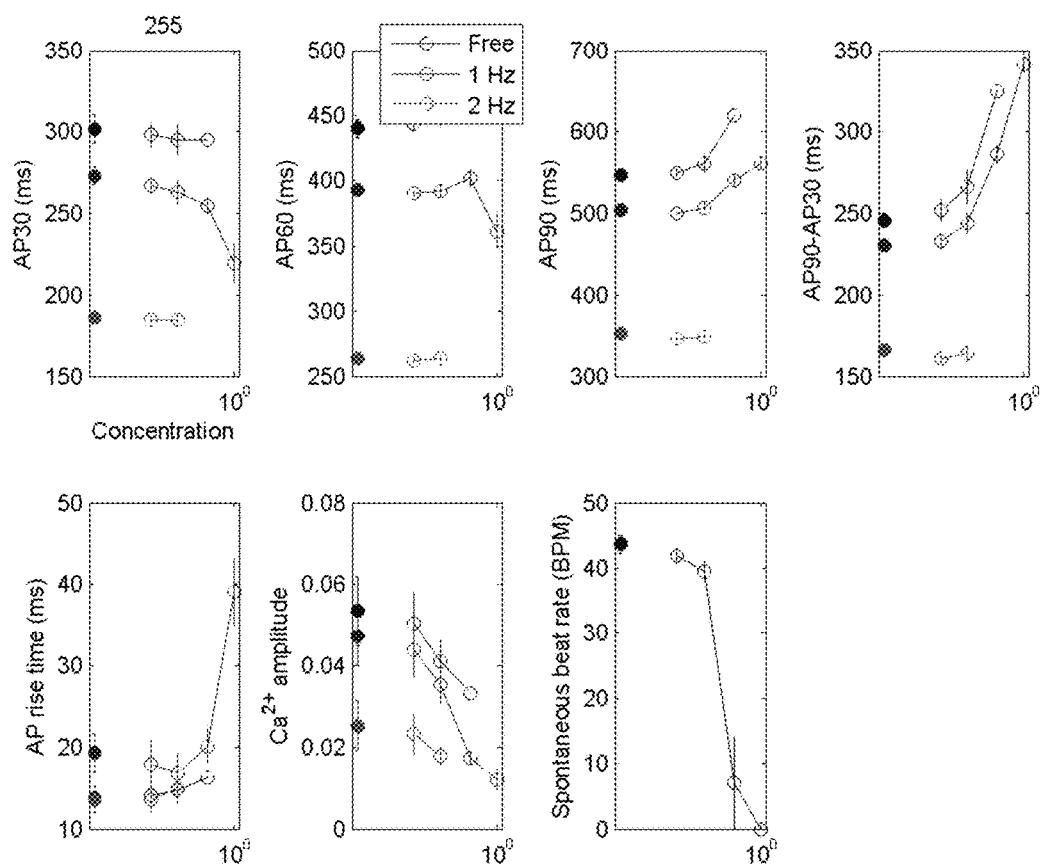
FIG. 32 shows the mexiletine dose dependence of certain AP waveform and CT effects.

FIG. 32 shows the mexiletine dose dependence of certain AP waveform and CT effects.

Figure 33:
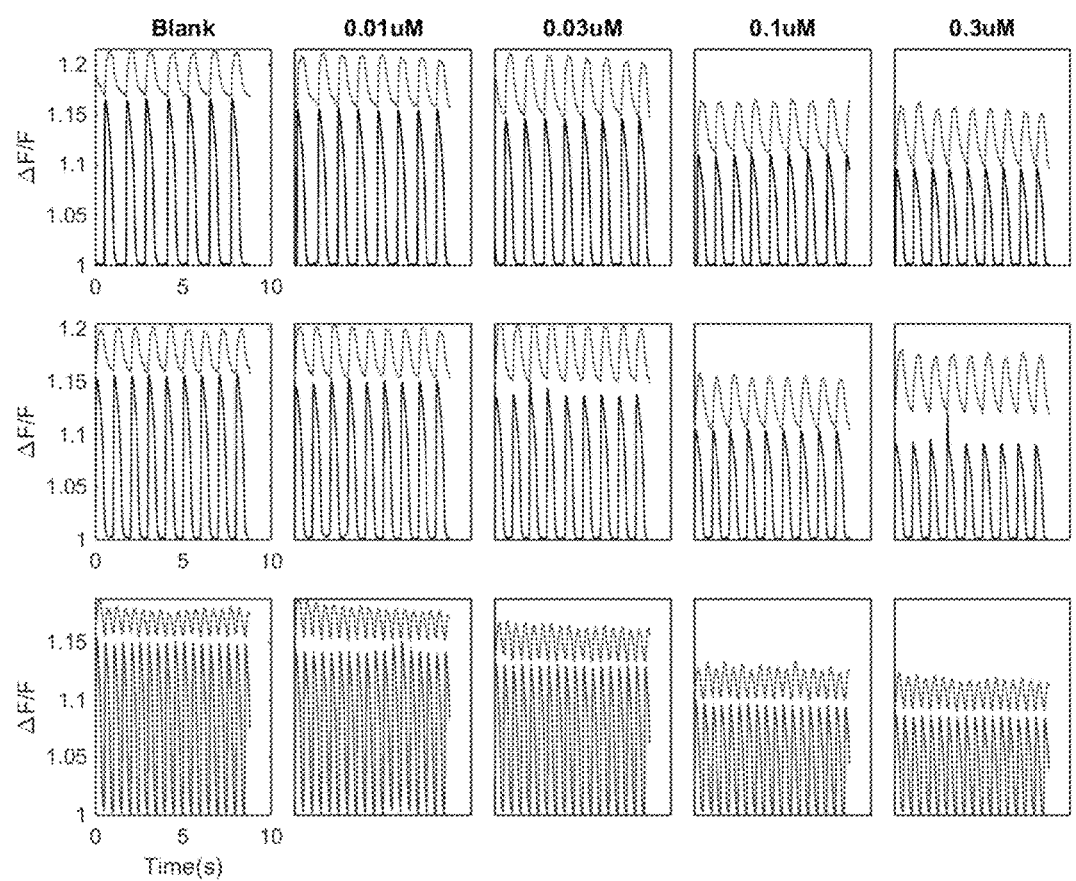
FIG. 33 shows the effects of JNJ 303 on cardiomyocytes.

FIG. 33 shows the effects of JNJ 303 on cardiomyocytes.

Figure 34:
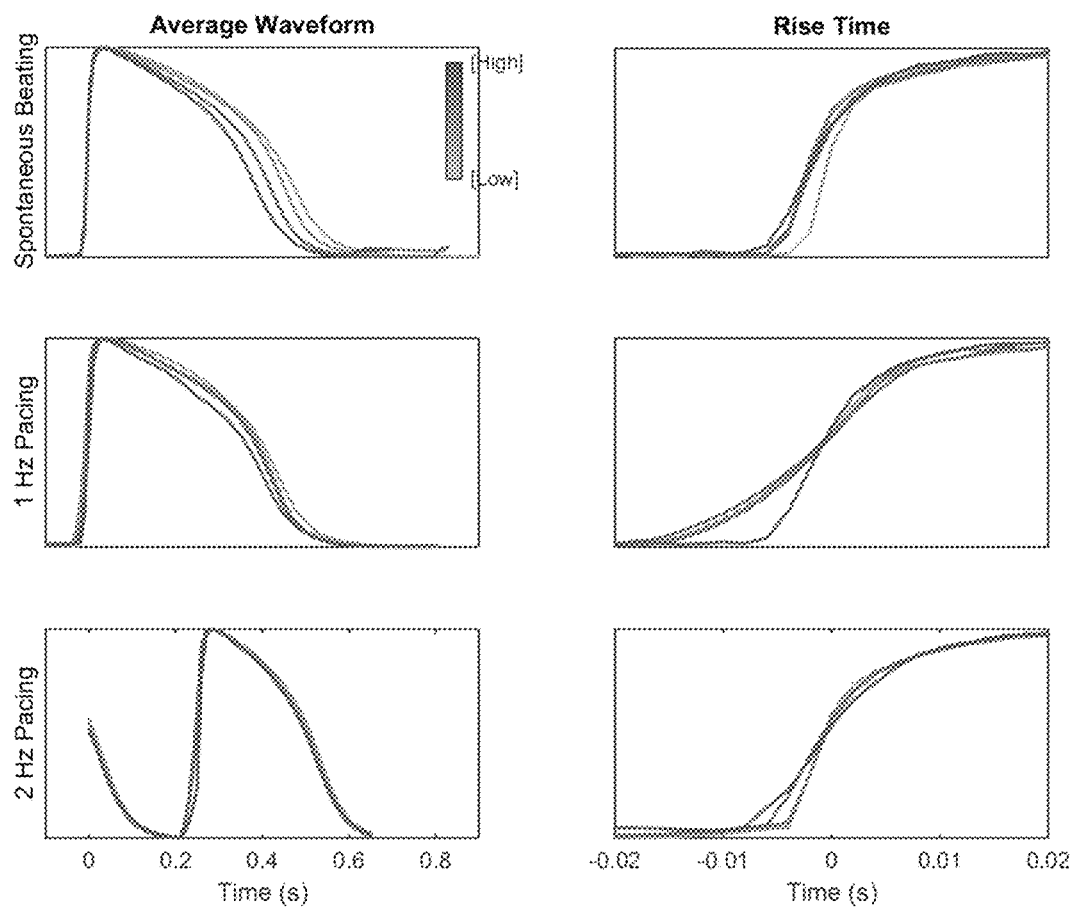
FIG. 34 shows the effect of JNJ 303 on average AP waveform and rise time

FIG. 34 shows the effect of JNJ 303 on average AP waveform and rise time

Figure 35:
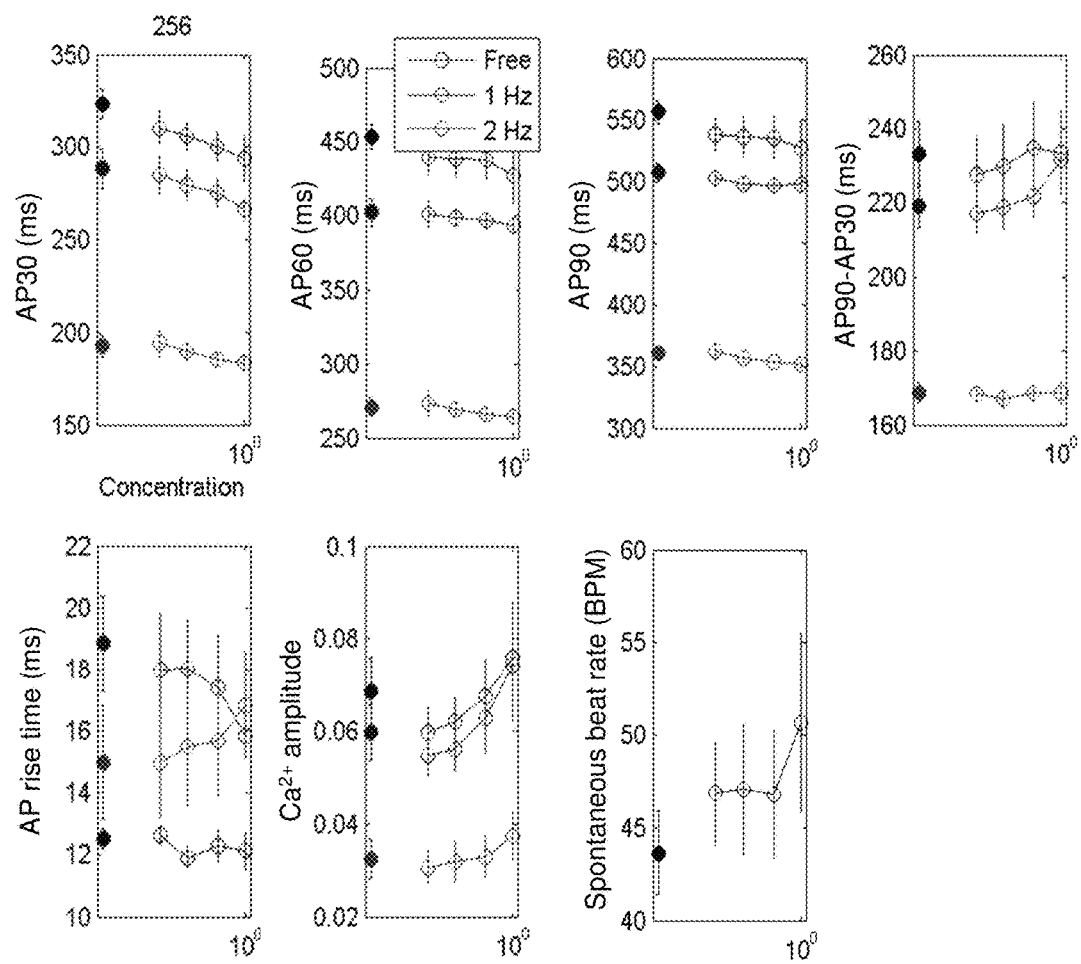
FIG. 35 shows the JNJ 303 dose dependence of certain AP waveform and CT effects.

FIG. 35 shows the JNJ 303 dose dependence of certain AP waveform and CT effects.

Figure 36:
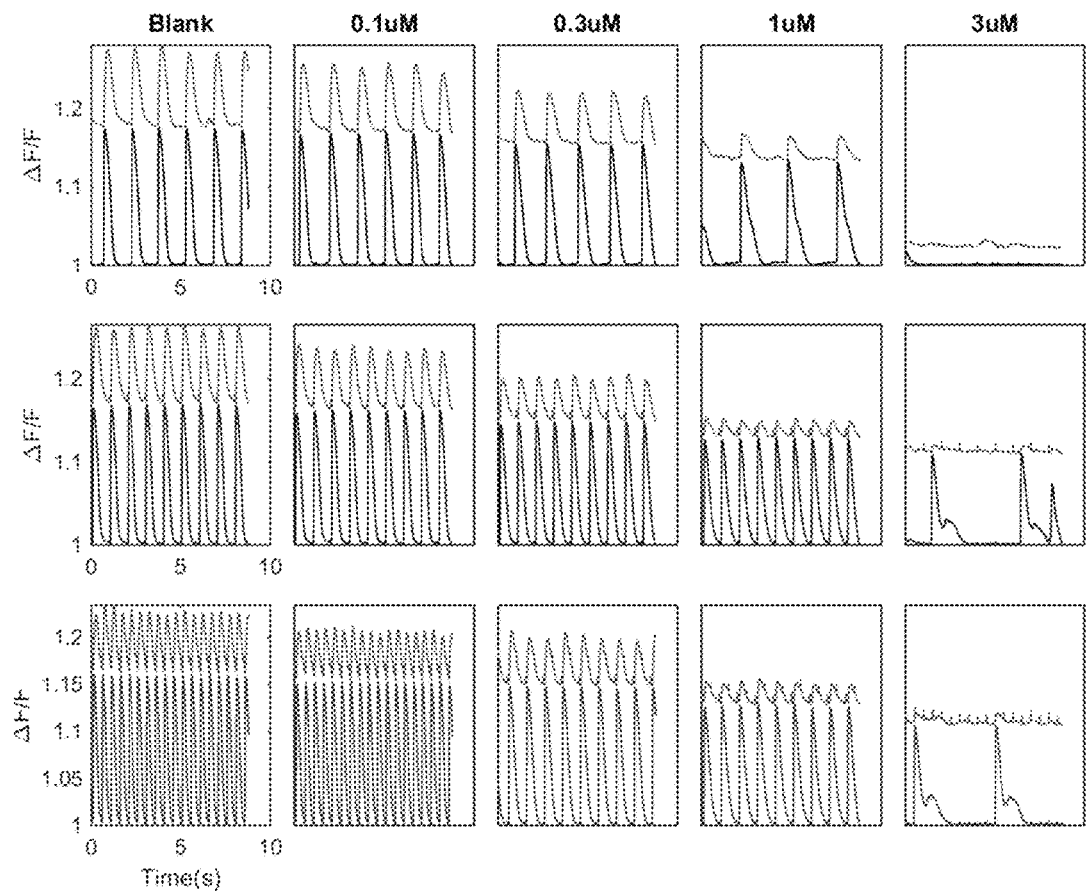
FIG. 36 shows the effects of flecainide on cardiomyocytes.

FIG. 36 shows the effects of flecainide on cardiomyocytes.

Figure 37:
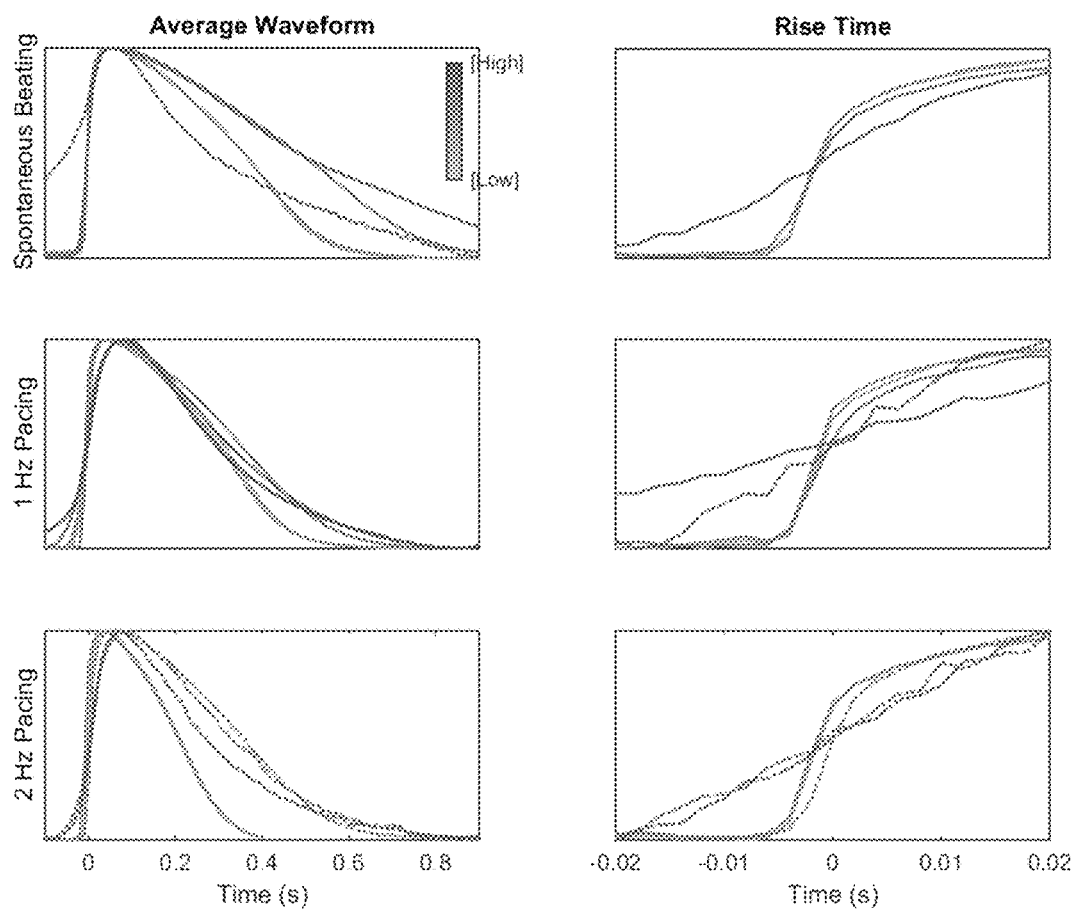
FIG. 37 shows the effect of flecainide on average AP waveform and rise time

FIG. 37 shows the effect of flecainide on average AP waveform and rise time

Figure 38:
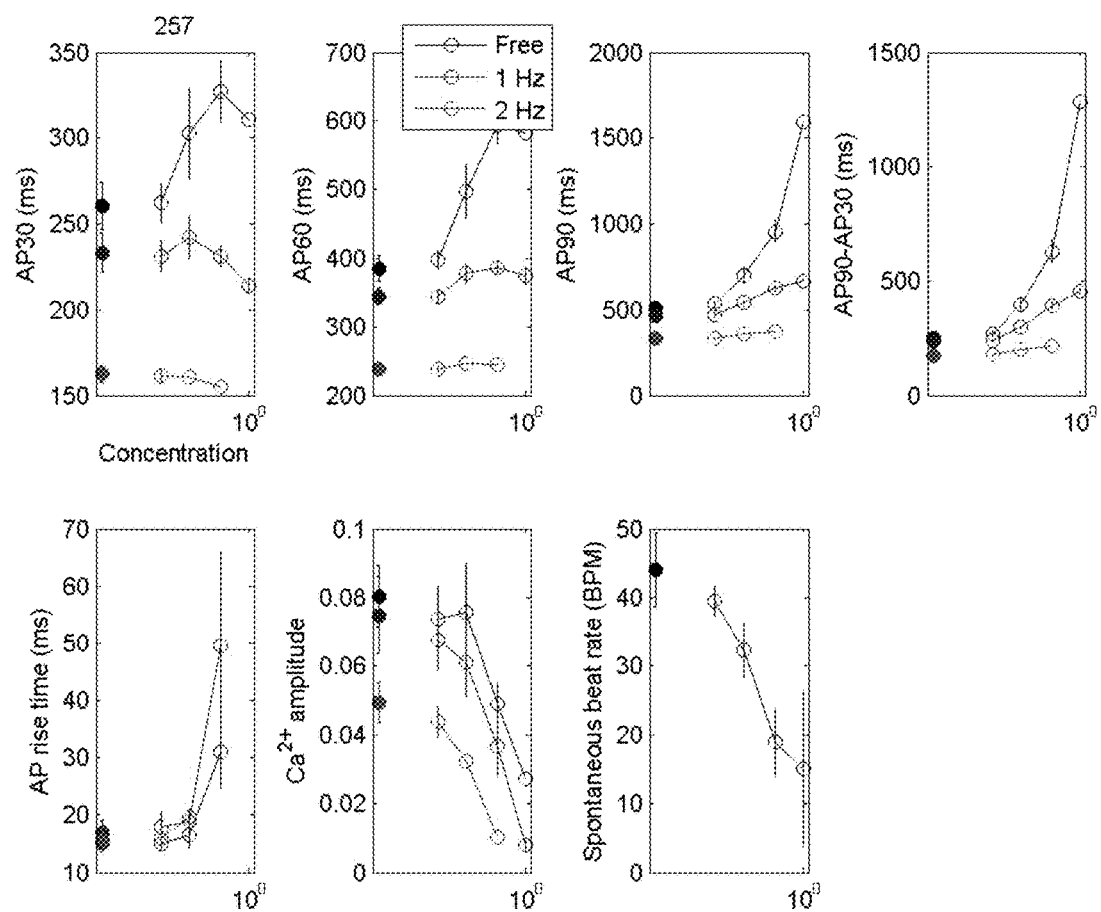
FIG. 38 shows the flecainide dose dependence of certain AP waveform and CT effects.

FIG. 38 shows the flecainide dose dependence of certain AP waveform and CT effects.

Figure 39:
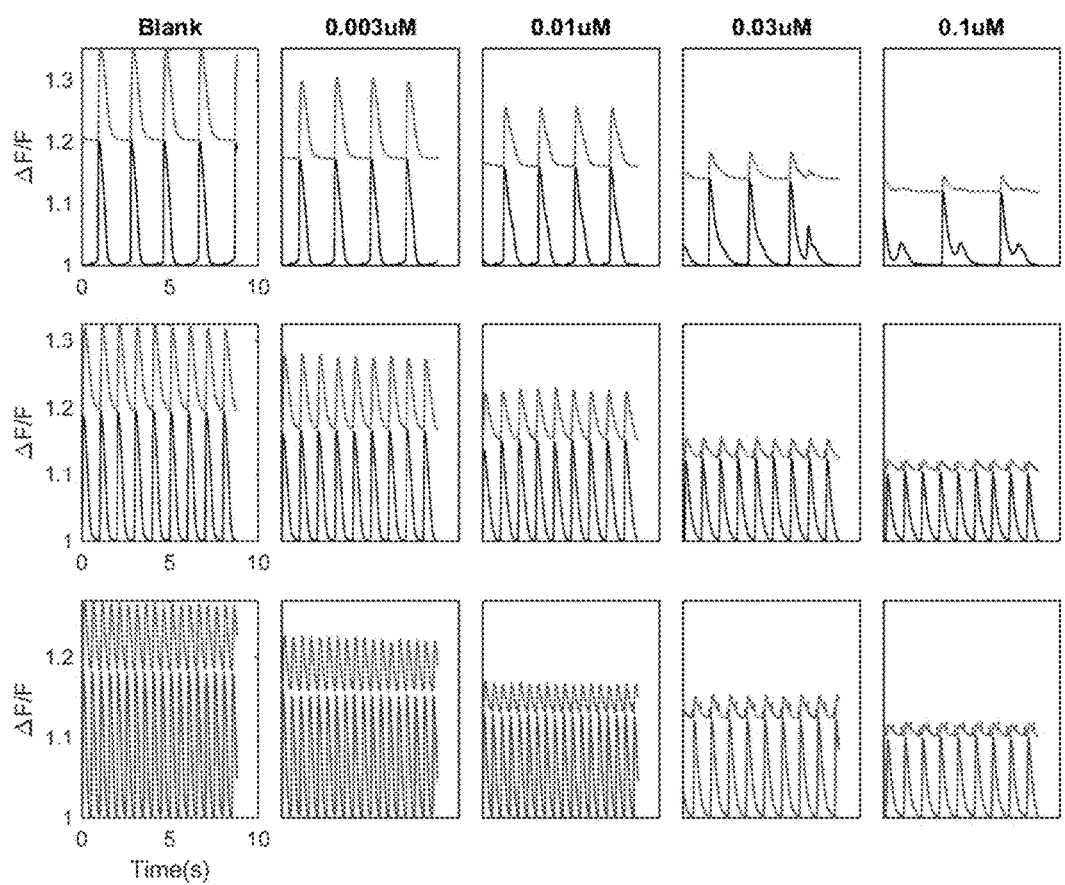
FIG. 39 shows the effects of E-4031 on cardiomyocytes.

FIG. 39 shows the effects of E-4031 on cardiomyocytes.

Figure 40:
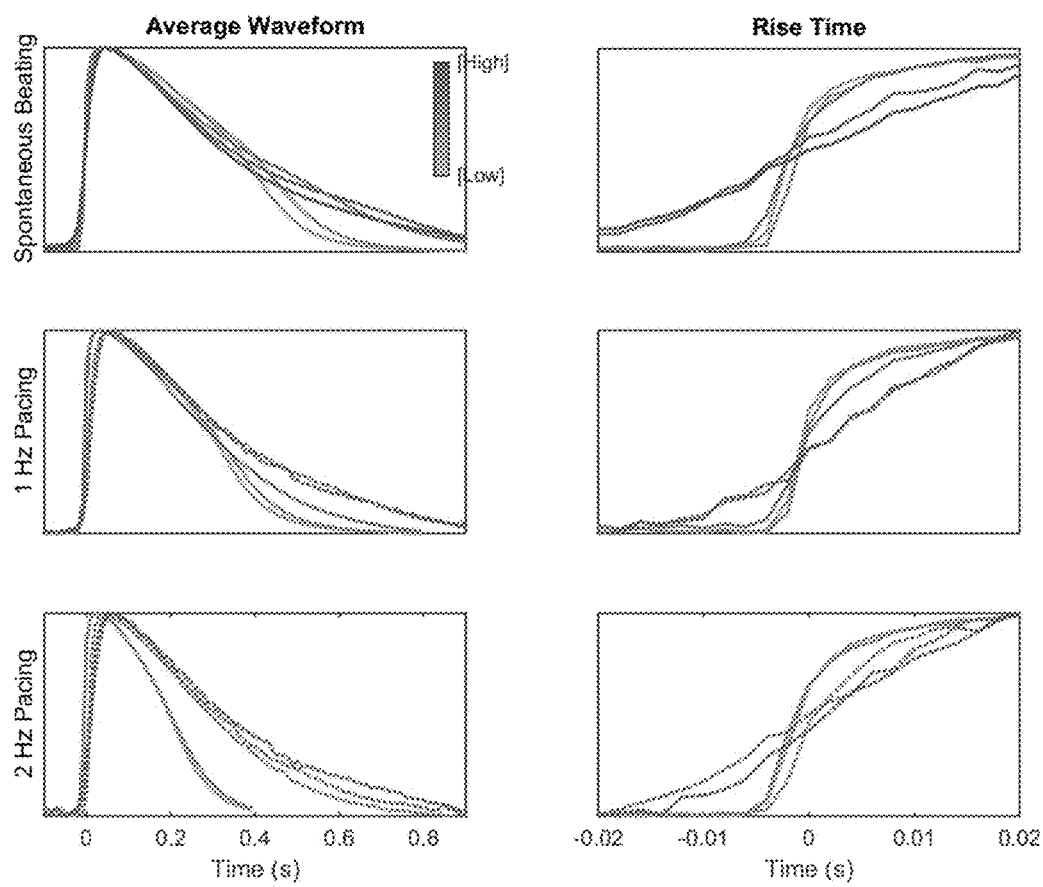
FIG. 40 shows the effect of E-4031 on average AP waveform and rise time

FIG. 40 shows the effect of E-4031 on average AP waveform and rise time

Figure 41:
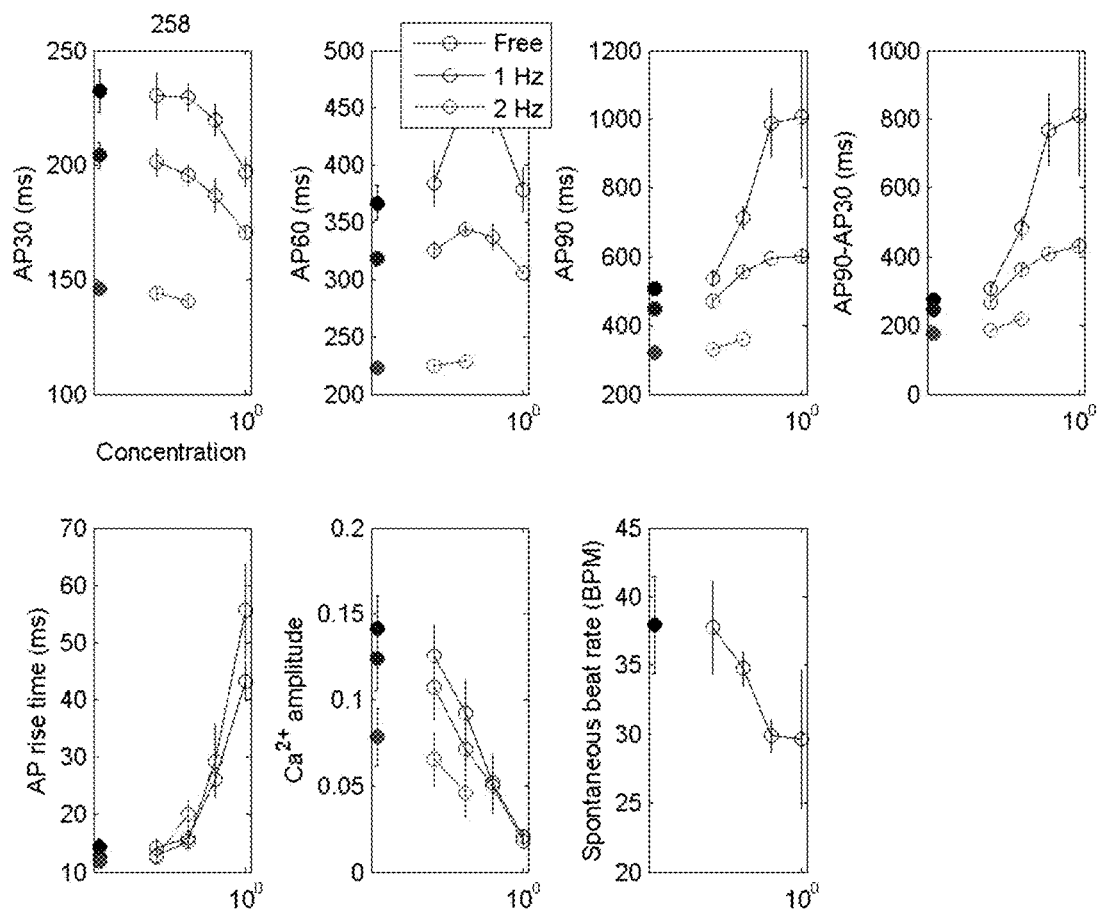
FIG. 41 shows the E-4031 dose dependence of certain AP waveform and CT effects.

FIG. 41 shows the E-4031 dose dependence of certain AP waveform and CT effects.

Figure 42:
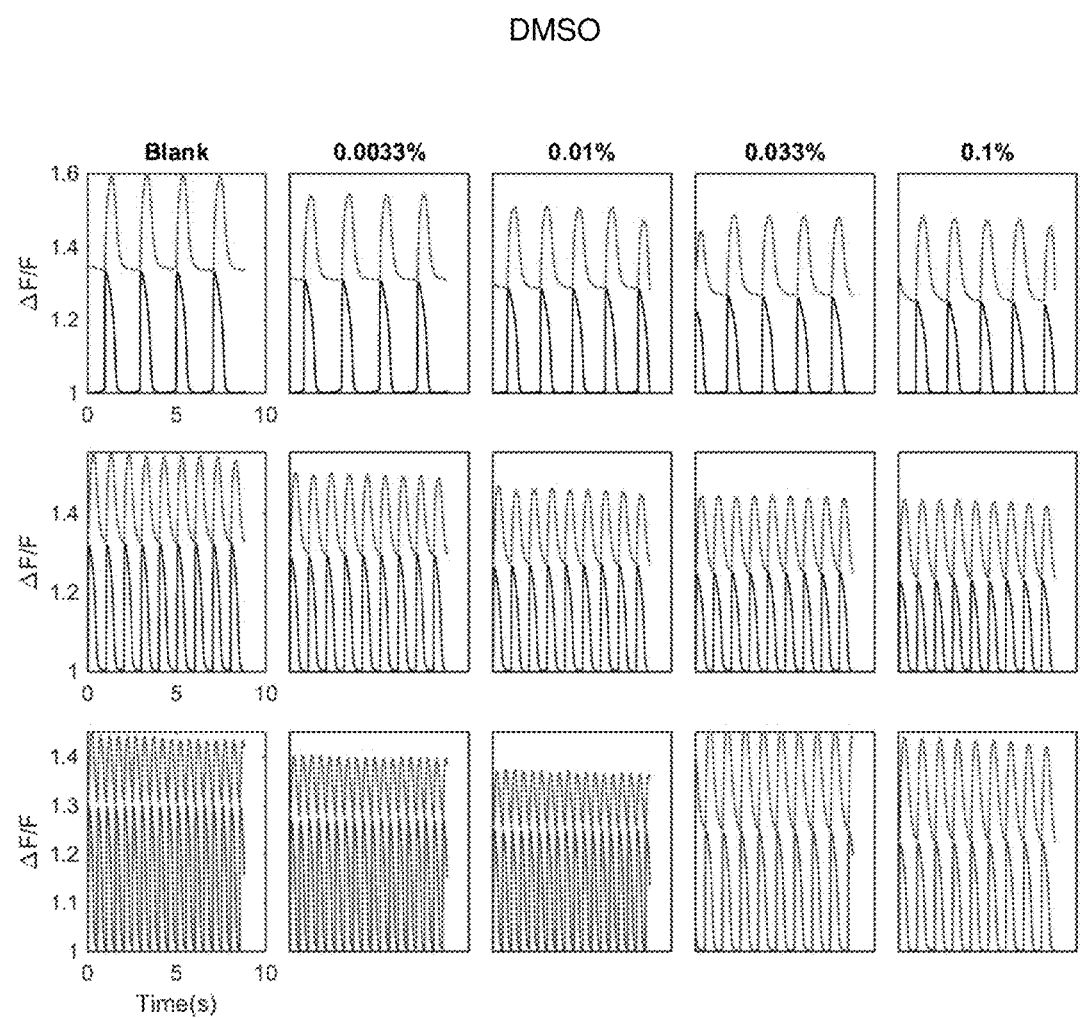
FIG. 42 shows the effects of DMSO on cardiomyocytes.

FIG. 42 shows the effects of DMSO on cardiomyocytes.

Figure 43:
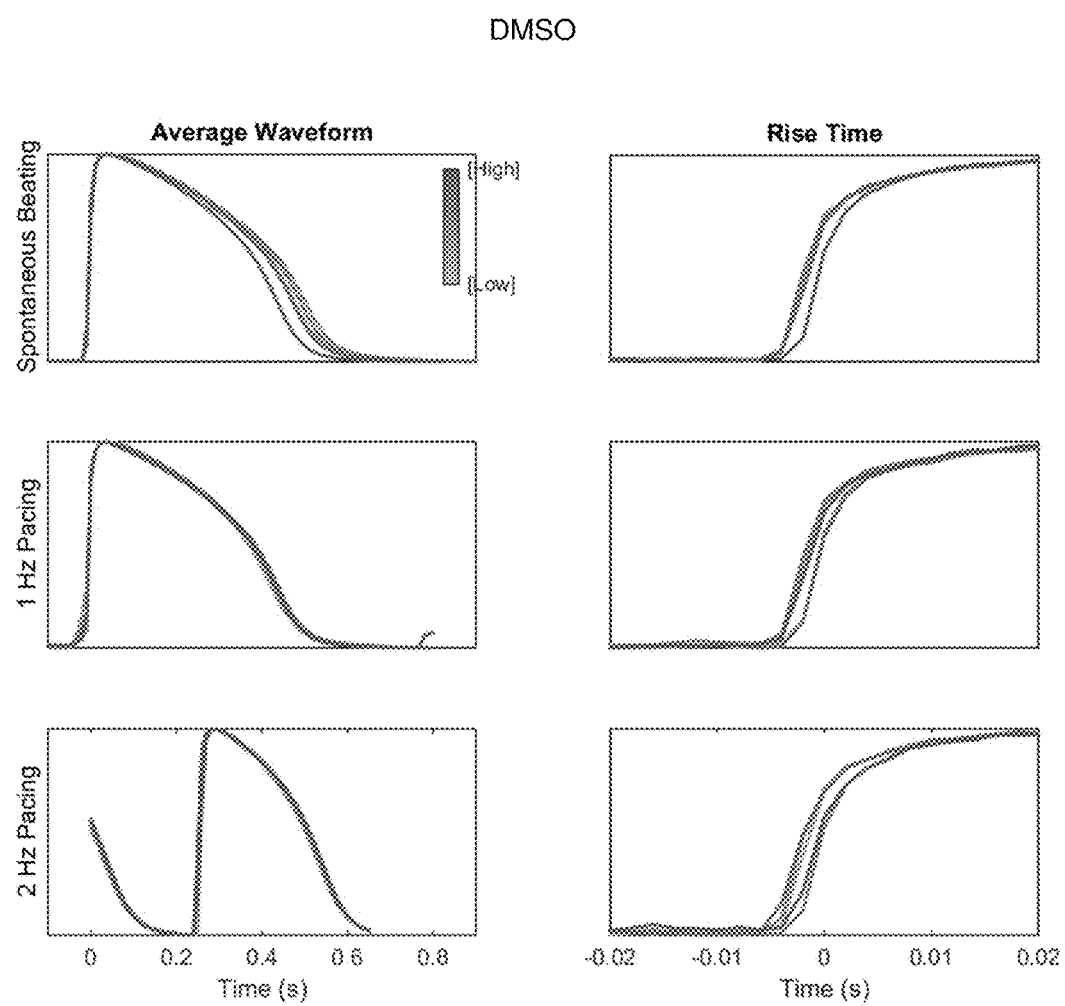
FIG. 43 shows the effect of DMSO on average AP waveform and rise time

FIG. 43 shows the effect of DMSO on average AP waveform and rise time

Figure 44:
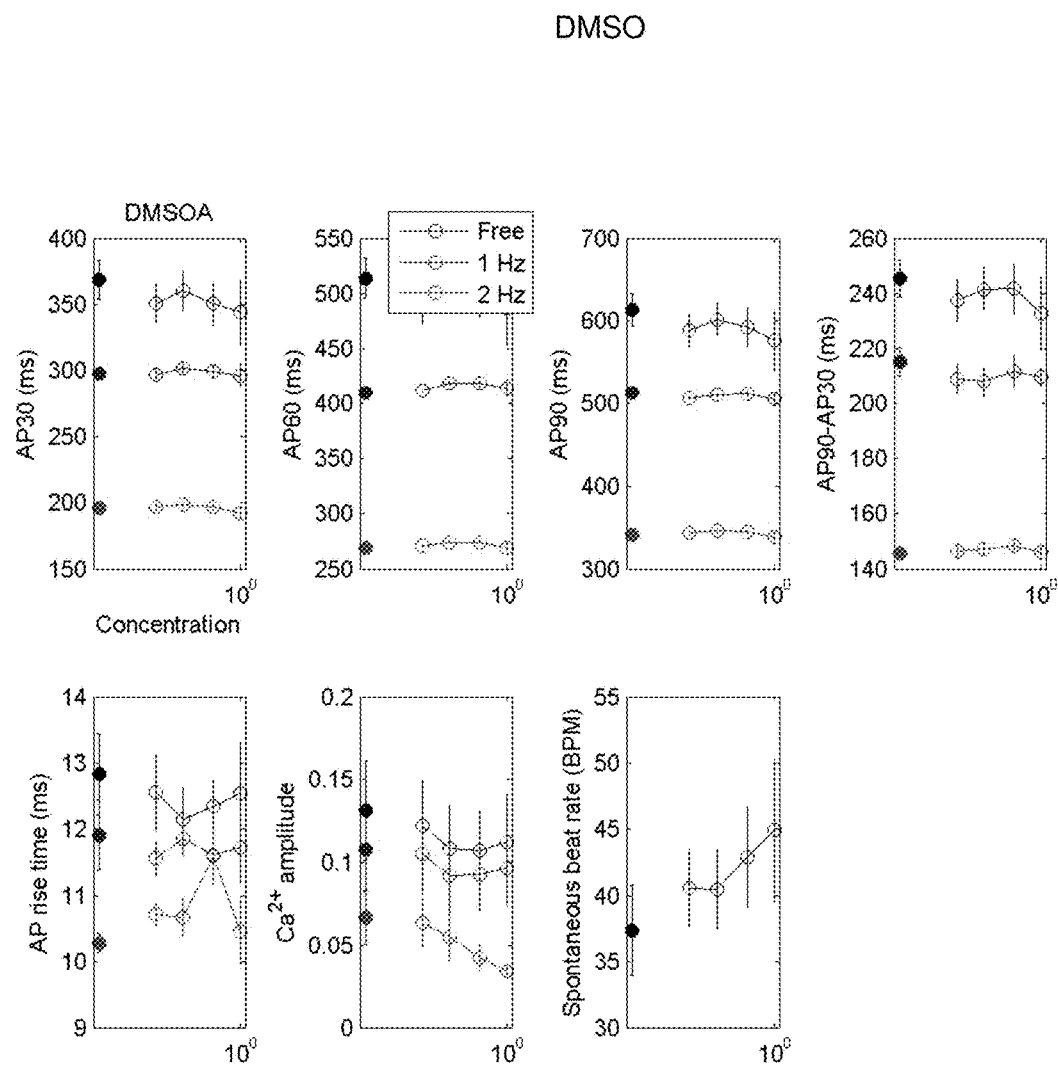
FIG. 44 shows the DMSO dose dependence of certain AP waveform and CT effects.

FIG. 44 shows the DMSO dose dependence of certain AP waveform and CT effects.

Optogenetic actuator protein such as a channelrhodopsin variant (e.g., CheRiff, TsChR, or PsChR) allows for repeated blue light stimulation to pace cardiomyocytes. The use of a reporter protein, CaViar, allowed for simultaneous detection of voltage and Ca2+ dynamics in the same cells, all with high signal-to-noise, low photobleaching and low phototoxicity.

Optopatch measures effects of compounds in spontaneously beating and paced cardiomyocytes. For several of the compounds, significant acute effects on the electrophysiological parameters of the CMs are observed. The data demonstrate that the Optopatch technology reports the electrophysiological and Ca2+ response of cardiomyocytes to pharmacological perturbations, with high accuracy, throughput, and information content. This platform should prove useful in reaching one of the major end goals of the CiPA initiative, namely a new in vitro assay with hiPSC-derived CMs for the accurate reporting of cardiotoxic effects of drug compounds.

What is claimed is:

1. A cardiomyocyte expressing:
    at least one microbial rhodopsin as an optogenetic reporter of voltage activity, wherein the microbial rhodopsin is one selected from the list consisting of QuasAr1 and QuasAr2;
    a light-gated ion channel as an optogenetic actuator of electrical activity; and
    a genetically encoded calcium indicator as an optogenetic reporter of calcium level.

2. The cardiomyocyte of claim 1, wherein the genetically encoded calcium indicator comprises a GCaMP variant.

3. The cardiomyocyte of claim 2, wherein the genetically encoded calcium indicator is one selected from the list consisting of jRCaMP1a, jRGECO1a and RCaMP2.

4. The cardiomyocyte of claim 3, wherein the light-gated ion channel comprises a blue-shifted actuator and the genetically encoded calcium indicator comprises a red-shifted calcium indicator.

5. The cardiomyocyte of claim 4, wherein the light-gated ion channel comprises an algal channelrhodopsin.

6. The cardiomyocyte of claim 5, wherein the light-gated ion channel comprises a blue-shifted actuator that is one selected from the list consisting of CheRiff, TsChR, and PsChR.

7. The cardiomyocyte of claim 6, wherein the microbial rhodopsin and the genetically encoded calcium indicator are expressed together as part of a fusion protein.

* * * * *